United States Patent [19]
Ratner

[11] Patent Number: 6,160,015
[45] Date of Patent: *Dec. 12, 2000

[54] COMPOUNDS USEFUL IN THE TREATMENT OF NEUROFIBROMATOSIS

[75] Inventor: Nancy Ratner, Cincinnati, Ohio

[73] Assignee: University of Cincinnati, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 09/361,959

[22] Filed: Jul. 27, 1999

Related U.S. Application Data

[63] Continuation of application No. 08/981,779, filed as application No. PCT/US96/11577, Jul. 11, 1996.
[60] Provisional application No. 60/001,130, Jul. 13, 1995.

[30] Foreign Application Priority Data

Mar. 11, 1996 [GB] United Kingdom ............ 9605142

[51] Int. Cl.[7] ................................ A61K 31/235
[52] U.S. Cl. ............................................. 514/542
[58] Field of Search ............................. 514/542

[56] References Cited

U.S. PATENT DOCUMENTS

| | | | |
|---|---|---|---|
| 5,420,334 | 5/1995 | Singh et al. | 560/138 |
| 5,504,212 | 4/1996 | deSolms et al. | 546/336 |
| 5,523,430 | 6/1996 | Patel et al. | 554/40 |
| 5,532,359 | 7/1996 | Marsters, Jr. et al. | 540/522 |
| 5,571,792 | 11/1996 | Bolton et al. | 514/18 |

FOREIGN PATENT DOCUMENTS

| | | |
|---|---|---|
| 0 618 221 A2 | 10/1994 | European Pat. Off. . |
| 0 675 112 A1 | 10/1995 | European Pat. Off. . |
| WO95/10514 | 4/1995 | WIPO . |
| WO95/10515 | 4/1995 | WIPO . |
| WO95/10516 | 4/1995 | WIPO . |

OTHER PUBLICATIONS

Molecular and Cellular Biology, vol. 17. No. 2, pp. 862–872 (1997), by H. A. Kim, et al.

J. Neuroscience 22, vol. 2 pp. 1499, by H.A. Kim, et al.

Cancer Research, vol. 55, pp. 3569–3575 (1995), by N. Yan, et al.

Medline Abstract 91187510, vol. 16, No. 6, pp. 575–580 (1990), by Nativie, et al.

Oncogene, vol. 11, No. 2, pp. 325–335 (1995), by Kim, et al.

P. Natl. Acad. Sci. USA, vol. 91, pp. 9141–9145 (1994), by N. Khol, et al.

J. Neuroscience 22(2) 1499 Kim et al, "NF1–deficient mouse Schwann cells are anglogenic, invasive and can be induced to hyperproliferate: reversion of some phenotypes by an inhibitor of farnesyl protein transferase". (no publication date available).

Cancer Research 55, 3569–3575, 1995, Yan et al, "Farnesyltransferase Inhibitors Block the Neurofibromatosis Type I (NF1) Malignant Phenotype".

Medline 1990 16 (6) 575–580 Nativio et al, "Pediatric Nursing".

Oncogene vol. 11, No. 2 325–335 1995 Kim et al, "Schwann cells from neurofibromin deficient mice exhibit activation of p21ras, inhibition of cell proliferation and morphological changes".

Proc. Natl. Acad. Sci. USA vol. 91 9141–9145 1994 Kohl et al, "Protein farnesyltransferase inhibitors block the growth of ras–dependent tumors in nude mice".

Molecular and Cellular Biology, 1997 862–872 Kim et al, "Nf1–Deficient Mouse Schwann Cellas are Angiogenic and Invasive and Can be Induced to Hyperproliferate: Reversion of Some Phenotypes by an Inhibitor of Farnesyl Protein Transferase".

*Primary Examiner*—Raymond Henley, III
*Attorney, Agent, or Firm*—David A. Muthard; Mark R. Daniel

[57] ABSTRACT

The present invention relates to compositions useful in the treatment of benign proliferative disorder neurofibromatosis comprising a farnesyl protein transferase inhibitor. Further contained in this invention are methods of treating benign proliferative disorder neurofibromatosis in a mammal, which methods comprise administering to said mammal, a farnesyl protein transferase inhibitor.

8 Claims, 3 Drawing Sheets

COMPOUNDS USEFUL IN THE TREATMENT OF NEUROFIBROMATOSIS

This is a continuation of application Ser. No. 08/981,779 filed Jan. 12, 1998, and claim priority under 35USC119(e) over Ser. No. 60/001,130 filed Jul. 13, 1995 and which is a 371 of PCT/US96/11577 filed Jul. 11, 1996.

BACKGROUND OF THE INVENTION

A genetic defect underlies von Recklinghausen neurofibromatosis, known as type 1 neurofibromatosis (NF1), which is inherited as an autosomal dominant trait, and affects 1 in 3,500 humans. Analysis of the steps that lead to disease manifestations and development of therapeutic strategies against NF1 is complicated by the number of abnormalities in NF1 patients and the diversity of cell types involved. A National Institute of Health consensus panel has defined diagnostic criteria, two or more of which define a diagnosis of NF1. The criteria are: 1) six or more cafe-au-lait macules over 5 mm in greatest diameter (prepubertal) or over 15 mm (postpubertal); 2) freckling in the axillary or inguinal regions; 3) optic glioma; 4) two or more iris Lisch nodules; 5) a distinct osseus lesion; 6) a first degree relative with NF1; and 7) two or more nerve sheath tumors (neurofibromas) of any type or one plexiform neurofibroma. More recently it has become clear that up to 40% of children with NF1 show learning disabilities.

The NF1 gene is located on the proximal long arm of human chromosome 17, and extends about 320 kb of genomic DNA; all informative NF1 families showed linkage to this locus. Mutational analysis identified mutations in about 15% of patient DNA with no identified hot spots; remaining mutations may be in untested intron sequences. Mutations including translocations, insertions, deletions and base-pair substitutions predict truncated or inactive protein, with no evidence for dominant negative effects. In malignant tumors (neurofibrosarcomas, pheochromocytomas and juvenile myelocytic leukemias) associated with NF1, mutations in the previously normal somatic allele have been detected, suggesting that the NF1 gene can be categorized with tumor suppresser genes such a Rb and NF2. However, it remains unclear if mutations in both NF1 alleles is a prerequisite for the formation of benign lesions, including neurofibromas.

Ras is an intracellular messenger activated by binding GTP subsequent to receptor activation; Ras activation recruits the serine-threonine kinase raf to the plasma membrane and leads to activation of raf by an unknown mechanism. Raf activation leads to activation of a cascade of protein kinases (ERKs and MAPKs) and changes in gene transcription. Other pathways are also downstream of ras activation. In many tumor cells, mutant oncogenic alleles of ras genes specify structurally altered forms of Ras which have a reduced ability to hydrolyze GTP when compared with the wild type ras gene product (Gibbs et al., *Proc. Natl. Acad. Sci. USA,* 81:5704–5708 (1984); McGrath et al., *Nature,* 310:644–649 (1984); Sweet et al., *Nature* 311:273–275 (1984)). Additionally, these oncogenic forms of Ras have been found to exhibit a greatly diminished sensitivity to the ras GTPase activating protein (GAP) (Trahey and McCormick, Science, 242:1697–1700 (1987); Vogel et al., *Nature,* 335:90–03 (1988)). These findings suggest that the GTP-bound state of Ras represents an activated, signal-emitting form of Ras which is normally inactivated through GTP hydrolysis, yielding an inactive GDP-bound form of the protein. Because of their reduced intrinsic GTPase activity and resistance to GAP, oncogenic forms of Ras may be trapped in this activated state for extended periods of time, thereby flooding the cell with growth-stimulatory signals.

In part because Ras has no other apparent catalytic activities associated with it, it is hypothesized that Ras acts as a regulatory subunit of another protein that serves as its effector, releasing mitogenic signals when prompted to do so by activated, GTP-bound Ras. One candidate for such an effector protein is GAP itself. However, GAP has no obvious catalytic domains that might play a role in metabolic processes associated with cell proliferation. For this reason, GAP itself might act as a signal transducer which passes Ras-initiated signals on to bona fide effectors still further downstream in the signaling cascade.

The NF1 mRNA is >12 kb in size, and encodes a 320 kd protein, neurofibromin. A 360 amino acid segment near the middle of the protein sequence shows 30% homology to the catalytic domain of the GTPase activating protein (GAP) and the yeast IRA1 and IRA2 proteins that stimulate GTPase activity of Ras proteins. The GAP-related domain of neurofibromin exhibits GAP activity toward human and yeast Ras proteins and complements the loss of function in yeast IRA mutants. Numerous studies have confirmed the GAP activity of full-length neurofibromin as well as the GAP-related domain. Loss of neurofibromin through mutations at the NF1 locus are predicted to cause a failure to terminate Ras signals, and to cause alterations in growth and differentiation of affected cells.

It has been shown that neurofibrosarcoma (malignant Schwann cell) cell lines contain little neurofibromin, and at the same time show increased levels of GTP bound to Ras, suggesting a correlation between loss of neurofibromin and Ras regulation in such cells (deClue et al., *Cell,* 69:265–273 (1992)). These data suggest that neurofibromin is the major regulator of Ras in malignant Schwann cells, in spite of the fact that these cells contain normal levels of p120 GAP protein. Decreasing levels of Ras-GTP in the neurofibrosarcoma cells by overexpressing p120 GAP led to reduced frequency of colony formation and decreased growth in agar, suggesting that Ras-GTP contributes to some of the transformed properties of these malignant Schwann cells.

Recently mice containing targeted inactivating mutations at the NF1 locus were studied (Brannan et al., *Genes and Dev.,* 8:1019–1029 (1994)). Neurofibromin expression in adult mice and embryos from transgenic mice that were heterozygous or homozygous at the NF1 locus was analyzed. Neurofibromin was found to be present at roughly 50% of normal levels in heterozygous mice and was undetectable in homozygous mice, indicating that the latter were true nulls. Null embryos die between day 11.5 and 14 of gestation, prior to significant nerve development, apparently as a result of cardiac malformation.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are competitive with farnesyl diphosphate (FPP) and can be structural analogs of FPP or not directly analogous. The second class of inhibitors are competitive with the protein substrates (e.g., Ras) for the enzyme. The protein substrate-competitive inhibitors that have been described are generally cysteine containing molecules that are related to the CAAX motif that is the signal for protein prenylation. (Schaber et al ibid; Reiss et. al., ibid; Reiss et al., PNAS, 88:732–736 (1991)). Such compounds may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). Recently, protein substrate-competitive inhibitors that lack a thiol moiety have been described (WO 95/09000; WO 95/09001; WO 95/10514; WO 95/10515; WO 95/10516; WO 95/08542; WO 95/11917; and WO 95/12612).

Inhibitors of FPTase have recently been described that incorporate characteristics of both farnesyl pyrophosphate and the CAAX motif (R. S. Bhide et al., Bioorg. Med. Chem. Lett., 4:2107–2112 (1994) and (V. Manne et al., Oncogene, 10:1763–1779 (1995)).

It is, therefore, an object of this invention to develop methods of treating and preventing benign proliferative disorder neurofibromatosis which utilize compounds which are known to be inhibitors of farnesyl-protein transferase.

SUMMARY OF THE INVENTION

The present invention relates to compositions useful in the prevention and treatment of benign proliferative disorder neurofibromatosis comprising a farnesyl protein transferase inhibitor. Further contained in this invention are methods of treating and preventing benign proliferative disorder neurofibromatosis in a mammal, which methods comprise administering to said mammal, a farnesyl protein transferase inhibitor.

Effects of exposure of NF1 wild type mouse Schwann cells (+/+) and mutant type cells (−/−) to media containing various concentrations of forskolin is shown.

Figure 3:
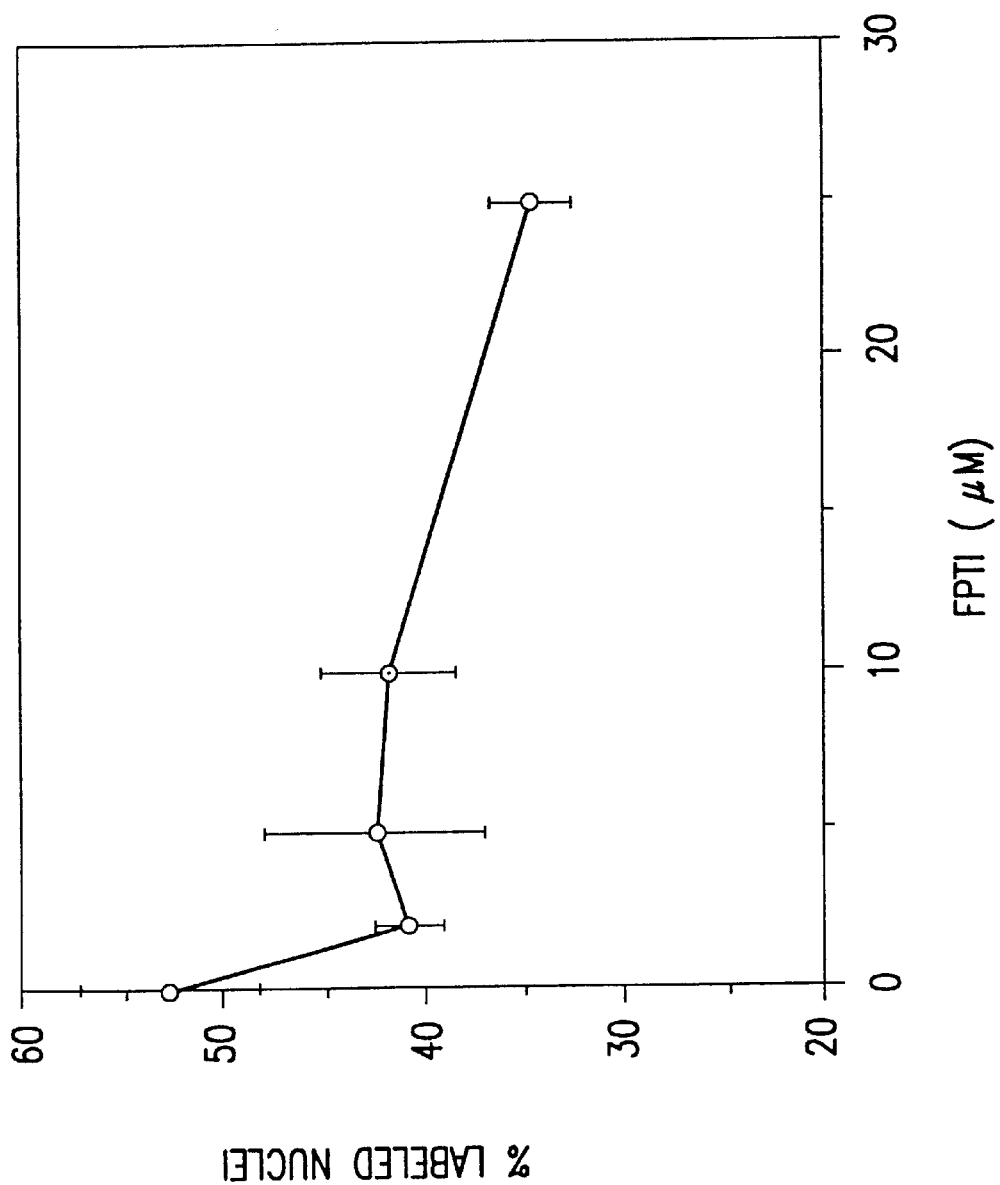

FIG. 3 Effect of a Farnesyl-protein Transferase Inhibitor on Forskolin mediated Proliferation:
Effects of preincubation of NF1 mutant (−/−) type Schwann cells with Compound A is shown. Cell proliferation was mediated by the addition of forskolin.

DETAILED DESCRIPTION OF THE INVENTION

According to one aspect of this invention, it is now possible to achieve a therapeutic effect in a mammal in need of treatment of benign proliferative disorder neurofibromatosis with pharmaceutically effective amounts of a farnesyl protein transferase inhibitor. Such a compound is also useful in the prevention of the disease.

It has been discovered that Schwann cells lacking neurofibromin proliferate more slowly than do wild type Schwann cells in response to axons or glial growth factor (GGF), specific Schwann cell mitogens. Those null Schwann cells also show increased levels of GTP bound to Ras and show hyperplasia in response to forskolin, an activator of adenylate cyclase, that may mimic endogenous factors in Schwann cell tumors in NF1 patients.

It has been surprisingly discovered that a farnesyl-protein transferase inhibitor inhibits the forskolin-mediated proliferation of null Schwann cells. Such inhibition of that proliferative effect is useful in the treatment of NF1 associated with mutations in the NF1 gene that leads to loss or reduction of neurofibromin activity.

The present invention is not limited in any way by the specific farnesyl-protein transferase inhibitor. Either a protein substrate-competitive inhibitor and/or a farnesyl pyrophosphate-competitive inhibitor now known or subsequently discovered or developed may be utilized. Farnesyl-protein transferase inhibitors useful in the instant invention are described hereinbelow.

The composition of the instant invention may comprise a protein substrate-competitive farnesyl-protein transferase inhibitor that incorporates a cysteinyl or sulfhydryl containing moiety at the N-terminus of the molecule. Thus the following compounds, well known in the art, are useful as protein substrate-competitive inhibitors in the instant invention:

a) a peptide that comprises the amino acids $CA_1 A_2 X$, wherein:
  C=cysteine;
  $A_1$=an aliphatic amino acid;
  $A_2$=an aliphatic amino acid; and
  X=any amino acid;

b) Cys-$Xaa^1$-$Xaa^2$-$Xaa^3$-$NRR^1$, wherein
  Cys=cysteine;
  $Xaa^1$=any amino acid in the natural L-isomer form;
  $Xaa^2$=any amino acid in the natural L-isomer form; and
  $Xaa^3$-$NRR^1$=an amide of any amino acid in the natural L-isomer form, wherein R and $R^1$ are independently selected from hydrogen, $C_1$–$C_{12}$ alkyl, aralkyl, or unsubstituted or substituted aryl;

c) Cys-$Xaa^1$-$Xaa^2$-$Xaa^3$, wherein
  Cys=cysteine;
  $Xaa^1$=any amino acid;

Xaa² = the amino acid phenyl alanine or a p-fluorophenylalanine; and

Xaa³ = any amino acid;

d) Cys-Xaa¹-dXaa²-Xaa³, wherein

Cys = cysteine;

Xaa¹ = any amino acid in the natural L-isomer form;

dXaa² = any amino acid in the natural L-isomer form; and

Xaa³ = any amino acid in the natural L-isomer form;

e) U.S. Pat. No. 5,238,922, incorporated herein by reference,

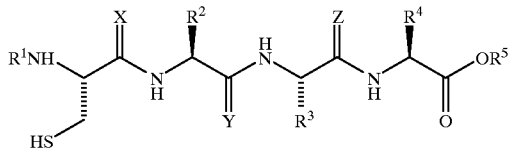

wherein:

X, Y, and Z are independently $H_2$ or O, provided that at least one of these is $H_2$;

$R^1$ is H, an alkyl group, an acyl group, an alkylsulfonyl group or aryl sulfonyl group, wherein alkyl and acyl groups comprise straight chain or branched chain hydrocarbons of 1 to 6 carbon atoms, or in the alternative, $R^1NH$ may be absent;

$R^2$, $R^3$ and $R^4$ are the side chains of naturally occurring amino acids, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms, wherein the aliphatic substitutents may be substituted iwth an aromatic or heteroaromatic ring; and $R^5$ is H or a straight or branched chain aliphatic group, which may be substituted with an aromatic or heteroaromatic group;

f) U.S. Pat. No. 5,340,828, incorporated herein by reference,

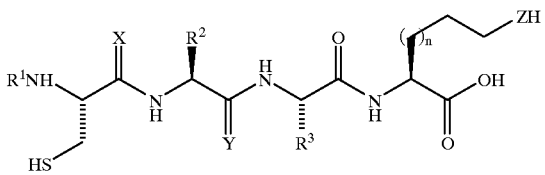

wherein:

X and Y are independently $H_2$ or O, provided that at least one of these is $H_2$;

$R^1$ is H, an alkyl group, an acyl group, an alkylsulfonyl group or aryl sulfonyl group, wherein alkyl and acyl groups comprise straight chain or branched chain hydrocarbons of 1 to 6 carbon atoms, or in the alternative, $R^1NH$ may be absent;

$R^2$ and $R^3$ are the side chains of naturally occurring amino acids, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms, wherein the aliphatic substitutents may be substituted with an aromatic or heteroaromatic ring;

Z is O or S; and n is 0, 1 or 2;

g) U.S. Pat. No. 5,340,828, incorporated herein by reference,

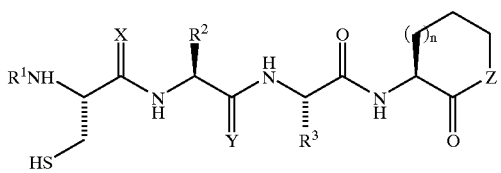

wherein:

X and Y are independently $H_2$ or O, provided that at least one of these is $H_2$;

$R^1$ is H, an alkyl group, an acyl group, an alkylsulfonyl group or aryl sulfonyl group, wherein alkyl and acyl groups comprise straight chain or branched chain hydrocarbons of 1 to 6 carbon atoms, or in the alternative, $R^1NH$ may be absent;

$R^2$ and $R^3$ are the side chains of naturally occurring amino acids, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms, wherein the aliphatic substitutents may be substituted with an aromatic or heteroaromatic ring;

Z is O or S; and n is 0, 1 or 2;

h) U.S. Pat. No. 5,352,705, incorporated herein by reference,

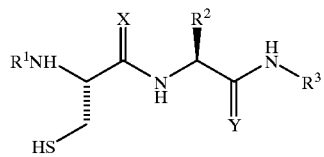

wherein:

X and Y are independently $H_2$ or O;

$R^1$ is an alkyl group, hydrogen, an acyl group, an alkylsulfonyl group or arylsulfonyl group, wherein alkyl and acyl groups comprise straight chain or branched chain hydrocarbons of 1 to 6 carbons atoms, which alternatively may be substituted with an aryl group;

$R^2$ is the side chains of naturally occurring amino acids, or in the alternative may be substituted or unsubstituted aliphatic, aromatic or heterocyclic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

$R^3$ is an aromatic or heteroaromatic ring or in the alternative an alkyl group or an aryl or heteroaryl substituted alkane, wherein the aromatic ring is unsubstituted or in the alternative, substituted with one or more groups which may be alkyl, halo, alkoxy, trifluoromethyl, or sulfamoyl groups, and which may be polycyclic;

i) U.S. Pat. No. 5,326,773; PCT Publication WO 94/10137 and U.S. Ser. No. 08/346,701, incorporated herein by reference,

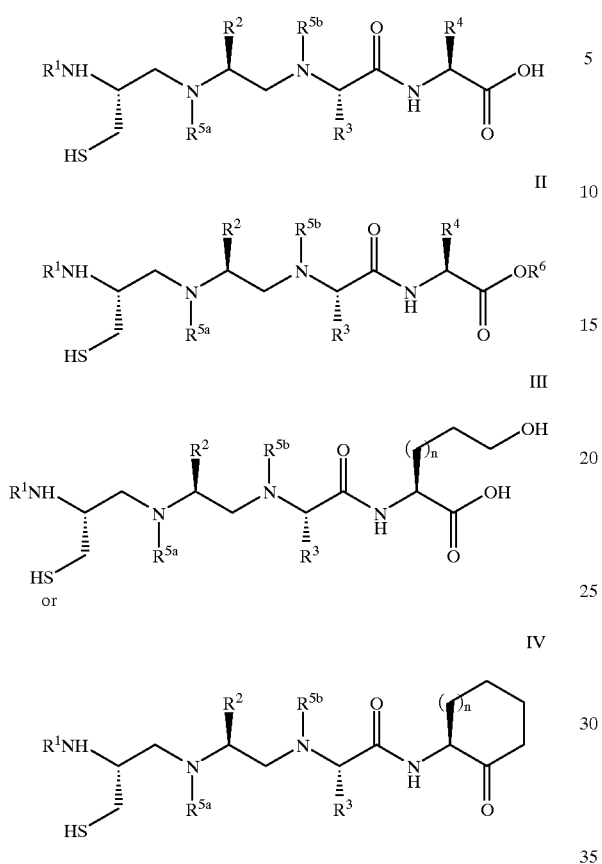

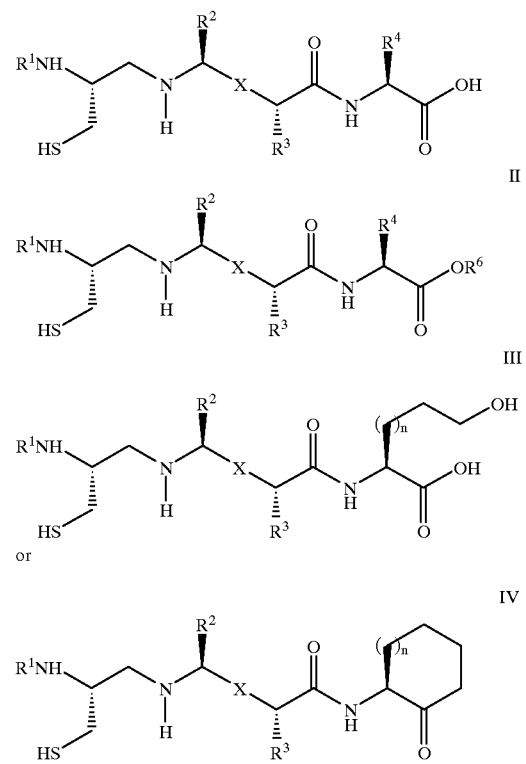

n is 0, 1 or 2;

j) PCT Publication WO 94/09766 and U.S. Ser. No. 07/968,022, incorporated herein by reference, wherein:

R$^1$ and R$^{5a}$ are independently selected from:
hydrogen, a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group
wherein the alkyl group and acyl group is optionally substituted with substituted or unsubstituted aryl or heterocycle;

R$^2$, R$^3$ and R$^4$ are independently selected from:
a) a side chain of naturally occurring amino acids,
b) an oxidized form of a side chain of naturally occurring amino acids selected from methionine sulfoxide and methionine sulfone,
c) substituted or unsubstituted C$_1$–C$_8$ alkyl, C$_3$–C$_8$ cycloalkyl, C$_2$–C$_8$ alkenyl, aryl or heterocycle groups,
wherein the aliphatic substituent is optionally substituted with an aryl, heterocycle or C$_3$–C$_8$ cycloalkyl;

R$^{5b}$ is a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group
wherein the alkyl group and acyl group is optionally substituted with substituted or unsubstituted aryl or heterocycle;

R$^6$ is a substituted or unsubstituted aliphatic, aryl or heterocyclic group, wherein the aliphatic substituent is optionally substituted with an aryl or heterocyclic ring; and wherein:

R$^1$ is selected from:
hydrogen, a C$_1$–C$_6$ alkyl group, a C$_1$–C$_6$ acyl group, an aroyl group, a C$_1$–C$_6$ alkylsulfonyl group, C$_1$–C$_6$ aralkylsulfonyl group or arylsulfonyl group
wherein the alkyl group and acyl group is optionally substituted with substituted or unsubstituted aryl or heterocycle;

R$^2$, R$^3$ and R$^4$ are independently selected from:
a) a side chain of naturally occurring amino acids,
b) an oxidized form of a side chain of naturally occurring amino acids selected from methionine sulfoxide and methionine sulfone,
c) substituted or unsubstituted C$_1$–C$_8$ alkyl, C$_3$–C$_8$ cycloalkyl, C$_2$–C$_8$ alkenyl, aryl or heterocycle groups,
wherein the aliphatic substituent is optionally substituted with an aryl, heterocycle or C$_3$–C$_8$ cycloalkyl;

X is CH$_2$CH$_2$ or trans CH=CH;

R$^6$ is a substituted or unsubstituted aliphatic, aryl or heterocyclic group, wherein the aliphatic substituent is optionally substituted with an aryl or heterocyclic ring; and n is 0, 1 or 2;

k) PCT Publication WO 94/10138 and U.S. Ser. No. 08/143,943, incorporated herein by reference,

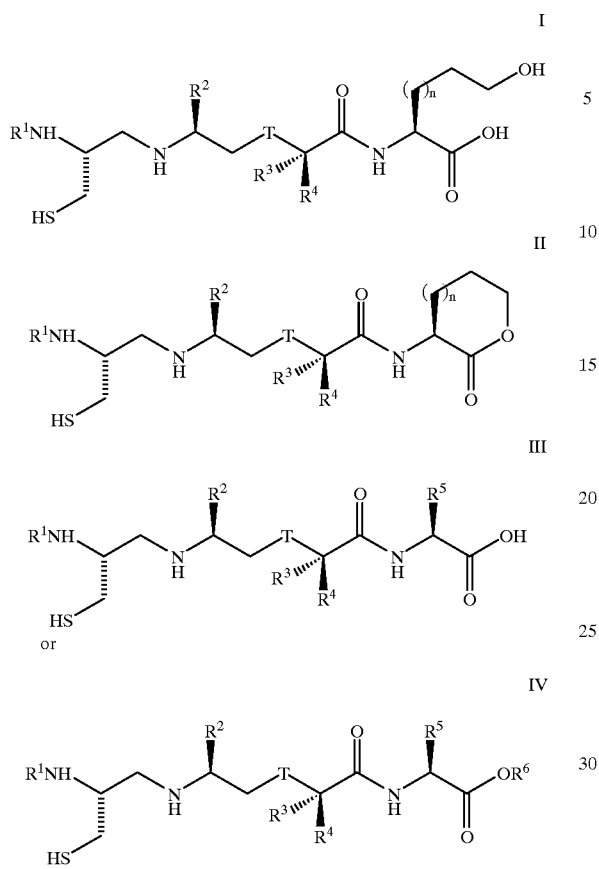

I, II, III, IV wherein,

R¹ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

R², R³ and R⁵ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

R⁴ is hydrogen or an alkyl group, wherein the alkyl group comprises straight chain or branched chain hydrocarbons of 1 to 6 carbon atoms;

R⁶ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;

T is O or S(O)$_m$;

m is 0, 1 or 2; and n is 0, 1 or 2;

1) PCT Publication WO 95/00497, incorporated herein by reference,

A, B, C wherein:

X is O or H₂;
m is 1 or 2;
n is 0 or 1;
t is 1 to 4;
R and R¹ are independently selected from H, C$_{1-4}$ alkyl, or aralkyl;
R², R³, R⁴, and R⁵ are independently selected from: H; C$_{1-8}$ alkyl, alkenyl, alkynyl, aryl, heterocycle,

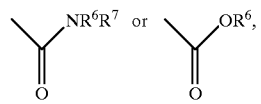

unsubstituted or substituted with one or more of:

1) aryl or heterocycle, unsubstituted or substituted with:
   a) C$_{1-4}$ alkyl,
   b) (CH₂)$_r$OR⁶,
   c) (CH₂)$_r$NR⁶ R⁷,
   d) halogen,
2) C$_{3-6}$ cycloalkyl,
3) OR⁶,
4) SR⁶, S(O)R⁶, SO₂ R⁶,

5) —NR⁶R⁷,

6) 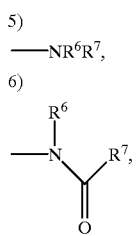

-continued

7) 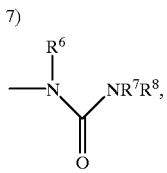

8) 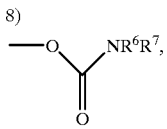

9) 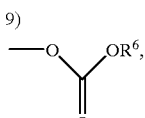

10) 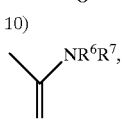

11) —SO$_2$—NR$^6$R$^7$,

12) 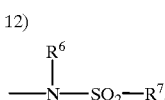

13) 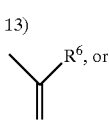

14) 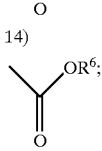

and any two of R$^2$, R$^3$, R$^4$, and R$^5$ are optionally attached to the same carbon atom;

Y is aryl, heterocycle, unsubstituted or substituted with one or more of:
1) C$_{1-4}$ alkyl, unsubstituted or substituted with:
  a) C$_{1-4}$ alkoxy,
  b) NR$^6$ R$^7$,
  c) C$_{3-6}$ cycloalkyl,
  d) aryl or heterocycle,
  e) HO,
2) aryl or heterocycle,
3) halogen,
4) OR$^6$,
5) NR$^6$ R$^7$,
6) CN,
7) NO$_2$, or
8) CF$_3$;

W is H$_2$ or O;

Z is aryl, heteroaryl, arylmethyl, heteroarylmethyl, arylsulfonyl, heteroarylsulfonyl, unsubstituted or substituted with one or more of the following:
1) C$_{1-4}$ alkyl, unsubstituted or substituted with:
  a) C$_{1-4}$ alkoxy,
  b) NR$^6$ R$^7$,
  c) C$_{3-6}$ cycloalkyl,
  d) aryl or heterocycle, or e) HO,
2) aryl or heterocycle,
3) halogen,
4) OR$^6$,
5) NR$^6$ R$^7$,
6) CN,
7) NO$_2$, or
8) CF$_3$;

R$^6$, R$^7$ and R$^8$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  a) C$_{1-4}$ alkoxy,
  b) aryl or heterocycle,
  c) halogen,
  d) HO, e) 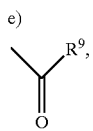

f) —SO$_2$ R$^9$ or
  g) NRR$^1$, wherein
R$^6$ and R$^7$ may be joined in a ring, and
R$^7$ and R$^8$ may be joined in a ring; and
R$^9$ is C$_{1-4}$ alkyl or aralkyl;
m) U.S. Ser. No. 08/315,059, incorporated herein by reference,

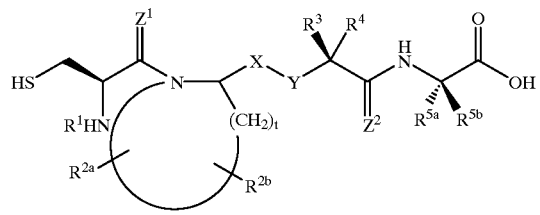

I

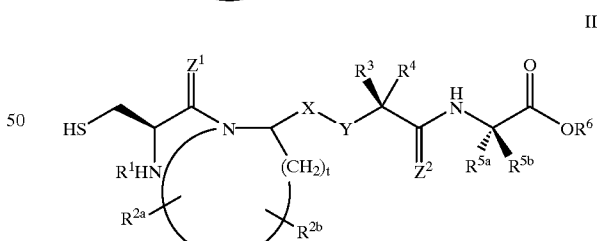

II

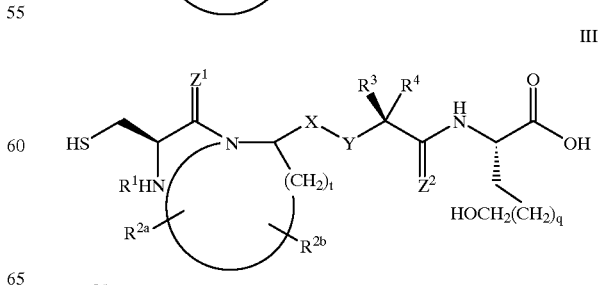

III or

IV

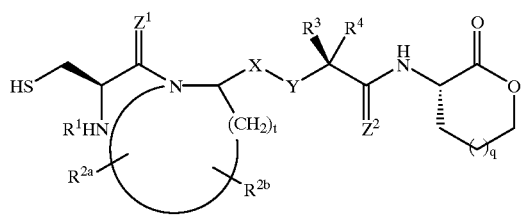

wherein:
R$^1$ is selected from:
a) hydrogen,
b) R$^8$S(O)$_2$—, R$^8$C(O)—, (R$^8$)$_2$NC(O)— or R$^9$OC(O)—, and
c) C$_1$–C$_6$ alkyl unsubstituted or substituted by aryl, heterocyclic, cycloalkyl, alkenyl, alkynyl, R$^8$O—, R$^8$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—;

R$^{2a}$ and R$^{2b}$ are independently selected from:
a) hydrogen,
b) C$_1$–C$_6$ alkyl unsubstituted or substituted by alkenyl, R$^8$O—, R$^8$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—,
c) aryl, heterocycle, cycloalkyl, alkenyl, R$^8$O—, R$^8$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—, and
d) C$_1$–C$_6$ alkyl substituted with an unsubstituted or substituted group selected from aryl, heterocyclic and C$_3$–C$_{10}$ cycloalkyl;

R$^3$ and R$^4$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted C$_1$–C$_{20}$ alkyl, C$_2$–C$_{20}$ alkenyl, C$_3$–C$_{10}$ cycloalkyl, aryl or heterocyclic group, wherein the substituent is selected from F, Cl, Br, N(R$^8$)$_2$, NO$_2$, R$^8$O—, R$^8$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
d) C$_1$–C$_6$ alkyl substituted with an unsubstituted or substituted group selected from aryl, heterocyclic and C$_3$–C$_{10}$ cycloalkyl; or
R$^3$ and R$^4$ are combined to form —(CH$_2$)$_s$—;

R$^{5a}$ and R$^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted C$_1$–C$_{20}$ alkyl, C$_2$–C$_{20}$ alkenyl, C$_3$–C$_{10}$ cycloalkyl, aryl or heterocycle group, wherein the substituent is selected from F, Cl, Br, N(R$^8$)$_2$, NO$_2$, R$^8$O—, R$^8$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
d) C$_1$–C$_6$ alkyl substituted with an unsubstituted or substituted group selected from aryl, heterocyclic and C$_3$–C$_{10}$ cycloalkyl; or R$^{5a}$ and R$^{5b}$ are combined to form —(CH$_2$)$_s$— wherein one of the carbon atoms is optionally replaced by a moiety selected from: O, S(O)$_m$, —NC(O)—, and —N(COR$^8$)—;

R$^6$ is
a) substituted or unsubstituted C$_1$–C$_8$ alkyl, wherein the substituent on the alkyl is selected from:
1) aryl,
2) heterocycle,
3) —N(R$^9$)$_2$,
4) —OR$^8$, or
b)

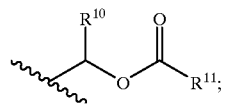

X—Y is
a)

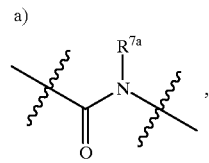

b)

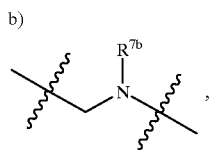

c)

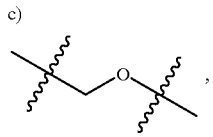

d)

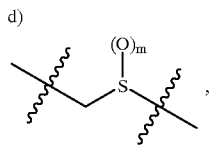

e)

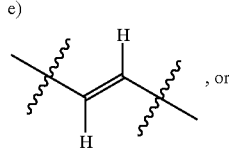

, or f)
—CH$_2$—CH$_2$—;

R$^{7a}$ is selected from
a) hydrogen,
b) unsubstituted or substituted aryl,
c) unsubstituted or substituted heterocycle,
d) unsubstituted or substituted cycloalkyl, and
e) C$_1$–C$_6$ alkyl substituted with hydrogen or an unsubstituted or substituted group selected from aryl, heterocycle and cycloalkyl;

R$^{7b}$ is selected from
a) hydrogen,
b) unsubstituted or substituted aryl,
c) unsubstituted or substituted heterocycle,
d) unsubstituted or substituted cycloalkyl,
e) C$_1$–C$_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

$R^{11}$ is independently selected from $C_1$–$C_6$ alkyl;

$Z^1$ and $Z^2$ are independently $H_2$ or O, provided that $Z^1$ is not O when

X-Y is —C(O)N($R^{7a}$)—;

m is 0, 1 or 2;

q is 0, 1 or 2;

s is 4 or 5; and t is 3, 4 or 5;

n) U.S. Ser. No. 08/315,151, incorporated herein by reference,

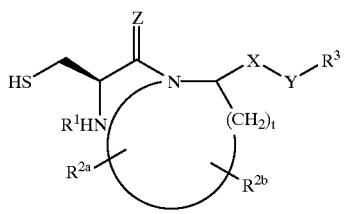

I wherein:

$R^1$ is selected from:

a) hydrogen, b) $R^5S(O)_2$—, $R^5C(O)$—, $(R^5)_2NC(O)$— or $R^6OC(O)$—, and c) $C_1$–$C_6$ alkyl unsubstituted or substituted by aryl, heterocyclic, cycloalkyl, alkenyl, alkynyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—;

$R^{2a}$ and $R^{2b}$ are independently selected from:

a) hydrogen, b) $C_1$–$C_6$ alkyl unsubstituted or substituted by aryl, heterocycle, cycloalkyl, alkenyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—, and c) aryl, heterocycle, cycloalkyl, alkenyl, $R^5O$—, $R^5S(O)_m$—, $R^5C(O)NR^5$—, CN, $NO_2$, $(R^5)_2N$—$C(NR^5)$—, $R^5C(O)$—, $R^5OC(O)$—, $N_3$, —$N(R^5)_2$, or $R^6OC(O)NR^5$—, $R^3$ is selected from:

a) unsubstituted or substituted aryl, b) unsubstituted or substituted heterocycle, c) unsubstituted or substituted cycloalkyl, and d) $C_1$–$C_6$ alkyl substituted with hydrogen or an unsubstituted or substituted group selected from aryl, heterocycle and cycloalkyl;

X-Y is a)

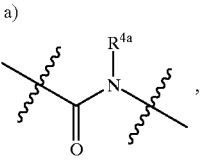

b)

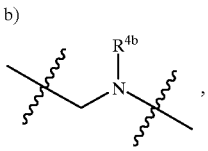

c)

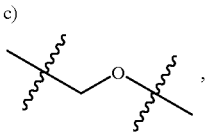

d)

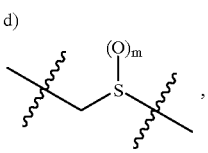

e)

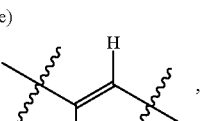

, or f)

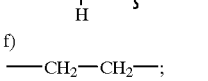

—$CH_2$—$CH_2$—;

$R^{4a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

$R^{4b}$ is selected from a) hydrogen, b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^5$ is independently selected from hydrogen, $C_1$–$C_6$ alkyl and aryl;

$R^6$ is independently selected from $C_1$–$C_6$ alkyl and aryl;
Z is independently $H_2$ or O;
m is 0, 1 or 2, provided that m is 0 when $R^5$=hydrogen;
n is 0, 1, 2, 3 or 4; and
t is 3, 4 or 5;
and
p) U.S. Ser. No. 08/412,621 (Case 19384IA, filed Jun. 6, 1995), incorporated herein by reference,

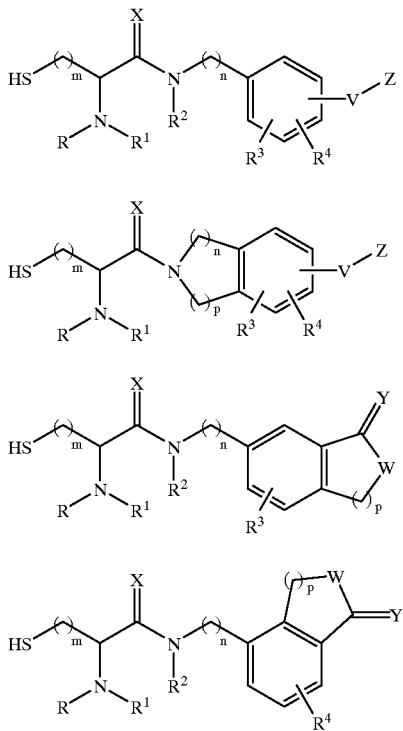

wherein:
X and Y are independently O or $H_2$;
m is 1 or 2;
n is 0 or 1;
p is 1, 2 or 3;
q is 0, 1 or 2;
t is 1 to 4;
R, $R^1$ and $R^2$ are independently selected from: H, $C_{1-6}$ alkyl, or $C_{1-6}$ aralkyl;
$R^3$ and $R^4$ are independently selected from:
  a) hydrogen,
  b) $C_1$–$C_6$ alkyl unsubstituted or substituted by $C_2$–$C_6$ alkenyl, $R^6O$—, $R^5S(O)_q$—, $R^7C(O)NR^6$—, CN, $N_3$, $R^6OC(O)NR^6$—, $R^6 R^7N$—$C(NR^6 R^8)$—, $R^6C(O)'$, $R^7 R^8NC(O)O$—, $R^7 R^8NC(O)$—, $R^6 R^7N$—$S(O)_2$—, —$NR^6S(O)_2 R^5$, $R^6OC(O)O$—, —$NR^6 R^7$, or $R^7 R^8NC(O)NR^6$—,
  c) unsubstituted or substituted cycloalkyl, alkenyl, $R^6O$—, $R^5S(O)_q$—, $R^6C(O)NR^6$—, CN, $NO_2$, $R^6 R^7N$—$C(NR^8)$—, $R^6C(O)$—, $N_3$, —$NR^6 R^7$, halogen or $R^7OC(O)NR^6$—, and
  d) $C_1$–$C_6$ alkyl substituted with an unsubstituted or substituted group selected from aryl, heterocyclic and $C_3$—$C_{10}$ cycloalkyl;
W is —$CHR^9$— or —$NR^9$—;
Z is unsubstituted or substituted $C_{1-8}$ alkyl, unsubstituted or substituted $C_{2-8}$ alkenyl, unsubstituted or substituted aryl, unsubstituted or substituted heterocycle;

wherein the substituted group is substituted with one or more of:
  1) $C_{1-4}$ alkyl, unsubstituted or substituted with:
    a) $C_{1-4}$ alkoxy,
    b) $NR^6 R^7$,
    c) $C_{3-6}$ cycloalkyl,
    d) aryl or heterocycle,
    e) HO,
  2) aryl or heterocycle,
  3) halogen,
  4) $OR^6$,
  5) $NR^6 R^7$,
  6) CN,
  7) $NO_2$, or
  9) $CF_3$;
$R^5$ is $C_{1-4}$ alkyl or aralkyl;
$R^6$, $R^7$ and $R^8$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO, e) 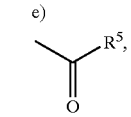

f) —$SO_2 R^5$, or
  g) —$NR^6 R^7$, or
$R^6$ and $R^7$ may be joined in a ring, and $R^7$ and $R^8$ may be joined in a ring;
$R^9$ is selected from: H, $C_{1-4}$ alkyl, $C_{3-6}$ cycloalkyl, heterocycle and aryl, unsubstituted, monosubstituted or disubstituted with substituents independently selected from:
  a) $C_{1-4}$ alkyl,
  b) $C_{1-4}$ alkoxy,
  c) aryl or heterocycle,
  d) halogen,
  e) HO, f) 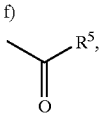

g) —$SO_2 R^5$, and
  h) —$NR^6 R^7$;
V is selected from: —$C(R^{11})$=$C(R^{11})$—, —C≡C—, —C(O)—, —$C(R^{11})_2$—, —$C(OR^{11})R^{11}$—, —$CN(R^{11})_2 R^{11}$—, —$OC(R^{11})^2$—, —$NR^{11}C(R^{11})^2$—, —$C(R^{11})_2O$—, —$C(R^{11})_2NR^{11}$—, —$C(O)NR^{11}$—, —$NR^{11}C(O)$—, O, —$NC(O)R^{11}$—, —$NC(O)OR^{11}$—, —$S(O)_{2-N(R^{11})}$—, —$N(R^{11})S(O)_2$—, or $S(O)_m$;
$R^{10}$ and $R^{11}$ are independently selected from hydrogen, $C_1$–$C_6$ alkyl, $C_2$–$C_4$ alkenyl, benzyl and aryl;
or the pharmaceutically acceptable salt thereof.

The composition of the instant invention may alternatively or in addition comprise a protein substrate-competitive inhibitor that does not incorporates a cysteinyl or sulfhydryl containing moiety at the N-terminus of the molecule. The lack of a sulfhydryl offers unique advantages in terms of improved pharmacokinetic behavior in animals, prevention of thiol-dependent chemical reactions, such as rapid autoxidation and disulfide formation with endogenous thiols, and reduced systemic toxicity. Thus the following compounds, well known in the art, are also useful as protein substrate-competitive inhibitors in the instant invention:

q) PCT Publication WO 95/09001 and U.S. Ser. No. 08/314,987, incorporated herein by reference,

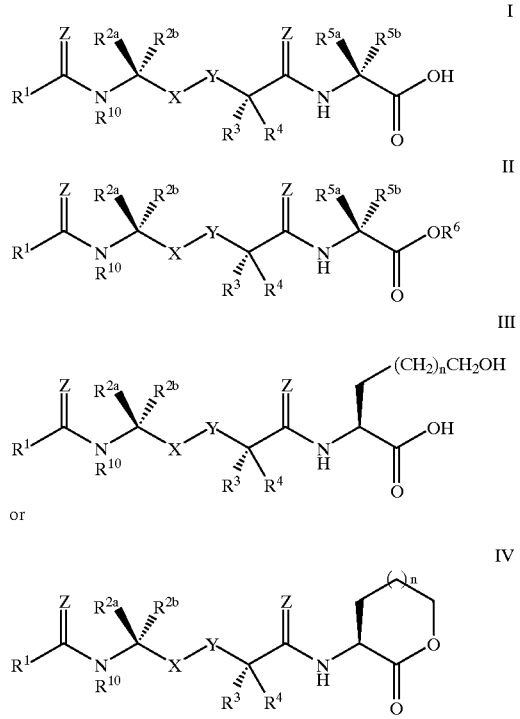

$R^1$ is selected from:
 a) heterocycle, and
 b) $C_1$–$C_{10}$ alkyl, which is substituted with heterocycle and which is optionally substituted with one or more of $C_1$–$C_4$ alkyl, hydroxy or amino groups;

$R^{2a}$ and $R^{2b}$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl; or $R^{2a}$ and $R^{2b}$ are combined to form —$(CH_2)_2$—;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone, and
 c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^8)_2$, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl,, and
 d) $C_1$–$C_6$ alkyl substituted with an unsubstituted or substituted group selected from aryl, heterocyclic and $C_3$–$C_{10}$ cycloalkyl; or $R^3$ and $R^4$ are combined to form —$(CH_2)_2$—;

$R^{5a}$ and $R^{5b}$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $N(R^8)_2$, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
 d) $C_1$–$C_6$ alkyl substituted with an unsubstituted or substituted group selected from aryl, heterocyclic and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^8)$—;

$R^6$ is
 a) substituted or unsubstituted $C_1$–$C_8$ alkyl, wherein the substituent on the alkyl is selected from:
  1) aryl,
  2) heterocycle,
  3) —$N(R^9)_2$,
  4) —$OR^8$, or
 b)

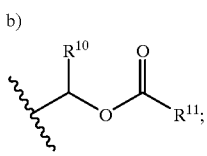

X—Y is
a)

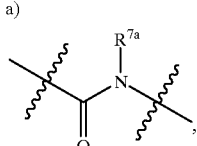

b)

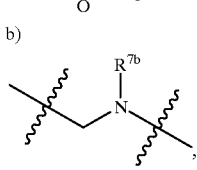

c)

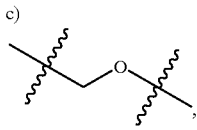

-continued d) 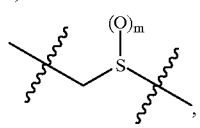

e) 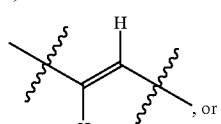, or f) 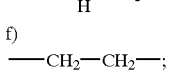

f) —CH$_2$—CH$_2$—;

R$^{7a}$ is selected from
a) hydrogen,
b) unsubstituted or substituted aryl,
c) unsubstituted or substituted heterocyclic,
d) unsubstituted or substituted cycloalkyl, and
e) C$_1$–C$_6$ alkyl substituted with hydrogen or an unsubstituted or substituted group selected from aryl, heterocyclic and cycloalkyl;

R$^{7b}$ is selected from
a) hydrogen,
b) unsubstituted or substituted aryl,
c) unsubstituted or substituted heterocyclic,
d) unsubstituted or substituted cycloalkyl,
e) C$_1$–C$_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from hydrogen, C$_1$–C$_6$ alkyl and aryl;
R$^9$ is independently selected from C$_1$–C$_6$ alkyl and aryl;
R$^{10}$ is independently selected from hydrogen and C$_1$–C$_6$ alkyl;
R$^{11}$ is independently selected from C$_1$–C$_6$ alkyl;
Z is independently H$_2$ or O;
m is 0, 1 or 2;
n is 0, 1 or 2; and
s is 4 or 5;
r) PCT Publication WO 95/09000 and U.S. Ser. No. 08/143,943, incorporated herein by reference, I
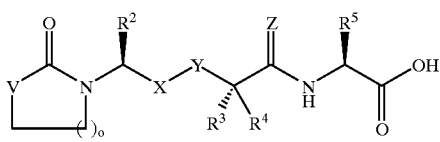

II
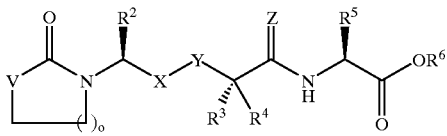

III
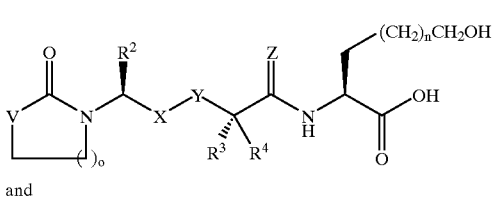

and

IV
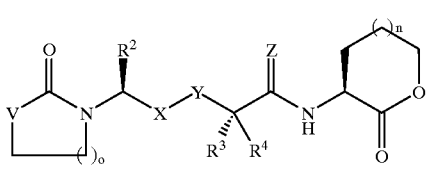

wherein:

V is CH$_2$, O, S, HN, or R$^7$N;

R$^2$, R$^3$, R$^4$ and R$^5$ are independently the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X-Y is a) 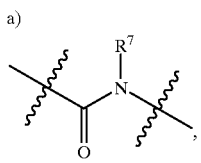

b) 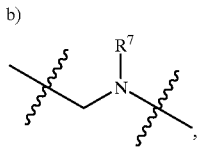

c) 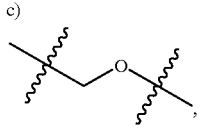

d) 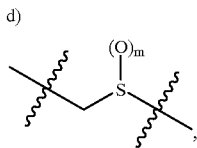

-continued e)
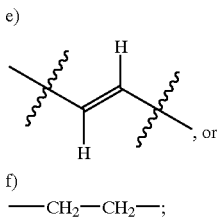, or f)
—CH$_2$—CH$_2$—;

R$^6$ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;

R$^7$ is an alkyl group, wherein the alkyl group comprises straight chain or branched chain hydrocarbons of 1 to 6 carbon atoms, which may be substituted with an aromatic or heteroaromatic group;

Z is H2 or O;

m is 0, 1 or 2;

n is 0, 1 or 2; and o is 0, 1, 2 or 3;

s) U.S. Ser. No. 08/315,171, incorporated herein by reference,

R$^{1b}$ is independently selected from:
a) hydrogen,
b) unsubstituted or substituted aryl, cycloalkyl, alkenyl, alkynyl, (R$^{10}$)$_2$N—C(NR$^{10}$)—, R$^{11}$OC(O)—, or R$^{10}$OC(O)—, and
c) C$_1$–C$_6$ alkyl unsubstituted or substituted by unsubstituted or substituted aryl, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

provided that Rib is not R$^{10}$C(O)NR$^{10}$— when R$^{1a}$ is alkenyl, V is hydrogen and X-Y is —C(O)NR$^{7a}$—;

R$^{2a}$ and R$^{2b}$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted C$_1$–C$_{20}$ alkyl, C$_2$–C$_{20}$ alkenyl, C$_3$–C$_{10}$ cycloalkyl, aryl or heterocyclic group, wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, R$^{11}$OC(O)NR$^{10}$— and C$_1$–C$_{20}$ alkyl, nd
d) C$_1$–C$_6$ alkyl substituted with an unsubstituted or substituted group selected from aryl, heterocycle and C$_3$–C$_{10}$ cycloalkyl; or

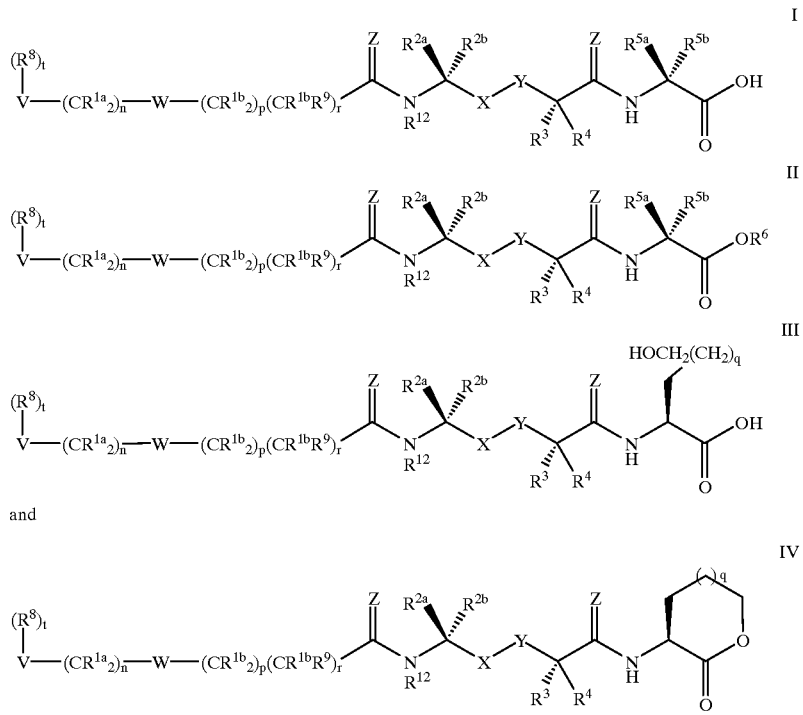

wherein:

R$^{1a}$ is selected from:
a) hydrogen,
b) aryl, heterocyclic, cycloalkyl, alkenyl, alkynyl, (R$^{10}$)$_2$N—C(NR$^{10}$)—, R$^{10}$C(O)—, or R$^{10}$OC(O)—, and
c) C$_1$–C$_6$ alkyl unsubstituted or substituted by aryl, heterocyclic, cycloalkyl, alkenyl, alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{2a}$ and R$^{2b}$ are combined to form —(CH$_2$)$_2$—;

R$^3$ and R$^4$ are independently selected from:
a) a side chain of a naturally occurring amino acid,
b) an oxidized form of a side chain of a naturally occurring amino acid which is:
 i) methionine sulfoxide, or
 ii) methionine sulfone,
c) substituted or unsubstituted C$_1$–C$_{20}$ alkyl, C$_2$–C$_{20}$ alkenyl, C$_3$–C$_{10}$ cycloalkyl, aryl or heterocyclic group, wherein the substituent is selected from F, Cl, Br, $N(R^{10})_2$, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}C(O)—$, $N_3$, $—N(R^{10})_2$, $R^{11}OC(O)NR^{10}—$ and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^3$ and $R^4$ are combined to form $—(CH_2)_2—$;

$R^{5a}$ and $R^{5b}$ independently selected from:

a) a side chain of a naturally occurring amino acid, b) an oxidized form of a side chain of a naturally occurring amino acid which is:
  i) methionine sulfoxide, or
  ii) methionine sulfone, c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $NO_2$, $R^{10}O—$, $R^{11}S(O)_m—$, $R^{10}C(O)NR^{10}—$, CN, $(R^{10})_2N—C(NR^{10})—$, $R^{10}C(O)—$, $R^{10}OC(O)—$, $N_3$, $—N(R^{10})_2$, $R^{11}OC(O)NR^{10}—$ and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form $—(CH_2)_s—$ wherein one of the carbon atoms is optionally replaced by a moiety selected from: O, $S(O)_m$, $—NC(O)—$, and $—N(COR^{10})—$;

$R^6$ is a) substituted or unsubstituted $C_1$–$C_8$ alkyl, wherein the substituent on the alkyl is selected from:
  1) aryl,
  2) heterocycle,
  3) $—N(R^{11})_2$,
  4) $-OR^{10}$, or b)

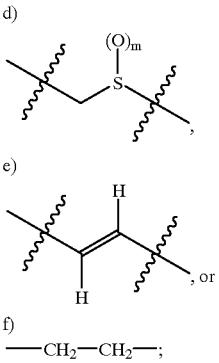

X—Y is a)

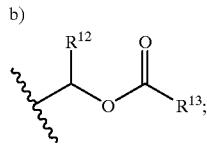

b)

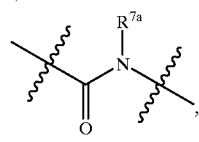

c)

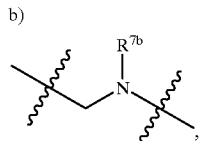

d)

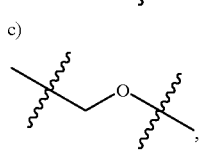

e)

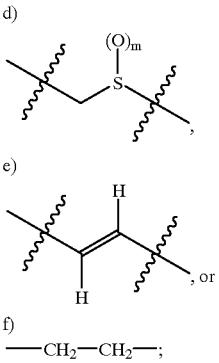

, or f)
$—CH_2—CH_2—$;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
  a) hydrogen,
  b) aryl, heterocyclic, cycloalkyl, alkenyl, alkynyl, perfluoroalkyl, F, Cl, Br, $R^{10}O—$, $R^{11}S(O)_m—$, $R^{10}C(O)NR^{10}—$, CN, $NO_2$, $R^{10}_2N—C(NR^{10})—$, $R^{10}C(O)—$, $R^{10}OC(O)—$, $N_3$, $—N(R^{10})_2$, or $R^{11}OC(O)NR^{10}—$, and
  c) $C_1$–$C_6$ alkyl unsubstituted or substituted by aryl, heterocyclic, cycloalkyl, alkenyl, alkynyl, perfluoroalkyl, F, Cl, Br, $R^{10}O—$, $R^{11}S(O)_m—$, $R^{10}C(O)NH—$, CN, $H_2N—C(NH)—$, $R^{10}C(O)—$, $R^{10}OC(O)—$, $N_3$, $—N(R^{10})_2$, or $R^{11}OC(O)NH—$;

$R^9$ is selected from: hydrogen, $C_1$–$C_6$ alkyl, $R^{10}O—$, $R^{11}S(O)_m—$, $R^{10}C(O)NR^{10}—$, CN, $NO_2$, $N_3$, $—N(R^{10})_2$, nd $R^{11}OC(O)NR^{10}—$;

provided that $R^9$ is not $R^{10}C(O)NR^{10}—$ when $R^{1a}$ is alkenyl, V is hydrogen and X-Y is $—C(O)NR^{7a}—$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen and $C_1$–$C_6$ alkyl;

$R^{13}$ is $C_1$–$C_6$ alkyl;

V is selected from:
a) aryl;
b) heterocycle; or
c) hydrogen;

W is —S(O)$_m$—, —O—, —NHC(O)—, —C(O)NH—, —NHSO$_2$—, —SO$_2$NH—, —N($R^{7a}$)— or —N[C(O)$R^{7a}$]—;

Z is independently H$_2$ or O;

m is 0, 1 or 2;

n is 0, 1, 2, 3 or 4, provided that n≠0 when V is hydrogen and W is —S(O)$_m$—;

p is 0, 1, 2, 3 or 4, provided that p≠0 when $R^9$ is not hydrogen or $C_1$–$C_6$ lower alkyl;

q is , 1 or 2;

r is 0 or 1;;

s is 4 or 5; and t is 0, 1 or 2, provided that t=0 when V is hydrogen;

t) U.S. Ser. No. 08/315,046, incorporated herein by reference, $R^{2a}$ and $R^{2b}$ are combined to form —(CH$_2$)$_2$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, NO$_2$, $R^9$O—, $R^{10}$S(O)$_m$—, $R^9$C(O)NR$^9$—, CN, (R$^9$)$_2$N—C(NR$^9$)—, $R^9$C(O)—, $R^9$OC(O)—, N$_3$, —N(R$^9$)$_2$, $R^{10}$OC(O)NR$^9$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^3$ and $R^4$ are combined to form —(CH$_2$)$_s$—;

$R^{5a}$ and $R^{5b}$ are independently selected from:
a) a side chain of a naturally occurring amino acid,
b) an oxidized form of a side chain of a naturally occurring amino acid which is:

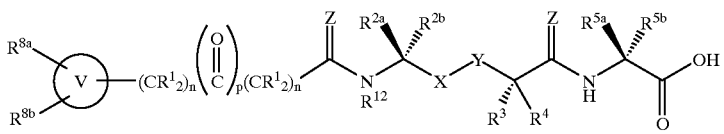

I

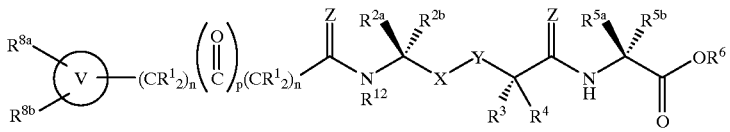

II

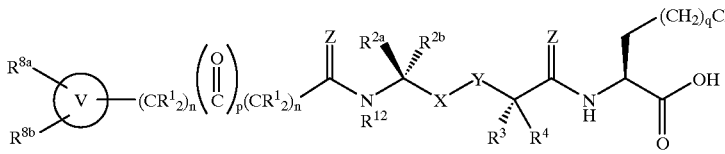

III and

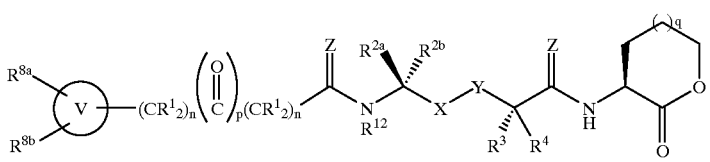

IV wherein:

$R^1$ is hydrogen, $C_1$–$C_6$ alkyl or aryl;

$R^{2a}$ and $R^{2b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, NO$_2$, $R^9$O—, $R^{10}$S(O)$_m$—, $R^9$C(O)NR$^9$—, CN, (R$^9$)$_2$N—C(NR$^9$)—, $R^9$C(O)—, $R^9$OC(O)—, N$_3$, —N(R$^9$)$_2$, $R^{10}$OC(O)NR$^9$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, NO$_2$, $R^9$O—, $R^{10}$S(O)$_m$—, $R^9$C(O)NR$^9$—, CN, (R$^9$)$_2$N—C(NR$^9$)—, $R^9$C(O)—, $R^9$OC(O)—, N$_3$, —N(R$^9$)$_2$, $R_{10}$OC(O)NR$^9$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —(CH$_2$)$_s$— wherein one of the carbon atoms is optionally replaced by a moiety selected from: O, S(O)$_m$, —NC(O)—, and —N(COR$^9$)—;

$R^6$ is
a) substituted or unsubstituted $C_1$–$C_8$ alkyl, wherein the substituent on the alkyl is selected from:

1) aryl,
2) heterocycle,
3) —N(R$^{10}$)$_2$,
4) —O R$^9$, or b)
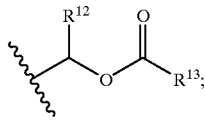

X—Y is a)
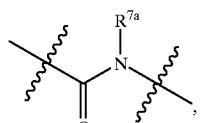

b)
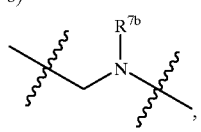

c)
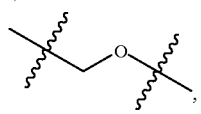

d)
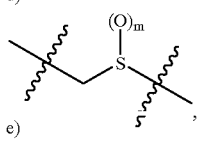

e)
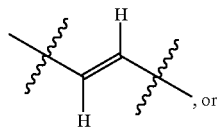

f)
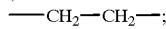
—CH$_2$—CH$_2$—;

R$^{7a}$ is selected from
a) hydrogen,
b) unsubstituted or substituted aryl,
c) unsubstituted or substituted heterocycle,
d) unsubstituted or substituted cycloalkyl, and
e) C$_1$–C$_6$ alkyl substituted with hydrogen or an unsubstituted or substituted group selected from aryl, heterocycle and cycloalkyl;

R$^{7b}$ is selected from
a) hydrogen,
b) unsubstituted or substituted aryl,
c) unsubstituted or substituted heterocycle,
d) unsubstituted or substituted cycloalkyl,
e) C$_1$–C$_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and C$_1$–C$_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and C$_1$–C$_6$ alkyl substituted with hydrogen or an unsubstituted or substituted group selected from aryl, heterocycle and cycloalkyl;

R$^{8a}$ and R$^{8b}$ are independently selected from:
hydrogen, F, Cl, Br, NO$_2$, R$^{11}$O, R$^{10}$S(O)$_m$—, CN, R$^9$C(O)NR$^9$—, (R$^9$)$_2$N—C(NR$^9$)—, R$^9$C(O)—, R$^9$OC(O)—, N$_3$, —N(R$^9$)$_2$, R$^{10}$OC(O)NR$^9$—, C$_1$–C$_{20}$ alkyl, aryl, heterocycle or C$_1$–C$_{20}$ alkyl substituted with aryl or heterocycle;

R$^9$ is independently selected from hydrogen, C$_1$–C$_6$ alkyl and aryl;

R$^{10}$ is independently selected from C$_1$–C$_6$ alkyl and aryl;

R$^{11}$ is independently selected from hydrogen, C$_1$–C$_6$ alkyl and aryl, provided R$^{11}$ is C$_1$–C$_6$ alkyl when n is O;

R$^{12}$ is independently hydrogen or C$_1$–C$_6$ alkyl;

R$^{13}$ is C$_1$–C$_6$ alkyl; V is aryl or 1,2,3,4-tetrahydronaphthyl;

Z is independently H$_2$ or O;

m is 0, 1 or 2;

n is independently 0 to 4;

p is 0 or 1;

q is 0, 1 or 2; and s is 4 or 5;

u) U.S. Ser. No. 08/314,974, incorporated herein by reference,

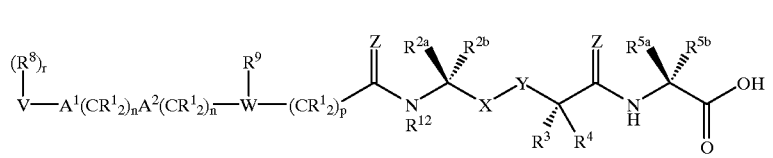

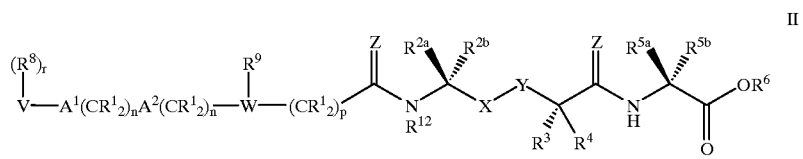

-continued

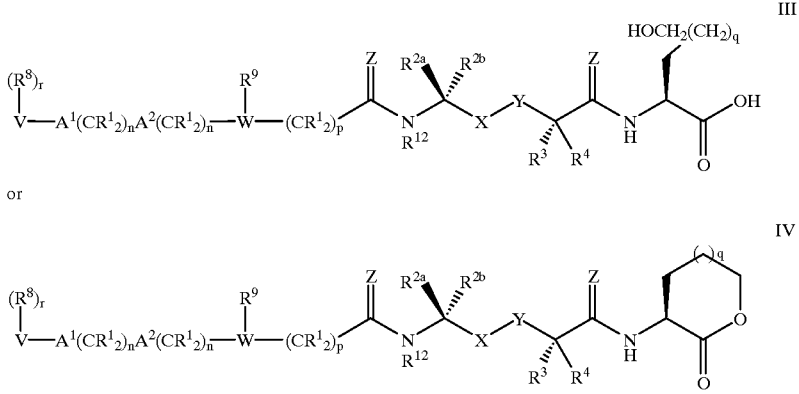

wherein:

R¹ is independently selected from:
a) hydrogen,
b) aryl, heterocyclic, cycloalkyl, alkenyl, alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^{2a}$ and $R^{2b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{2a}$ and $R^{2b}$ are combined to form $-(CH_2)_2-$;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^3$ and $R^4$ are combined to form $-(CH_2)_2-$;

$R^{5a}$ and $R^{5b}$ are independently selected from:

a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or $R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^{10})-$;

$R^6$ is
a) substituted or unsubstituted $C_1-C_8$ alkyl, wherein the substituent on the alkyl is selected from:
  1) aryl,
  2) heterocycle,
  3) $-N(R^{11})_2$,
  4) $-OR^{10}$, or b)
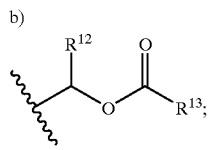

X—Y is
a)
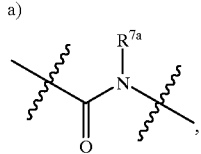

b)
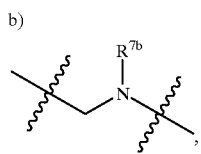

-continued

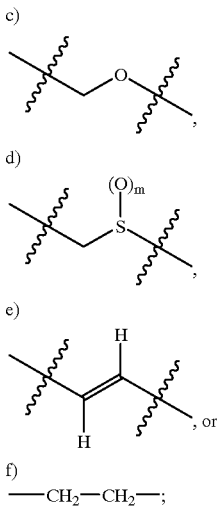

c)

d)

e)

, or f) —CH$_2$—CH$_2$—;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from:
  a) hydrogen,
  b) aryl, heterocyclic, cycloalkyl, alkenyl, alkynyl, perfluoroalkyl, F, Cl, Br, $R^{10}O$—, $R^{11}S(O)_m$—, $R^{10}C(O)NR^{10}$—, CN, NO$_2$, $R^{10}{}_2N$—C(NR$^{10}$)—, $R^{10}C(O)$—, $R^{10}OC(O)$—, N$_3$, —N(R$^{10}$)$_2$, or $R^{11}OC(O)NR^{10}$—, and
  c) $C_1$–$C_6$ alkyl unsubstituted or substituted by aryl, heterocyclic, cycloalkyl, alkenyl, alkynyl, perfluoroalkyl, F, Cl, Br, $R^{10}O$—, $R^{11}S(O)_m$—, $R^{10}C(O)NH$—, CN, H$_2$N—C(NH)—, $R^{10}C(O)$—, $R^{10}OC(O)$—, N$_3$, —N(R$^{10}$)$_2$, or $R^{11}OC(O)NH$—;

$R^9$ is selected from:
  a) hydrogen,
  b) alkenyl, alkynyl, perfluoroalkyl, F, Cl, Br, $R^{10}O$—, $R^{11}S(O)_m$—, $R^{10}C(O)NR^{10}$—, CN, NO$_2$,(R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—, and
  c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, N, (R$^{10}$)$_2$N—C(NR$^{10}$)—, $R^{10}C(O)$—, $R^{10}OC(O)$—, N$_3$, —N(R$^{10}$)$_2$, or $R^{11}OC(O)NR^{10}$—;

$R^{10}$ is independently selected from hydrogen, $C_1$–$C_6$ alkyl and aryl;
$R^{11}$ is independently selected from $C_1$–$C_6$ alkyl and aryl;
$R^{12}$ is independently selected from hydrogen and $C_1$–$C_6$ alkyl;
$R^{13}$ is independently selected from $C_1$–$C_6$ alkyl;
$A^1$ and $A^2$ are independently selected from: a bond, —CH=CH—, —C≡C—, —C(O)—, —C(O)NR$^{10}$—, O, —N(R$^{10}$)—, —NR$^{10}$C(O)—, —S(O)$_2$N(R$^{10}$)—, —N(R$^{10}$)S(O)$_2$— or S(O)$_m$;

V is selected from:
  a) hydrogen,
  b) heterocycle,
  c) aryl,
  d) $C_1$–$C_{20}$ alkyl wherein from 0 to 4 non-terminal carbon atoms are replaced with a a heteroatom selected from O, S, and N, and
  e) $C_2$–$C_{20}$ alkenyl;
provided that V is not hydrogen if $A^1$ is S(O)$_m$ and V is not hydrogen if $A^1$ is a bond, n is 0 and $A^2$ is S(O)$_m$ or a bond;

W is a heterocycle;
Z is independently H$_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen; and
s is 4 or 5;
v) U.S. Ser. Nos. 08/315,161 and 08/399,282 (Case 19308IB, filed Jun. 6, 1995), incorporated herein by reference,

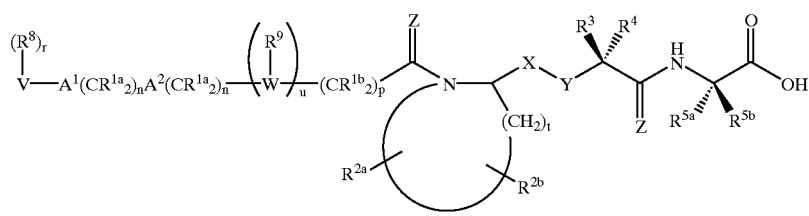

I

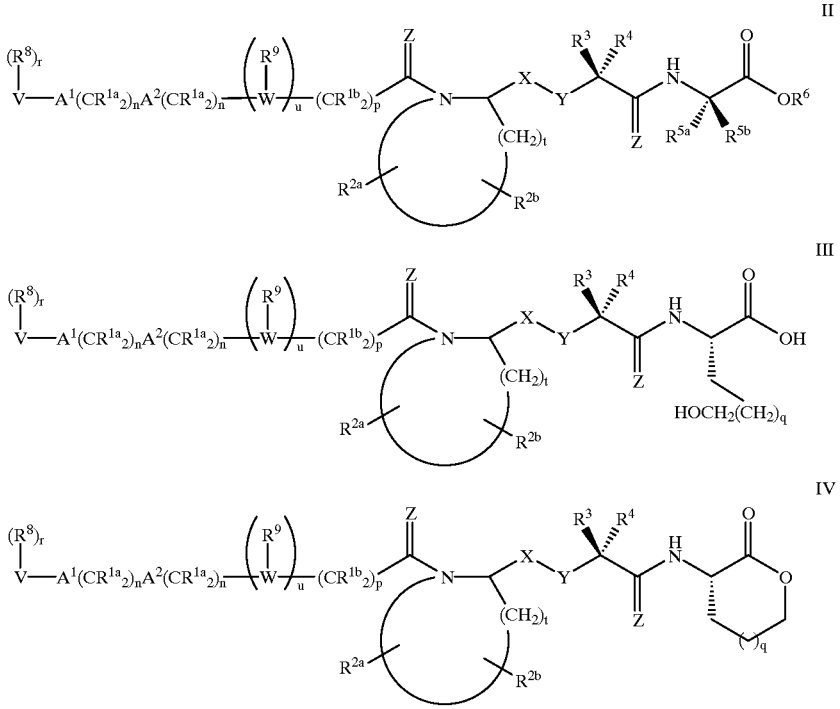

wherein:

$R^{1a}$ and $R^{2b}$ are independently selected from:
 a) hydrogen,
 b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
 c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)$—$NR^{10}$—;

$R^{2a}$ and $R^{2b}$ are independently selected from:
 a) hydrogen,
 b) $C_1$–$C_6$ alkyl unsubstituted or substituted by $C_2$–$C_6$ alkenyl, $R^{10}O$—, $R^{11}S(O)_m$—, $R^{10}C(O)NR^{10}$—, CN, $N_3$,$(R^{10})_2N$—$C(NR^{10})$—, $R^{10}C(O)$—, $R^{10}OC(O)$—, —$N(R^{10})_2$, or $R^{11}OC(O)NR^{10}$—,
 c) aryl, heterocycle, $C_3$–$C_{10}$ cycloalkyl, $C_2$–$C_6$ alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
 d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^{10})_2$, $NO_2$, $R^{10}O$—, $R^{11}S(O)_m$—, $R^{10}C(O)$ $NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl; or $R^3$ and $R^4$ are combined to form —$(CH_2)_2$—;

$R^{5a}$ and $R^{5b}$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $CF_3$, $N(R^{10})_2$, $NO_2$, $R^{10}O$—, $R^{11}S(O)_m$—, $R^{10}C(O)$ $NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and
 d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —NC(O)—, and —$N(COR^{10})$—;

$R^6$ is
 a) substituted or unsubstituted $C_1$–$C_8$ alkyl, substituted or unsubstituted $C_5$–$C_8$ cycloalkyl, or substituted or unsubstituted cyclic amine, wherein the substituted alkyl, cycloalkyl or cyclic amine is substituted with 1 or 2 substituents independently selected from:
  1) $C_1$–$C_6$ alkyl,
  2) aryl,
  3) heterocycle, 4) —N(R$^{11}$)$_2$,
5) —OR$^{10}$, or b) 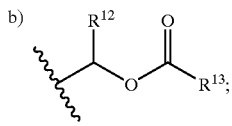

X—Y is a) 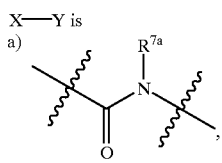

b) 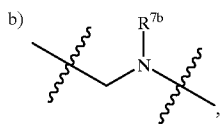

c) 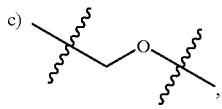

d) 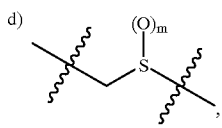

e) 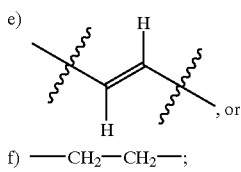, or f) —CH$_2$—CH$_2$—;

R$^{7a}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl, and
  e) C$_1$–C$_6$ alkyl substituted with hydrogen or an unsubstituted or substituted group selected from aryl, heterocycle and C$_3$–C$_{10}$ cycloalkyl;

R$^{7b}$ is selected from
  a) hydrogen,
  b) unsubstituted or substituted aryl,
  c) unsubstituted or substituted heterocycle,
  d) unsubstituted or substituted C$_3$–C$_{10}$ cycloalkyl,
  e) C$_1$–C$_6$ alkyl substituted with hydrogen or an unsubstituted or substituted group selected from aryl, heterocycle and C$_3$–C$_{10}$ cycloalkyl,
  f) a carbonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl, and
  g) a sulfonyl group which is bonded to an unsubstituted or substituted group selected from aryl, heterocycle, C$_3$–C$_{10}$ cycloalkyl and C$_1$–C$_6$ alkyl substituted with hydrogen or an unsubstituted or substituted group selected from aryl, heterocycle and C$_3$–C$_{10}$ cycloalkyl;

R$^8$ is independently selected from:
  a) hydrogen,
  b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, R$^{10}{}_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

R$^9$ is selected from:
  a) hydrogen,
  b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^1$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from H, C$_1$–C$_6$ alkyl, benzyl, substituted aryl and C$_1$–C$_6$ alkyl substituted with substituted aryl;

R$^{11}$ is independently selected from C$_1$–C$_6$ alkyl and aryl;

R$^{12}$ is hydrogen or C$_1$–C$_6$ alkyl;

R$^{13}$ is C$_1$–C$_6$ alkyl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, S(O)$_{2\text{—}N(R^{10})}$—, —N(R$^{10}$)S(O)$_2$—, or S(O)$_m$;

V is selected from:
  a) hydrogen,
  b) heterocycle,
  c) aryl,
  d) C$_1$–C$_{20}$ alkyl wherein from 0 to 4 carbon atoms are replaced with a a heteroatom selected from O, S, and N, and
  e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;
Z is independently H$_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5;
t is 3, 4 or 5; and
u is 1 or 1;
w) U.S. Ser. Nos. 08/413,137 and 08/412,830, incorporated herein by reference,

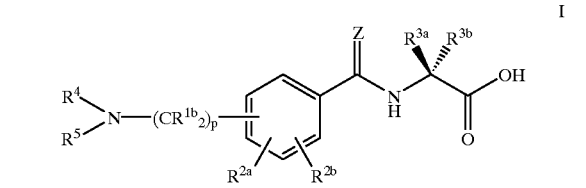

I

-continued

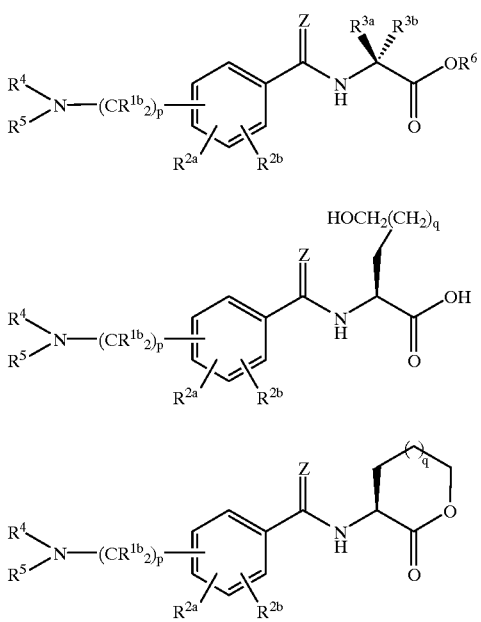

II

III

IV wherein:
$R^{1a}$ and $R^{1b}$ are independently selected from:
a) hydrogen,
b) aryl, heterocycle, cycloalkyl, alkenyl, alkynyl, $R^{10}O-$, $R^{11}S(O)_m-$, $R^{10}C(O)NR^{10}-$, CN, NO$_2$, $(R^{10})_2N-C(NR^{10})-$, $R^{10}C(O)-$, $R^{10}OC(O)-$, N$_3$, $-N(R^{10})_2$ or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}O-$, CN, $(R^{10})_2N-C(NR^{10})-$, $R^{10}C(O)-$, $R^{10}OC(O)-$, N$_3$, $-N(R^{10})_2$, or $R^{11}OC(O)-NR^{10}$;
$R^{2a}$ and $R^{2b}$ are independently selected from:
a) hydrogen,
b) $C_1-C_6$ alkyl unsubstituted or substituted by alkenyl, $R^{10}O-$, $R^{11}S(O)_m-$, $R^{10}C(O)NR^{10}-$, CN, N$_3$,$(R^{10})_2N-C(NR^{10})-$, $R^{10}C(O)-$, $R^{10}OC(O)-$, $-N(R^{10})_2$, or $R^{11}OC(O)NR^{10}-$,
c) aryl, heterocycle, cycloalkyl, alkenyl, $R^{10}O-$, $R^{11}S(O)_m-$, $R^{10}C(O)NR^{10}-$, CN, NO$_2$,$(R^{10})_2N-C(NR^{10})-$, $R^{10}C(O)-$, $R^{10}OC(O)-$, N$_3$, $-N(R^{10})_2$, or $R^{11}OC(O)NR^{10}-$, and
d) $C_1-C_6$ alkyl substituted with an unsubstituted or substituted group selected from aryl, heterocyclic and $C_3-C_{10}$ cycloalkyl;
$R^{3a}$ and $R^{3b}$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, NO$_2$, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, N$_3$, $-N(R^{10})_2$, $R^{11}OC(O)NR^{10}-$ and $C_1-C_{20}$ alkyl, and d) $C_1-C_6$ alkyl substituted with an unsubstituted or substituted group selected from aryl, heterocycle and $C_3-C_{10}$ cycloalkyl; or
$R^{3a}$ and $R^{3b}$ are combined to form $-(CH_2)_s-$ wherein one of the carbon atoms is optionally replaced by a moiety selected from: O, S(O)$_m$, $-NC(O)-$, and $-N(COR^{10})-$;
$R^4$ and $R^5$ are independently selected from:
a) hydrogen, nd
b)

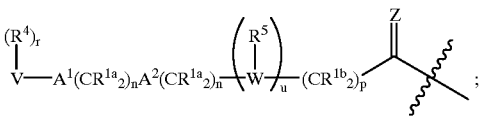

$R^6$ is
a) substituted or unsubstituted $C_1-C_8$ alkyl or substituted or unsubstituted $C_5-C_8$ cycloalkyl, wherein the substituent on the alkyl is selected from:
  1) aryl,
  2) heterocycle,
  3) $-N(R^{11})_2$,
  4) $-OR^{10}$, or b) 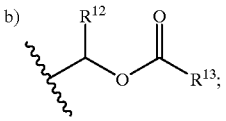

$R^7$ is independently selected from:
a) hydrogen,
b) aryl, heterocycle, cycloalkyl, alkenyl, alkynyl, perfluoroalkyl, F, Cl, Br, $R^{10}O-$, $R^{11}S(O)_m-$, $R^{10}C(O)NR^{10}-$, CN, NO$_2$, $R^{10}_2N-C(NR^{10})-$, $R^{10}C(O)-$, $R^{10}OC(O)-$, N$_3$, $-N(R^{10})_2$, or $R^{11}OC(O)NR^{10}-$, and
c) $C_1-C_6$ alkyl unsubstituted or substituted by aryl, heterocycle, cycloalkyl, alkenyl, alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $R^{10}OC(O)-$, N$_3$, $-N(R^{10})_2$, or $R^{10}OC(O)NH-$;
$R^8$ is selected from:
a) hydrogen,
b) alkenyl, alkynyl, perfluoroalkyl, F, Cl, Br, $R^{10}O-$, $R^{11}S(O)_m-$, $R^{10}C(O)NR^{10}-$, CN, NO$_2$, $(R^{10})_2N-C-(NR^{10})-$, $R^{10}C(O)-$, $R^{10}OC(O)-$, N$_3$, $-N(R^{10})_2$, or $R^{11}OC(O)NR^{10}-$, and
c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, N$_3$, $-N(R^{10})_2$, or $R^{11}OC(O)NR^{10}-$;
$R^{10}$ is independently selected from hydrogen, $C_1-C_6$ alkyl, benzyl and aryl;
$R^{11}$ is independently selected from $C_1-C_6$ alkyl and aryl;
$R^{12}$ is independently selected from hydrogen and $C_1-C_6$ alkyl;
$R^{13}$ is independently selected from $C_1-C_6$ alkyl;
$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_{2-N(R^{10})}-$, $-N(R^{10})S(O)_2-$, or S(O)$_m$;
V is selected from:

a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;
Z is independently $H_2$ or O;
m is 0, 1 or 2;
n is 0, 1, 2, 3 or 4;
p is 0, 1, 2, 3 or 4;
q is 0, 1 or 2;
r is 0 to 5, provided that r is 0 when V is hydrogen;
s is 4 or 5; and
u is 0 or 1;
x) U.S. Ser. Nos. 08/412,626 and 08/412,828, incorporated herein by reference, b) aryl, heterocycle, cycloalkyl, alkenyl, alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, c) $C_1$–$C_6$ alkyl unsubstituted or substituted by aryl, heterocyclic, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{22}OC(O)$—$NR^{10}$—;

$R^2$ and $R^3$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—,

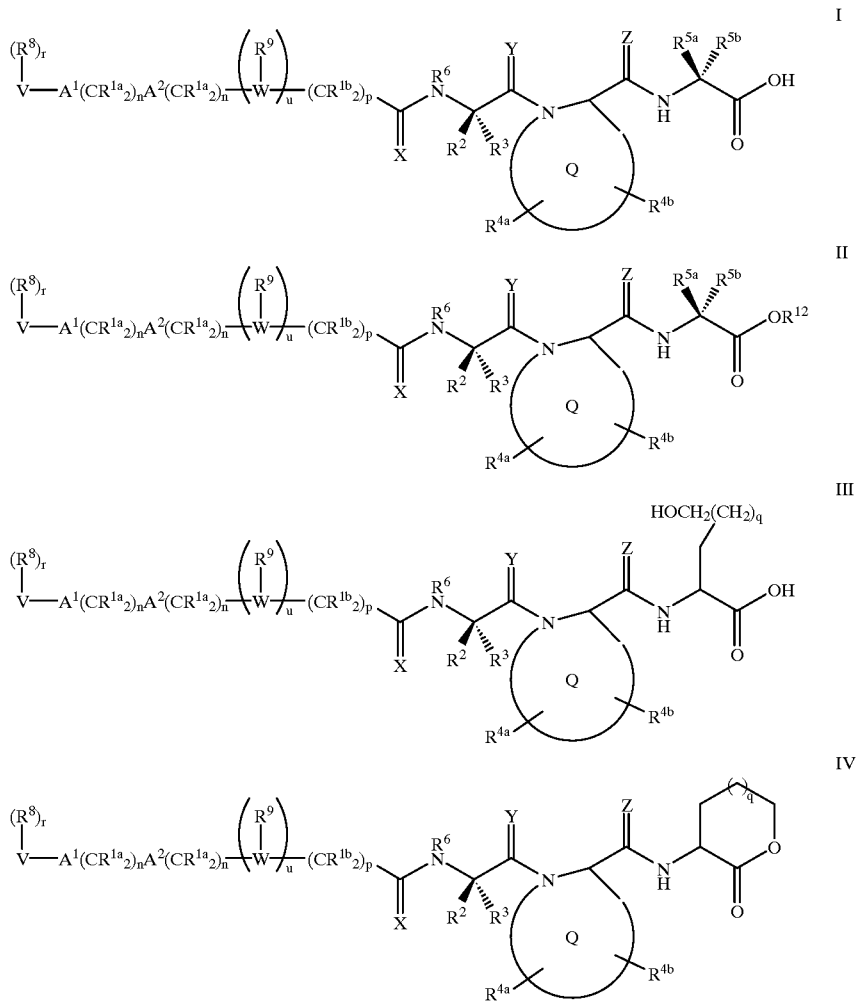

wherein:

$R^{1a}$ and $R^{2b}$ are independently selected from:
a) hydrogen, $R^{10}OC(O)$—, $N_3$, —$N(R^{10})_2$, $R^{11}OC(O)NR^{10}$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^2$ and $R^3$ are combined to form —$(CH_2)_s$—; or $R^2$ or $R^3$ are combined with $R^6$ to form a ring such that

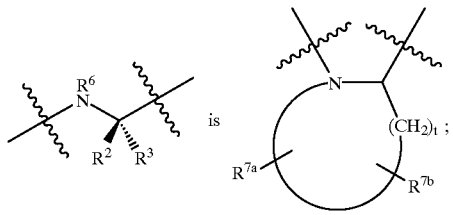

$R^{4a}$, $R^{4b}$, $R^{7a}$ and $R^{7b}$ are independently selected from:
a) hydrogen,
b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{5a}$ and $R^{5b}$ are independently selected from:
a) a side chain of a naturally occurring amino acid,
b) an oxidized form of a side chain of a naturally occurring amino acid which is:
   i) methionine sulfoxide, or
   ii) methionine sulfone,
c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}C(O)$—, $N_3$, —$N(R^{10})_2$, $R^{11}OC(O)NR^{10}$— and $C_1$–$C_{20}$ alkyl,
d) $C_1$–$C_6$ alkyl substituted with an unsubstituted or substituted group selected from aryl, heterocycle and $C_3$–$C_{10}$ cycloalkyl; or $R^{5a}$ and $R^{5b}$ are combined to form —$(CH_2)_s$— wherein one of the carbon atoms is optionally replaced by a moiety selected from: O, $S(O)_m$, —$NC(O)$—, and —$N(COR^{10})$—;

$R^6$ is independently selected from hydrogen or $C_1$–$C_6$ alkyl;

$R^8$ is independently selected from:
a) hydrogen,
b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is
a) substituted or unsubstituted $C_1$–$C_8$ alkyl or substituted or unsubstituted $C_5$–$C_8$ cycloalkyl, wherein the substituent on the alkyl or cycloalkyl is selected from:
   1) aryl,
   2) heterocycle,
   3) —$N(R^{11})_2$,
   4) —$OR^{10}$, or
b)

b) 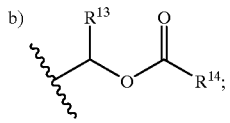

$R^{13}$ is independently selected from hydrogen and $C_1$–$C_6$ alkyl;

$R^{14}$ is independently selected from $C_1$–$C_6$ alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, $S(O)_{2-N(R^{10})}$—, —N(R$^{10}$)S(O)$_2$—, or S(O)$_m$;

Q is a substituted or unsubstituted nitrogen-containing $C_4$–$C_9$ mono or bicyclic ring system, wherein the non-nitrogen containing ring may be an aromatic ring, a $C_5$–$C_7$ saturated ring or a heterocycle;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X, Y and Z are independently $H_2$ or O;

m is 0, 1 or 2;

n is 0, 1, 2, 3 or 4;

p is 0, 1, 2, 3 or 4;

q is 0, 1 or 2;

r is 0 to 5, provided that r is 0 when V is hydrogen;

s is 4 or 5;

t is 3, 4 or 5; and u is 0 or 1;

y) U.S. Ser. No. 08/412,829 (Case 19422IA, filed June 6, 1995), incorporated herein by reference,

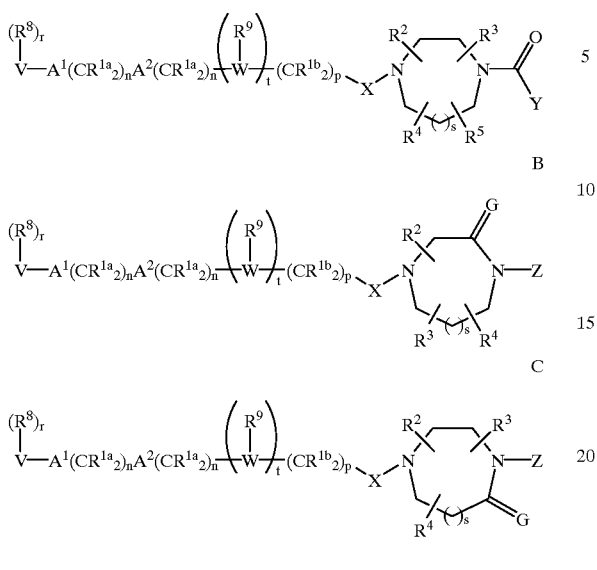

wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}C(O)$—, $N_3$, —$N(R^{10})_2$, or $R^{11}OC(O)NR^{10}$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

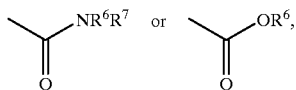

wherein the substituted group is substituted with one or more of:
1) aryl or heterocycle, unsubstituted or substituted with:
  a) $C_{1-4}$ alkyl,
  b) $(CH_2)_pOR^6$,
  c) $(CH_2)_pNR^6R^7$,
  d) halogen,
2) $C_{3-6}$ cycloalkyl,
3) $OR^6$,
4) $SR^6$, $S(O)R^6$, $SO_2 R^6$,
5) —$NR^6R^7$

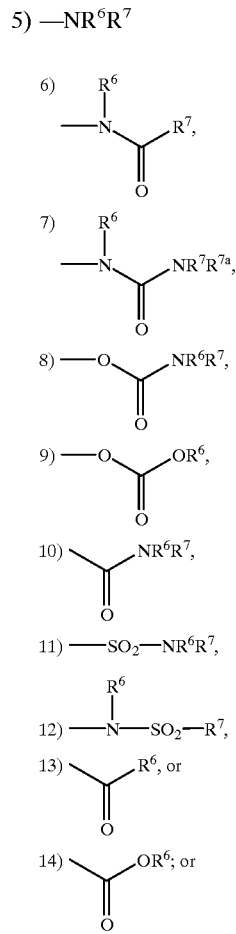

6)

7)

8)

9)

10)

11) —$SO_2$—$NR^6R^7$,

12) —N(R^6)—$SO_2$—$R^7$,

13)

14)

$R^2$ and $R^3$ are attached to the same C atom and are combined to form —$(CH_2)_u$— wherein one of the carbon atoms is optionally replaced by a moiety selected from: O, $S(O)_m$, —NC(O)—, and —$N(COR^{10})$—;

$R^4$ is selected from H and $CH_3$; and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e) 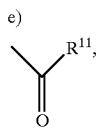
  f) —$SO_2 R^{11}$, or
  g) $N(R^{10})_2$; or $R^6$ and $R^7$ may be joined in a ring;
$R^7$ and $R^{7a}$ may be joined in a ring;
$R^8$ is independently selected from:
  a) hydrogen,
  b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S$ (O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

R$^9$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, C(O)—, —C(O)NR$^{10}$—, —NR$^{10}$C(O)—, O, —N(R$^{10}$)—, S(O)$_{2-N(R^{10})}$—, —N(R$^{10}$)S(O)$_2$—, or S(O)$_m$;

G is H$_2$ or O;

V is selected from:
a) hydrogen,
b) heterocycle,
c) aryl,
d) C$_1$–C$_{20}$ alkyl wherein from 0 to 4 carbon atoms are replaced with a a heteroatom selected from O, S, and N, n and
e) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is a heterocycle;

X is —CH$_2$—, —C(=O)—, or —S(=O)$_m$—;

Y is aryl, heterocycle, unsubstituted or substituted with one or more of:
1) C$_{1-4}$ alkyl, unsubstituted or substituted with:
   a) C$_{1-4}$ alkoxy,
   b) NR$^6$ R$^7$,
   c) C$_{3-6}$ cycloalkyl,
   d) aryl or heterocycle,
   e) HO,
   f) —S(O)$_m$ R$^6$, or
   g) —C(O)NR$^6$ R$^7$,
2) aryl or heterocycle,
3) halogen,
4) OR$^6$,
5) NR$^6$ R$^7$,
6) CN,
7) NO$_2$,
8) CF$_3$;
9) —S(O)$_m$ R$^6$,
10) —C(O)NR$^6$ R$^7$, or
11) C$_3$–C$_6$ cycloalkyl;

Z is aryl, heteroaryl, arylmethyl, heteroarylmethyl, arylsulfonyl, heteroarylsulfonyl, unsubstituted or substituted with one or more of the following:
1) C$_{1-4}$ alkyl, unsubstituted or substituted with:
   a) C$_{1-4}$ alkoxy,
   b) NR$^6$ R$^7$,
   c) C$_{3-6}$ cycloalkyl,
   d) aryl or heterocycle,
   e) HO,
   f) —S(O)$_m$ R$^6$, or
   g) —C(O)NR$^6$ R$^7$,
2) aryl or heterocycle,
3) halogen,
4) OR$^6$,
5) NR$^6$ R$^7$,
6) CN,
7) NO$_2$,
8) CF$_3$;
9) —S(O)$_m$ R$^6$,
10) —C(O)NR$^6$ R$^7$, or
11) C$_3$–C$_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1, and
u is 4 or 5;

z) U.S. Ser. No. 08/472,077, (Case 19466, filed Jun. 6, 1995), incorporated herein by reference,

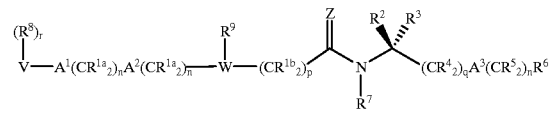

I wherein:
R$^{1a}$ is independently selected from:
a) hydrogen,
b) aryl, heterocycle, C$_3$–C$_{10}$ cycloalkyl, C$_2$–C$_{20}$ alkenyl, C$_2$–C$_{20}$ alkynyl, R$^{10}$O—, R$^{11}$S(O)$_m$—, R$^{10}$C(O)NR$^{10}$—, CN, NO$_2$,(R$^{10}$)$_2$N—C(NR$^{10}$)—, R$^{10}$C(O)—, R$^{10}$OC(O)—, N$_3$, —N(R$^{10}$)$_2$, or R$^1$C(O)NR$^{10}$—,
c) C$_1$–C$_6$ alkyl unsubstituted or substituted by aryl, heterocyclic, C$_3$–C$_{10}$ cycloalkyl, C$_2$–C$_{20}$ alkenyl, C$_2$–C$_{20}$ alkynyl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)—NR$^{10}$—;

R$^{1b}$ is independently selected from:
a) hydrogen,
b) substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, R$^{10}$O—, R$^{11}$S(O)$_m$—, CN, NO$_2$,(R$^{10}$)$_2$N—C(NR$^{10}$)—, R$^{10}$C(O)—, R$^{10}$OC(O)—, N$_3$ or —N(R$^{10}$)$_2$,
c) C$_1$–C$_6$ alkyl unsubstituted or substituted by substituted or unsubstituted aryl, substituted or unsubstituted heterocyclic, C$_3$–C$_{10}$ cycloalkyl, C$_2$–C$_{20}$ alkenyl, C$_2$–C$_{20}$ alkynyl, R$^{10}$O—, R$^{11}$S(O)$_m$—, CN, (R$^{10}$)$_2$N—C(NR$^{10}$)—, R$^{10}$C(O)—, R$^{10}$OC(O)—, N$_3$ or —N(R$^{10}$)$_2$;

R$^2$ and R$^3$ are independently selected from:
a) a side chain of a naturally occurring amino acid,
b) an oxidized form of a side chain of a naturally occurring amino acid which is:

i) methionine sulfoxide, or ii) methionine sulfone, and c) substituted or unsubstituted $C_1$–$C_{20}$ alkyl, substituted or unsubstituted $C_2$–$C_{20}$ alkenyl, substituted or unsubstituted $C_3$–$C_{10}$ cycloalkyl, substituted or unsubstituted aryl or substituted or unsubstituted heterocyclic group, wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, $R^{11}OC(O)NR^{10}$— and $C_1$–$C_{20}$ alkyl, and d) $C_1$–$C_6$ alkyl substituted with an unsubstituted or substituted group selected from aryl, heterocycle and $C_3$–$C_{10}$ cycloalkyl; or $R^2$ and $R^3$ are combined to form —$(CH_2)_s$—; or $R^2$ or $R^3$ are combined with $R^7$ to form a ring such that

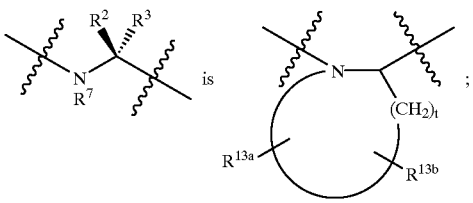

$R^4$, $R^5$, $R^{13a}$ and $R^{13b}$ are independently selected from:

a) hydrogen, b) $C_1$–$C_6$ alkyl unsubstituted or substituted by $C_2$–$C_{20}$ alkenyl, $R^{10}$—, $R^1 S(O)_m$—, $R^{10}C(O)NR^{10}$—, CN, $N_3$,$(R^{10})_2N$—$C(NR^{10})$—, $R^{10}C(O)$—, —$N(R^{10})_2$, or $R^{11}OC(O)NR^{10}$—, c) unsubstituted or substituted aryl, unsubstituted or substituted heterocycle, $C_3$–$C_{10}$ cycloalkyl, $C_2$–$C_{20}$ alkenyl, $R^{10}O$—, $R^{11}S(O)_m$—, $R^{10}C(O)NR^{10}$—, CN, $NO_2$,$(R^{10})_2N$—$C(NR^{10})$—, $R^{10}C(O)$—, $N_3$, —$N(R^{10})_2$, or $R^{11}OC(O)NR^{10}$—, and d) $C_1$–$C_6$ alkyl substituted with an unsubstituted or substituted group selected from aryl, heterocyclic and $C_3$–$C_{10}$ cycloalkyl;

$R^6$ is selected from:

a) hydrogen, b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^{10}O$, $R^{11}S(O)_m$—, $R^{10}C(O)NR^{10}$—, CN, $NO_2$, $R^{10}{}_2N$—$C(NR^{10})$—, $R^{10}C(O)$—, $N_3$, —$N(R^{10})_2$,$(R^{12})_2NC(O)$—or $R^{11}OC(O)NR^{10}$—, and c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $N_3$, —$N(R^{10})_2$, or $R^{10}OC(O)NH$—;

$R^7$ is independently selected from a) hydrogen, b) unsubstituted or substituted aryl, c) unsubstituted or substituted heterocycle, d) unsubstituted or substituted $C_3$–$C_{10}$ cycloalkyl, and e) $C_1$–$C_6$ alkyl substituted with hydrogen or an unsubstituted or substituted group selected from aryl, heterocycle and $C_3$–$C_{10}$ cycloalkyl;

$R^8$ is selected from:

a) hydrogen, b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^{10}O$—, $R^{11}S(O)_m$—, $R^{10}C(O)NR^{10}$—, —$S(O)_2NR^{10}$, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}C(O)$—, $N_3$, —$N(R^{10})_2$, or $R^{10}OC(O)NH$—;

$R^9$ is selected from:

a) hydrogen, b) $C_2$–$C_{20}$ alkenyl, $C_2$–$C_{20}$ alkynyl, $C_2$–$C_{20}$ perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by $C_2$–$C_{20}$ perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms —$(CH_2)_2$—;

$A^1$, $A^2$ and $A^3$ are independently selected from: a bond, —CH=CH—, —C≡C—, —C(O)—, —C(O)NR$^7$—, —NR$^7$C(O)—, O, —N(R$^7$)—, $S(O)_{2-N(R}{}^7{}_)$—, —N(R$^7$)S(O)$_2$—, or $S(O)_m$;

V is selected from:

a) hydrogen, b) heterocycle, c) aryl, d) $C_1$–$C_{20}$ alkyl wherein from 0 to 4 carbon atoms are replaced with a a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $H_2$ or O;

m is 0, 1 or 2;

n is 0, 1, 2, 3 or 4;

p is 0, 1, 2, 3 or 4;

q is 0, 1, 2, 3 or 4;

r is 0 to 5, provided that r is 0 when V is hydrogen;

s is 4 or 5; and t is 3, 4 or 5;

and aa) U.S. Ser. No. 08/449,038, incorporated herein by reference,

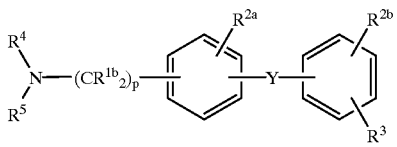

wherein:

$R^{1a}$ and $R^{1b}$ are independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$,$(R^8)_2N$—C$(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, unsubstituted or substituted heterocyclic, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—C$(NR^8)$—, $R^8C(O)$—, $R^8OC(O)$—, $N_3$, —$N(R^8)_2$, or $R^9OC(O)$—$NR^8$—;

$R^{2a}$, $R^{2b}$ and $R^3$ are independently selected from:
a) hydrogen,
b) $C_1$–$C_6$ alkyl unsubstituted or substituted by $C_2$–$C_6$ alkenyl, $R^8O$—, $R^9S(O)_m$—, $R^8C(O)NR^8$—, CN, $N_3$, $(R^8)_2N$—C$(NR^8)$—, $R^8C(O)$—, $R^8OC(O)$—, —$N(R^8)_2$, or $R^9OC(O)NR^8$—,
c) unsubstituted or substituted aryl, unsubstituted or substituted heterocycle, unsubstituted or substituted cycloalkyl, alkenyl, $R^8O$—, $R^9S(O)_m$—, $R^8C(O)NR^8$—, CN, $NO_2$, $(R^8)_2N$—C$(NR^8)$—, $R^8C(O)$—, $R^8OC(O)$—, $N_3$, —$N(R^8)_2$, halogen or $R^9OC(O)NR^8$—, and
d) $C_1$–$C_6$ alkyl substituted with an unsubstituted or substituted group selected from aryl, heterocyclic and $C_3$–$C_{10}$ cycloalkyl;

$R^4$ and $R^5$ are independently selected from:
a) hydrogen, and
b)

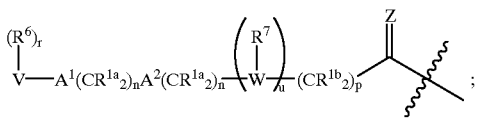

$R^6$ is independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$, $R^8_2N$—C$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)$NH—, CN, $H_2N$—C(NH)—, $R^8C(O)$—, $R^8OC(O)$—, $N_3$, —$N(R^8)_2$, or $R^8OC(O)$NH—;

$R^7$ is selected from:
a) hydrogen,
b) $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$,$(R^8)_2N$—C—$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by $C_1$–$C_6$ perfluoroalkyl, F, Cl, Br, $R^8O$—, $R^9S(O)_m$—, $R^8C(O)NR^8$—, CN, $(R^8)_2N$—C$(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_6$ alkyl, substituted or unsubstituted $C_1$–$C_6$ aralkyl and substituted or unsubstituted aryl;

$A^1$ and $A^2$ are independently selected from: a bond, —CH=CH—, —C≡C—, C(O)—, —C(O)$NR^8$—, —$NR^8C(O)$—, O, —$N(R^8)$—, —$S(O)_{2-N(R^8)}$—, $N(R^8)S(O)_2$—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Y is selected from: a bond, —$C(R^{10})$=$C(R^{10})$—, —C≡C—, —C(O)—, —$C(R^{10})_2$—, —$C(OR^{10})R^{10}$—, —$CN(R^{10})_2R^{10}$—, —$OC(R^{10})_2$—, —$NR^1OC(R^{10})_2$—, $C(R^{10})_2$—, —$C(R^{10})_2NR^{10}$—$C(O)NR^{10}$—, —$NR^{10}C(O)$—, O, —$NC(O)R^{10}$—, —$NC(O)OR^{10}$—, —$S(O)_{2-N(R^{10})}$—, —$N(R^{10})S(O)_2$—, or $S(O)_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or the pharmaceutically acceptable salts thereof.

The method and composition of the instant invention may alternatively or in addition comprise a protein substrate-competitive inhibitor obtained by fermentation of cultures of novel organisms. In particular, the compounds disclosed in the following patents and publications may be useful as a protein substrate-competitive inhibitor component of the instant composition: U.S. Pat. No. 5,420,334; and Ser. No. 08/435,047. Those patents and publications are incorporated herein by reference.

In addition, compounds described in the following patents and publications may also be utilized as a protein substrate-competitive inhibitor component of the instant composition: U.S. Pat. No. 5,420,245; European Pat. Publ. 0 618 221; PCT Pat. Publs. WO 94/26723; WO 95/08542 ; WO 95/11917; and WO 95/12612. Those patents and publications are incorporated herein by reference.

Specific examples of protein substrate-competitive inhibitors useful in the method and composition of the invention are:

Compound A:

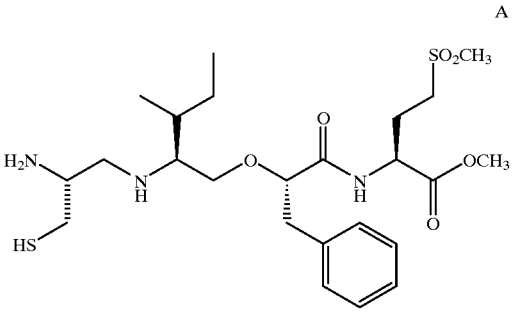

or the pharmaceutically acceptable salts thereof.

Other specific examples of protein substrate-competitive inhibitors useful in the compositions of the invention are:

5(S)-[2(R)-amino-3-mercaptopropylamino]-6(S)-methyl-2(R)-n-propyl-3,4-E-octenoyl-homoserine, and the corresponding homoserine lactone,
5(S)-[2(R)-amino-3-mercaptopropylamino]-6(S)-methyl-2(R)-methyl-3,4-E-octenoyl-homserine, and the corresponding homoserine lactone,
5(S)-[2(R)-amino-3-mercaptopropylamino]-6(S)-methyl-2(R)-ethyl-3,4-E-octenoyl-homserine, and the corresponding homoserine lactone,
5(S)-[2(R)-amino-3-mercaptopropylamino]-6(S)-methyl-2(R)-i-propyl-3,4-E-octenoyl-homoserine, and the corresponding homoserine lactone,
5(S)-[2(R)-amino-3-mercaptopropylamino]-6(S)-methyl-2(R)-n-butyl-3,4-E-octenoyl-homoserine, and the corresponding homoserine lactone,
5(S)-[2(R)-amino-3-mercaptopropylamino]-6(S)-methyl-2(R)-s-butyl-3,4-E-octenoyl-homoserine, and the corresponding homoserine lactone,
5(S)-[2(R)-amino-3-mercaptopropylamino]-6(S)-methyl-2(R)-t-butyl-3,4-E-octenoyl-homoserine, and the corresponding homoserine lactone,
5(S)-[2(R)-amino-3-mercaptopropylamino]-6(S)-methyl-2(R)-cyclohexyl-3,4-E-octenoyl-homoserine, and the corresponding homoserine lactone,
5(S)-[2(R)-amino-3-mercaptopropylarnino]-6(S)-methyl-2(R)-cyclopentyl-3,4-E-octenoyl-homoserine, and the corresponding homoserine lactone,
5(S)-[2(R)-amino-3-mercaptopropylamino]-6(S)-methyl-2(R)-benzyl-3,4-E-octenoyl-homoserine, and the corresponding homoserine lactone,
5(S)-[2(R)-amino-3-mercaptopropylamino]-6-methyl-2(R)-i-propyl-3,4-E-octenoyl-homoserine, and the corresponding homoserine lactone,
5(S)-[2(R)-amino-3-mercaptopropylamino]-6(S)-methyl-2(R)-i-propyl-3,4-E-octenoyl-methionine, and the corresponding methyl ester,
5(S)-[2(R)-amino-3-mercaptopropylamino]-6(S)-methyl-2(R)-n-butyl-3,4-E-octenoyl-methionine, and the corresponding methyl ester,
5(S)-[2(R)-amino-3-mercaptopropylamino]-6(S)-methyl-2(R)-benzyl-3,4-E-octenoyl-methionine, and the corresponding methyl ester,
5(S)-[2(R)-amino-3-mercaptopropylamino]-6(S)-methyl-2(R)-n-propyl-octanoyl-homoserine, and the corresponding homoserine lactone,
5(S)-[2(R)-amino-3-mercaptopropylamino]-6(S)-methyl-2(R)-benzyl-octanoyl-homoserine, and the corresponding homoserine lactone,
N-(3-phenyl-2(S)-(mercaptopropionylamino)prop-1-yl)isoleucyl-methionine,
N-(2(R)-amino-3-mercaptopropyl)isoleucyl-phenylalanyl-methionine,
N-(3-mercaptopropyl)isoleucyl-phenylalanyl-methionine,
N-(3-mercaptopropyl)valyl-isoleucyl-methionine,
N-(2(R)-amino-3-mercaptopropyl)valyl-isoleucyl-methionine,
N-(3-methyl-2(S)-(cysteinylamino)but-1-yl)phenylalanyl-methionine,
N-(3-methyl-2(S)-(mercaptopropionylamino)but-1-yl)-phenylalanyl-methionine,
N-[2(S)-(2(R)-amino-3-mercaptopropylamino)-3(S)methylpentyl]-phenylalanyl-methionine,
N-[2(S)-(3-mercaptopropylamino)-3(S)methylpentyl]-phenylalanyl-methionine,
N-(2(R)-amino-3-mercaptopropyl)isoleucyl-phenylalanyl-(methionine sulfone),
N-(2(R)-amino-3-mercaptopropyl)isoleucyl-(p-iodophenylalanyl)-methionine,
N-[2(R)-(cysteinyl-isoleucylamino)-3(S)-methylpentyl]-methionine,
N-[2(R)-(N'-(2(R)-amino-3-mercaptopropyl)-isoleucylamino)-3-phenyl-propyl]methionine,
N-[2(R)-(N'-(2(R)-amino-3-mercaptopropyl)-isoleucylamino)-3(S)-methylpentyl]methionine,
N-(3-mercaptopropyl)valyl-isoleucyl-methionine methyl ester,
N-(2(R)-amino-3-mercaptopropyl)isoleucyl-phenylalanyl-methionine ethyl ester,
N-(2(R)-amino-3-mercaptopropyl)isoleucyl-phenylalanyl-methionine benzyl ester,
N-[2(R)-Amino-3-mercaptopropyl]-L-isoleucine-phenethylamide,
N-[2(R)-Amino-3-mercaptopropyl]-L-isoleucine-benzylamide,
N-[2(R)-Amino-3-mercaptopropyl]-L-isoleucine-3-methylbutylamide,
N-[2(R)-Amino-3-mercaptopropyl]-L-isoleucine-3-phenylpropylamide,
N-[2(R)-Amino-3-mercaptopropyl]-L-isoleucyl-L-phenylalaninol,
N-[2(R)-Amino-3-mercaptopropyl]-L-isoleucine-N'-methylbenzylamide,
N-[2(R)-Amino-3-mercaptopropyl]-L-isoleucine-(4-methoxybenzyl)amide,
N-[2(R)-Amino-3-mercaptopropyl]-L-isoleucine-(2,4-dichlorobenzyl)amide,
N-[2(R)-Amino-3-mercaptopropyl]-L-isoleucine-(4-trifluoromethylbenzyl)amide,
N-[2(R)-Amino-3-mercaptopropyl]-L-isoleucine-(2,4-dichlorophenethyl)amide,
N-[2(R)-Amino-3-mercaptopropyl]-L-isoleucine-(2-benzimidazolylmethyl)amide,
N-[2(R)-Amino-3-mercaptopropyl]-L-isoleucine-(1-indanyl)amide,
N-[2(R)-Amino-3-mercaptopropyl]-L-isoleucine-(2,4-dimethylbenzyl)amide,
N-[2(R)-Amino-3-mercaptopropyl]-L-isoleucine-(2,3-dichlorobenzyl)amide,
N-[2(R)-Amino-3-mercaptopropyl]-L-isoleucine-(4-sulfamoylbenzyl)amide,
N-[2(R)-Amino-3-mercaptopropyl]-L-isoleucineanilide,
N-[2(R)-Amino-3-mercaptopropyl]-L-isoleucine-(2,4-dimethyl-phenyl)amide,
N-[2(R)-Amino-3-mercaptopropyl]-L-isoleucine-(2,3-dimethylphenyl)amide,
L-Cysteinyl-L-isoleucine-phenethylamide,
N-[2(S)-[2(R)-Amino-3-mercaptopropylamino]-3-methylpentyl]-phenethylamide, N-(2(R)-Amino-3-mercaptopropyl)-L-alaninebenzylamide,
N-Benzyl-[2(S)-2(R)-Amino-3-mercaptopropyl)-amino] butyramide,
N-(2(R)-Amino-3-mercaptopropyl)-L-norleucinebenzylamide,
N-(2(R)-Amino-3-mercaptopropyl)-L-norvalinebenzylamide,
N-(2(R)-Amino-3-mercaptopropyl)isoleucyl-phenylalanyl-homoserine,
N-(2(R)-Amino-3-mercaptopropyl)isoleucyl-isoleucyl-homoserine,
N-(2(R)-Amino-3-mercaptopropyl)isoleucyl-phenylalanyl-homoserine lactone,
N-(2(R)-Amino-3-mercaptopropyl)isoleucyl-isoleucyl-homoserine lactone,
N-(2(R)-Amino-3-mercaptopropyl)isoleucyl-phenylalanyl-homocysteine lactone,
N-[2(S)-(2(R)-Amino-3-mercaptopropyl)-3(S)-methylpentyl]-isoleucyl-homoserine lactone,
N-[N'-(2(R)-Amino-3-mercaptopropyl)isoleucyl-phenylalanyl]-3(S)-amino-tetrahydropyran-2-one,
N-[N'-(2(R)-Amino-3-mercaptopropyl)isoleucyl-isoleucyl]-3(S)-amino-tetrahydropyran-2-one,
N-(2(R)-Amino-3-mercaptopropyl)isoleucyl-isoleucyl-homocysteine lactone,
N-[2(S)-(2(R)-Amino-3-mercaptopropylamino)-3(S)-methyl pentyl]isoleucyl-homoserine,
N-[N'-(2(R)-Amino-3-mercaptopropyl)isoleucyl-phenylalanyl]-3(S)-amino-4-hydroxypentanoic acid,
N-[N'-(2(R)-Amino-3-mercaptopropyl)isoleucyl-isoleucyl]-3(S)-amino-4-hydroxypentanoic acid,
N-[2(S)-(2(R)-amino-3-mercaptopropylamino)-3(S)-methylpentyl]-N-methyl-isoleucyl-homoserine,
N-[2(S)-(2(R)-amino-3-mercaptopropylamino)-3(S)-methylpentyl]-N-methyl-isoleucyl-homoserine lactone,
N-[2(S)-(2(R)-amino-3-mercaptopropylamino)-3(S)-methylpentyl]-N-methyl-phenylalanyl-homoserine,
N-[2(S)-(2(R)-amino-3-mercaptopropylamino)-3(S)-methylpentyl]-N-methyl-phenylalanyl-homoserine lactone,
N-[2(S)-(2(R)-amino-3-mercaptopropylamino)-3-methyl-butyl]-N-methyl-phenylalanyl-homoserine,
N-[2(S)-(2(R)-amino-3-mercaptopropylamino)-3-methyl-butyl]-N-methyl-phenylalanyl-homoserine lactone,
3(S)-{N-[2(S)-(2(R)-amino-3-mercaptopropylamino)-3(S)-methyl-pentyl]-N-methyl-isoleucylamino}-3-methyltetra-hydropyran-2-one,
2(S)-{N-[2(S)-(2(R)-amino-3-mercaptopropylamino)-3(S)-methyl-pentyl]-N-methyl-isoleucylamino}-2-methyl-5-hydroxypentanoic acid,
2(S)-{N-[2(S)-(2(R)-amino-3-mercaptopropylamino)-3(S)-methylpentyl]-N-methyl-isoleucylamino}-5-methyl-5-hydroxyhexanoic acid,
N-[2(S)-(2(R)-amino-3-mercaptopropylamino)-3(S)-methylpentyl]-N-methyl-norvalyl-homoserine,
N-[2(S)-(2(R)-amino-3-mercaptopropylamino)-3(S)-methylpentyl]-N-methyl-norvalyl-homoserine lactone,
N-[2(S)-(2(R)-amino-3-mercaptopropylamino)-3(S)-methylpentyl]-N-methyl-isoleucyl-methionine,
N-[2(S)-(2(R)-amino-3-mercaptopropylamino)-3(S)-methylpentyl]-N-methyl-isoleucyl-methionine methyl ester,
N-[2(S)-(2(R)-amino-3-mercaptopropylamino)-3(S)-methylpentyl]-N-methyl-phenylalanyl-methionine,
N-[2(S)-(2(R)-amino-3-mercaptopropylamino)-3(S)-methylpentyl]-N-methyl-phenylalanyl-methionine methyl ester,
3(S)-{N-[2(S)-(2(R)-amino-3-mercaptopropylamino)-3(S)-methyl-pentyl]-N-methyl-isoleucylamino}-6,6-dimethyl-tetrahydropyran-2-one,
N-[2(S)-(2(R)-amino-3-mercaptopropylamino)-3(S)-methylpentyl]-N-methyl-norvalyl-methionine,
N-[2(S)-(2(R)-amino-3-mercaptopropylamino)-3(S)-methylpentyl]-N-methyl-norvalyl-methionine methyl ester,
N-[2(S)-(2(R)-amino-3-mercaptopropylamino)-3(S)-methylpentyl]-N-methyl-D-norvalyl-homoserine,
N-[2(S)-(2(R)-amino-3-mercaptopropylamino)-3(S)-methylpentyl]-N-methyl-D-norvalyl-homoserine lactone,
2(S)-[2(S)-[2(R)-Amino-3-mercapto]propylamino-3(S)-methyl]-pentyloxy-3-phenylpropionyl-homoserine lactone,
2(S)-[2(S)-[2(R)-Amino-3-mercapto]propylamino-3(S)-methyl]-pentyloxy-3-phenylpropionyl-homoserine,
2(S)-[2(S)-[2(R)-Amino-3-mercapto]propylamino-3(S)-methyl]-pentyloxy-2-methyl-3-phenylpropionyl-homoserine lactone,
2(S)-[2(S)-[2(R)-Amino-3-mercapto]propylamino-3(S)-methyl]-pentyloxy-2-methyl-3-phenylpropionyl-homoserine,
2(S)-[2(S)-[2(R)-Amino-3-mercapto]propylamino-3(S)-methyl]-pentyloxy-4-pentenoyl-homoserine lactone,
2(S)-[2(S)-[2(R)-Amino-3-mercapto]propylamino-3(S)-methyl]-pentyloxy-4-pentenoyl-homoserine,
2(S)-[2(S)-[2(R)-Amino-3-mercapto]propylamino-3(S)-methyl]-pentyloxypentanoyl-homoserine lactone,
2(S)-[2(S)-[2(R)-Amino-3-mercapto]propylamino-3(S)-methyl]-pentyloxypentanoyl-homoserine,
2(S)-[2(S)-[2(R)-Amino-3-mercapto]propylamino-3(S)-methyl]-pentyloxy-4-methylpentanoyl-homoserine lactone,
2(S)-[2(S)-[2(R)-Amino-3-mercapto]propylamino-3(S)-methyl]-pentyloxy-4-methylpentanoyl-homoserine,
2(S)-[2(S)-[2(R)-Amino-3-mercapto]propylamino-3(S)-methyl]-pentyloxy-3-methylbutanoyl-homoserine lactone,
2(S)-[2(S)-[2(R)-Amino-3-mercapto]propylamino-3(S)-methyl]-pentyloxy-3-methylbutanoyl-homoserine,
2(S)-[2(S)-[2(R)-Amino-3-mercapto]propylamino-3(S)-methyl]-pentyloxy-3-phenylbutanoyl-homoserine lactone,
2(S)-[2(S)-[2(R)-Amino-3-mercapto]propylamino-3(S)-methyl]-pentyloxy-3-phenylbutanoyl-homoserine,
2(S)-[2(S)-[2(R)-Amino-3-mercapto]propylamino-3(S)-methyl]-pentylthio-2-methyl-3-phenylpropionyl-homoserine lactone,
2(S)-[2(S)-[2(R)-Amino-3-mercapto]propylamino-3(S)-methyl]-pentylthio-2-methyl-3-phenylpropionyl-homoserine,
2(S)-[2(S)-[2(R)-Amino-3-mercapto]propylamino-3(S)-methyl]-pentylsulfonyl-2-methyl-3-phenylpropionyl-homoserine lactone,
2(S)-[2(S)-[2(R)-Amino-3-mercapto]propylamino-3(S)-methyl]-pentylsulfonyl-2-methyl-3-phenylpropionyl-homoserine,
2(S)-[2(S)-[2(R)-Amino-3-mercapto]propylamino-3(S)-methyl]-pentyloxy-3-phenylpropionyl-methionine methyl ester,
2(S)-[2(S)-[2(R)-Amino-3-mercapto]propylamino-3(S)-methyl]-pentyloxy-3-phenylpropionyl-methionine,
2(S)-[2(S)-[2(R)-Amino-3-mercapto]propylamino-3(S)-methyl]-pentyloxy-3-phenylpropionyl-methionine sulfone isopropyl ester,
2(S)-[2(S)-[2(R)-Amino-3-mercapto]propylamino-3(S)-methyl]-pentyloxy-3-phenylpropionyl-methionine sulfone, 2-(S)-[2(S)-[2(R)-Amino-3-mercapto]propylamino-3(S)-methyl]-pentyloxy-3-naphth-2-yl-propionyl-methionine sulfone methyl ester,
2-(S)-[2(S)-[2(R)-Amino-3-mercapto]propylamino-3(S)-methyl]-pentyloxy-3-naphth-2-yl-propionyl-methionine sulfone,
2-(S)-[2(S)-[2(R)-Amino-3-mercapto]propylamino-3(S)-methyl]-pentyloxy-3-naphth-1-yl-propionyl-methionine sulfone methyl ester,
2-(S)-[2(S)-[2(R)-Amino-3-mercapto]propylamino-3(S)-methyl]-pentyloxy-3-naphth-1-yl-propionyl-methionine sulfone,
2-(S)-[2(S)-[2(R)-Amino-3-mercapto]propylamino-3(S)-methyl]-pentyloxy-3-methybutanoyl-methionine methyl ester,
2-(S)-[2(S)-[2(R)-Amino-3-mercapto]propylamino-3(S)-methyl]-pentyloxy-3-methybutanoyl-methionine,
Disulphide of 2(S)-[2(S)-[2(R)-Amino-3-mercapto]propylamino-3(S)-methyl]pentyloxy-3-phenylpropionyl-homoserine lactone,
Disulphide of 2(S)-[2(S)-[2(R)-Amino-3-mercapto]propylamino-3(S)-methyl]pentyloxy-3-phenylpropionyl-homoserine,
Disulphide of 2(S)-[2(S)-[2(R)-Amino-3-mercapto]propylamino-3(S)-methyl]pentyloxy-3-methylbutanoyl-methionine methyl ester.
1-[2-(R)-Amino-3-mercaptopropyl]-2(S)-(1-butyl)-4-(2,3-dimethyl-benzoyl)piperazine dihydrochloride
1-[2(R)-Amino-3-mercaptopropyl]-2(S)-(n-butyl)-4-(1-naphthoyl)piperazine
1-[2(R)-Amino-3-mercaptopropyl]-2(S)-benzyl-4-[1-(2,3-dimethyl)benzoyl]piperazine
1-[2(R)-Amino-3-mercaptopropyl]-2(S)-(2-methoxy)ethyl-4-[1-(2,3-dimethyl)benzoyl]piperazine
1[2(R)-Amino-3-mercaptopropyl]-2(S)-(2-methylthio)ethyl-4[1-(2,3-dimethyl)benzoyl]piperazine
2-[2(R)-Amino-3-mercaptopropyl]-2(S)-(n -butyl)-4-[7-(2,3-dihydrobenzofuroyl)]piperazine
1-(2(R)-Amino-3-mercaptopropyl)-4-(1-naphthoyl)-2(S)-pyridinylcarboxyl-4-piperazine dihydrochloride
Methyl 4-(2(R)-amino-3-mercaptopropyl)-1-(1-naphthylmethyl)piperazine-2-carboxylate hydrochloride
1[2(R)-Amino-3-mercaptopropyl]-2(S)-(2-methoxyethyl)-4-(1-naphthoyl)piperazine
1-[2(R)-Amino-3-mercaptopropyl]-2(S)-n-butyl-4-(8-quinolinylcarbonyl)piperazine
1-[2(R)-Amino-3-mercaptopropyl]-2(S)-(2-(-propoxy)ethyl)-4-(1-naphthoyl) piperazine
1-[2(R)-Amino-3-mercaptopropyl]-2(S)-(3-methoxy-1-propyl)-4-(1-naphthoyl) piperazine
1-[2(R)-Amino-3-mercaptopropyl]-2(S)-(2-(1-propoxy)ethyl)-4-(8-quinolinoyl)piperazine
1-[2(R)-Amino-3-mercaptopropyl]-2(S)-[(3-pyridyl)methoxyethyl)]-4-(1-naphthoyl)piperazine
1-[2(R)-Amino-3-mercaptopropyl]-4-naphthoyl-2(S)-(2-phenylsulfonyl-ethyl)piperazine dihydrochloride
bis-1,1'-[2(R)-Amino-3-(2(S)-(2-methoxyethyl)-4-naphthoyl-1-piperazinyl)]propyl disulfide tetrahydrochloride
bis-1,1'-[2(R)-Amino-3-(4-naphthoyl-2(S)-(2-phenylsulfonylethyl)-1-piperazinyl)]propyl disulfide tetrahydrochloride
1-[2(R)-Amino-3-mercaptopropyl]-4-naphthoyl-2(S)-(2-cyclopropyloxyethyl)piperazine dihydrochloride
1-[2(R)-Amino-3-mercaptopropyl]-4-(1-naphthoyl)-2(S)-(4-acetamidobutyl)piperazine dihydrochloride
1-[2(R)-Amino-3-mercaptopropyl]-4-naphthoyl-2(S)-(2-cyclopropylmethylsulfonylethyl)piperazine dihydrochloride Pyroglutamyl-valyl-phenylalanyl-methionine
Pyroglutamyl-valyl-phenylalanyl-methionine methyl ester;
Pyroglutamyl-valyl-isoleucyl-methionine;
Pyroglutamyl-valyl-isoleucyl-methionine methyl ester;
Nicotinoyl-isoleucyl-phenylalanyl-methionine;
Nicotinoyl-isoleucyl-phenylalanyl-methionine methyl ester;
N-[2(S)-(L-Pyroglutamylamino)-3-methylbutyl]phenylalanyl-methionine;
N-[2(S)-(L-Pyroglutamylamino)-3-methylbutyl]phenylalanyl-methionine methyl ester;
N-[5(S)-(L-Pyroglutamylamino)-6(S)-methyl-2(R)-butyl-3,4(E)-octenoyl]-methionine;
N-[5(S)-(L-Pyroglutamylamino)-6(S)-methyl-2(R)-butyl-3,4(E)-octenoyl]-methionine methyl ester;
N-[5(S)-((Imidazol-4-yl)acetylamino)-6(S)-methyl-2(R)-butyl-3,4(E)-octenoyl]-methionine;
N-[5(S)-((Imidazol-4-yl)acetylamino)-6(S)-methyl-2(R)-butyl-3,4(E)-octenoyl]-methionine methyl ester;
N-[5(S)-((Imidazol-4-ylcarbonylamino)-6(S)-methyl-2(R)-butyl-3,4(E)-octenoyl]-methionine;
N-[5(S)-((Imidazol-4-ylcarbonylamino)-6(S)-methyl-2(R)-butyl-3,4(E)-octenoyl]-methionine methyl ester;
N-[2(S)-(2(S)-(Imidazol-4-yl)acetylamino)-3(S)-methylpentyloxy)-3-phenylpropionyl]-methionine;
N-[2(S)-(2(S)-(Imidazol-4-yl)acetylamino)-3(S)-methylpentyloxy)-3-phenylpropionyl]-methionine methyl ester;
N-[2(S)-(2(S)-Pyroglutamylamino)-3(S)-methylpentyloxy)-3-phenylpropionyl]-methionine;
N-[2(S)-(2(S)-Pyroglutamylamino)-3(S)-methylpentyloxy)-3-phenylpropionyl]-methionine methyl ester;
N-[2(S)-(2(S)-Imidazol-4-ylcarbonyl)amino)-3(S)-methylpentyloxy)-3-phenylpropionyl]-methionine;
N-[2(S)-(2(S)-Imidazol-4-ylcarbonyl)amino)-3(S)-methylpentyloxy)-3-phenylpropionyl]-methionine methyl ester;
N-[2(S)-(2(S)-((3-Picolinyl)amino)-3(S)-methylpentyloxy)-3-phenylpropionyl]-methionine;
N-[2(S)-(2(S)-((3-Picolinyl)amino)-3(S)-methylpentyloxy)-3-phenylpropionyl]-methionine methyl ester;
N-[2(S)-(2(S)-((Histidyl)amino)-3(S)-methylpentyloxy)-3-phenylpropionyl]-methionine;
N-[2(S)-(2(S)-((Histidyl)amino)-3(S)-methylpentyloxy)-3-phenylpropionyl]-methionine methyl ester;
N-Benzyl-N-[2(S)-((Imidazol-4-ylcarbonyl)amino)-3(S)-methylpentyl]-glycyl-methionine;
N-Benzyl-N-[2(S)-((Imidazol-4-ylcarbonyl)amino)-3(S)-methylpentyl]-glycyl-methionine methyl ester;
N-Benzyl-N-[2(S)-((Imidazol-4-ylacetyl)amino)-3(S)-methylpentyl]-glycyl-methionine;
N-Benzyl-N-[2(S)-((Imidazol-4-ylacetyl)amino)-3(S)-methylpentyl]-glycyl-methionine methyl ester;
N-Benzyl-N-[2(S)-((Pyroglutamyl)amino)-3(S)-methylpentyl]-glycyl-methionine;
N-Benzyl-N-[2(S)-((Pyroglutamyl)amino)-3(S)-methylpentyl]-glycyl-methionine methyl ester;
N-(1-Naphthylmethyl)-N-[2(S)-((imidazol-4-ylcarbonyl)amino)-3(S)-methylpentyl]-glycyl-methionine;
N-(1-Naphthylmethyl)-N-[2(S)-((imidazol-4-ylcarbonyl)amino)-3(S)-methylpentyl]-glycyl-methionine methyl ester;
N-(1-Naphthylmethyl)-N-[2(S)-((imidazol-4-ylacetyl)amino)-3(S)-methylpentyl]-glycyl-methionine;
N-(1-Naphthylmethyl)-N-[2(S)-((imidazol-4-ylacetyl)amino)-3(S)-methylpentyl]-glycyl-methionine methyl ester;
N-(1-Naphthylmethyl)-N-[2(S)-((pyroglutamyl)amino-3(S)-methyl-pentyl]-glycyl-methionine; and N-(1-Naphthylmethyl)-N-[2(S)-((pyroglutamyl)amino-3(S)-methyl-pentyl]-glycyl-methionine methyl ester;
N-[1-(Pyroglutamylamino)cyclopent-1-ylmethyl]-N-(1-naphthylmethyl)-glycyl-methionine methyl ester
N-[1-(Pyroglutamylamino)-cyclopent-1-ylmethyl]-N-(1-naphthylmethyl)-glycyl-methionine
N-(2(S)-L-Histidylamino-3(S)-methylpentyl)-N-(benzylmethyl)glycyl-methionine methyl ester
N-(2(S)-L-Histidylamino-3(S)-methylpentyl)-N-(benzylmethyl)glycyl-methionine
N-(2(S)-L-Histidylamino-3(S)-methylpentyl)-N-(1-naphthylmethyl)-glycyl-methionine methyl ester
N-(2(S)-L-Histidylamino-3(S)-methylpentyl)-N-(1-naphthylmethyl)-glycyl-methionine
2(S)-[2(S)-(L-Pyroglutamyl)amino-3(S)-methylpentyloxy]-3-methylbutanoyl-methionine methyl ester
2(S)-[2(S)-(L-Pyroglutamyl)amino-3(S)-methylpentyloxy]-3-methylbutanoyl-methionine
2(S)-[2(S)-(Imidazol-4-ylacetyl)amino-3(S)-methylpentyloxy]-3-methylbutanoyl-methionine methyl ester
2(S)-[2(S)-(Imidazol-4-ylacetyl)amino-3(S)-methylpentyloxy]-3-methylbutanoyl-methionine
N-(Benzyl)-N-[2(S)-(2-oxopyrrolidin-5(R,S)-ylmethyl)amino-3(S)-methylpentyl]-glycyl-methionine methyl ester
N-(Benzyl)-N-[2(S)-(2-oxopyrrolidin-5(R,S)-ylmethyl)amino-3(S)-methylpentyl]-glycyl-methionine
N-(Benzyl)-N-{2(S)-[((D,L)-2-thiazolyl)alanyl)amino]-3(S)-methylpentyl}-glycyl-methionine methyl ester
N-(Benzyl)-N-{2(S)-[((D,L)-2-thiazolyl)alanyl)amino]-3(S)-methylpentyl} -glycyl-methionine
N-(Benzyl)-N-[2(S)-(3-pyridylmethyl)amino-3(S)-methylpentyl]-glycyl-methionine methyl ester
N-(Benzyl)-N-[2(S)-(3-pyridylmethyl)amino-3(S)-methylpentyl]-glycyl-methionine
2(S)-[2(S)-(2-Oxopyrrolidin-5(S)-ylmethyl)amino-3(S)-methylpentyloxy]-3-phenylpropionyl-methionine methyl estr
2(S)-[2(S)-(2-Oxopyrrolidin-5(S)-ylmethyl)amino-3(S)-methyl-pentyloxy]-3-phenylpropionyl-methionine
2(S)-[2(S)-(L-Pyroglutamyl)amino-3(S)-methylpentyloxy]-3-(1-naphthyl)propionyl-methionine sulfone methyl ester
2(S)-[2(S)-(L-Pyroglutamyl)amino-3(S)-methylpentyloxy]-3-(1-naphthyl)propionyl-methionine sulfone
2(S)-[2(S)-(L-Pyroglutamyl)amino-3(S)-methylpentyloxy]-3-(2-naphthyl)propionyl-methionine sulfone methyl ester
2(S)-[2(S)-(L-Pyroglutamyl)amino-3(S)-methylpentyloxy]-3-(2-naphthyl)propionyl-methionine sulfone
2(S)-[2(S)-(Imidazol-4-ylacetyl)amino-3(S)-methylpentyloxy]-3-(1-naphthyl)propionyl-methionine sulfone methyl ester
2(S)-[2(S)-(Imidazol-4-ylacetyl)amino-3(S)-methylpentyloxy]-3-(1-naphthyl)propionyl-methionine sulfone
2(S)-[2(S)-(Imidazol-4-ylacetyl)amino-3(S)-methylpentyloxy]-3-(2-naphthyl)propionyl-methionine sulfone methyl ester
2(S)-[2(S)-(Imidazol-4-ylacetyl)amino-3(S)-methylpentyloxy]-3-(2-naphthyl)propionyl-methionine sulfone
N-[2(S)-(L-pyroglutamyl)amino-3(S)-methylpentyl]-N-(3-quinolyl-methyl)glycyl-methionine methyl ester
N-[2(S)-(L-pyroglutamyl)amino-3(S)-methylpentyl]-N-(3-quinoly-lmethyl)glycyl-methionine
N-(Benzyl)-N-[2(S)-(tetrazol-1-ylacetyl)amino-3(S)-methylpentyl]-glycyl-methionine methyl ester
N-(Benzyl)-N-[2(S)-(tetrazol-1-ylacetyl)amino-3(S)-methylpentyl]-glycyl-methionine
N-(Benzyl)-N-[2(S)-nicotinoylamino-3(S)-methylpentyl]-glycyl-methionine methyl ester
N-(Benzyl)-N-[2(S)-nicotinoylamino-3(S)-methylpentyl]-glycyl-methionine
N-[2(S)-(L-Pyroglutamyl)amino-3(S)-methylpentyl]-N-(1-naphthylmethyl)-glycyl-methionine sulfoxide methyl ester
N-[2(S)-(L-Pyroglutamyl)amino-3(S)-methylpentyl]-N-(1-naphthylmethyl)-glycyl-methionine sulfoxide
2(S)-{2(S)-[2(S,R)-(Imidazol-4-yl)-2-aminoacetyl)amino]-3(S)-methylpentyloxy}-3-phenylpropionyl-methionine sulfone methyl ester
2(S)-{2(S)-[2(S,R)-(Imidazol-4-yl)-2-aminoacetyl)amino]-3(S)-methylpentyloxy}-3-phenylpropionyl-methionine sulfone
2(S)-{2(S)-[2(R,S)-(Imidazol-4-yl)-2-aminoacetyl)amino]-3(S)-methylpentyloxy}-3-phenylpropionyl-methionine sulfone methyl ester
2(S)-{2(S)-[2(R,S)-(Imidazol-4-yl)-2-aminoacetyl)amino]-3(S)-methylpentyloxy}-3-phenylpropionyl-methionine sulfone
N-{2(S)-[2(S,R)-(Imidazol-4-yl)-2-aminoacetyl]amino-3(S)-methyl-pentyl}-N-(1-naphthylmethyl)-glycyl-methionine methyl ester
N-{2(S)-N[2(S,R)-(Imidazol-4-yl)-2-aminoacetyl] amino-3(S)-methylpentyl)}-N-(1-naphthylmethyl)-glycyl-methionine
N-1{2(S)-[2(R,S)-(Imidazol-4-yl)-2-amninoacetyl]amino-3(S)-methyl-pentyl}-N-(1-naphthylmethyl)-glycyl-methionine methyl ester
N-{2(S)-[2(R,S)-(Imidazol-4-yl)-2-aminoacetyl]amino-3(S)-methylpentyl}-N-(1-naphthylmethyl)-glycyl-methionine
N-{2(S)-[(Imidazol-4-yl)methyl]amino-3(S)-methylpentyl}-N-(1-naphthylmethyl)-glycyl-methionine methyl ester
N-{2(S)-[(Imidazol-4-yl)methyl]amino-3(S)-methylpentyl}-N-(1-naphthylmethyl)-glycyl-methionine
N-[2(S)-(L-pyroglutamyl)amino-3(S)-methylpentyl]-N-(1-naphthylmethyl)glycyl-methionine isopropyl ester
N-[2(S)-(L-pyroglutamyl)amino-3(S)-methylpentyl]-N-(1-naphthylmethyl)glycyl-methionine t-butyl ester
N-[2(S)-(L-pyroglutamyl)amino-3(S)-methylpentyl]-N-(4-quinolyl-methyl)glycyl-methionine methyl ester
N-[2(S)-(L-pyroglutamyl)amino-3(S)-methylpentyl]-N-(4-quinolyl-methyl)glycyl-methionine
N-{2(S)-[3-(Imidazol-4-yl)propyl]amino-3(S)-methylpentyl}-N-(1-naphthylmethyl)glycyl-methionine methyl ester
N-{2(S)-[3-(Imidazol-4-yl)propyl]amino-3(S)-methylpentyl}-N-(1-naphthylmethyl)glycyl-methionine
N-[2(S)-(L-pyroglutamyl)amino-3(S)-methylpentyl]-N-(1-naphthylmethyl)glycyl-norleucine
N-[2(S)-(L-pyroglutamyl)amino-3(S)-methylpentyl]-N-(1-naphthylmethyl)glycyl-norleucine methyl ester
N-[2(S)-(L-pyroglutamyl)amino-3(5)-methylpentyl]-N-(-naphthylmethyl)glycyl-glutamine
N-[2(S)-(L-pyroglutamyl)amino-3(S)-methylpentyl]-N-(1-naphthylmethyl)glycyl-glutamine t-butyl ester
N-[2(S)-(L-pyroglutamyl)amino-3(S)-methylpentyl]-N-[5-(dimethylamino)naphthylsulfonyl]glycyl-methionine methyl ester
N-[2(S)-(3-pyridylmethyl)amino-3(S)-methylpentyl]-N-(1-naphthylmethyl)glycyl-methionine
2{(S)-2(S)-[2-(Imidazol-4-yl)etyl]amino-3(S)-methylpentyloxy}-3-phenylpropionyl-methionine sulfone methyl ester 2(S)-{2(S)-[2-(Imidazol-4-yl)ethyl]amino-3(S)-methylpentyloxy}-3-phenylpropionyl-methionine sulfone N-[2(S)-(L-pyroglutamyl)amino-3(S)-methylpentyl]-N-(1-naphthylmethyl)glycyl-serine methyl ester N-[2(S)-(L-pyroglutamyl)amino-3(S)-methylpentyl]-N-(1-naphthylmethyl)glycyl-(D,L)-serine N-[2(S)-(L-pyroglutamyl)amino-3(S)-methylpentyl]-N-(1-naphthylmethyl)glycyl-(L,D)-serine N-[2(S)-(L-pyroglutamyl)amino-3(S)-methylpentyl]-N-(1-naphthylmethyl)glycyl-homoserine lactone N-[2(S)-(L-pyroglutamyl)amino-3(S)-methylpentyl]-N-(1-naphthylmethyl)glycyl-homoserine N-[2(S)-(L-pyroglutamyl)amino-3(S)-methylpentyl]-N-(cinnamyl)-glycyl-methionine methyl ester N-[2(S)-(L-pyroglutamyl)amino-3(S)-methylpentyl]-N-(cinnamyl)-glycyl-methionine N-{2(S)-[2-(Imidazol-4-yl)ethyl]amino-3(S)-methylpentyl}-N-(1-naphthylmethyl)glycyl-methionine methyl ester N-{2(S)-[2-(Imidazol-4-yl)ethyl]amino-3(S)-methylpentyl}-N-(1-naphthylmethyl)glycyl-methionine N-[2(S)-(L-pyroglutamyl)amino-3(S)-methylpentyl]-N-(1-naphthylmethyl)glycyl-alanine methyl ester N-[2(S)-(L-pyroglutamyl)amino-3(S)-methylpentyl]-N-(1-naphthylmethyl)glycyl-alanine N-[2(S)-(D-pyroglutamyl)amino-3(S)-methylpentyl]-N-(1-naphthylmethyl)glycyl-methionine methyl ester N-[2(S)-(D-pyroglutamyl)amino-3(S)-methylpentyl]-N-(1-naphthylmethyl)glycyl-methionine 2(S)-[2(S)-(L-Pyroglutamyl)amino-3(S)-methylpentyloxy]-3-phenyl-propionyl-methionine sulfone methyl ester 2(S)-[2(S)-(L-Pyroglutamyl)amino-3(S)-methylpentyloxy]-3-phenyl-propionyl-methionine sulfone N-[2(S)-(L-pyroglutamyl)amino-3(S)-methylpentyl]-N-(2,3-methyl-enedioxybenzyl)glycyl-methionine methyl ester N-[2(S)-(L-pyroglutamyl)amino-3(S)-methylpentyl]-N-(2,3-methylenedioxybenzyl)glycyl-methionine N-[2(S)-(Imidazol-4-ylacetyl)amino-3(S)-methylpentyl]-N-(2,3-dihydrobenzofuran-7-ylmethyl)glycyl-methionine methyl ester N-[2(S)-(Imidazol-4-ylacetyl)amino-3(S)-methylpentyl]-N-(2,3-dihydrobenzofuran-7-ylmethyl)glycyl-methionine N-{2(S)-[3-(3-indolyl)propionyl]amino-3(S)-methylpentyl}-N-(1-naphthylmethyl)glycyl-methionine methyl ester N-{2(S)-[3-(3-indolyl)propionyl]amino-3(S)-methylpentyl}-N-(1-naphthylmethyl)glycyl-methionine N-{2(S)-[3-(1-indolyl)propionyl]amino-3(S)-methylpentyl}-N-(1-naphthylmethyl)glycyl-methionine methyl ester N-{2(S)-[3-(1-indolyl)propionyl]amino-3(S)-methylpentyl}-N-(1-naphthylmethyl)glycyl-methionine N-[2(S)-(L-pyroglutamyl)amino-3(S)-methylpentyl]-N-(1-naphthylmethyl)glycyl-histidine methyl ester N-[2(S)-(L-pyroglutamyl)amino-3(S)-methylpentyl]-N-(1-naphthylmethyl)glycyl-histidine N-[2(S)-(L-pyroglutamyl)amino-3(S)-methylpentyl]-N-(cyclopropylmethyl)glycyl-methionine methyl ester N-[2(S)-(L-pyroglutamyl)amino-3(S)-methylpentyl]-N-(cyclopropylmethyl)glycyl-methionine N-[2(S)-(Imidazol-4-ylacetyl)amino-3(S)-methylpentyl]-N-(cyclopropylmethyl)glycyl-methionine methyl ester N-[2(S)-(Imidazol-4-ylacetyl)amino-3(S)-methylpentyl]-N-(cyclopropylmethyl)glycyl-methionine N-[2(S)-(L-pyroglutamyl)amino-3(S)-methylpentyl]-N-(2,3-dihydrobenzofuran-7-ylmethyl)glycyl-methionine methyl ester N-[2(S)-(L-pyroglutamyl)amino-3(S)-methylpentyl]-N-(2,3-dihydrobenzofuran-7-ylmethyl)glycyl-methionine 2(S)-[2(S)-N-(L-Pyroglutamyl)-N-methylamino-3(S)-methylpentyloxy]-3-phenylpropionyl-methionine methyl ester 2(S)-[2(S)-N-(L-Pyroglutamyl)-N-methylamino-3(S)-methylpentyloxy]-3-phenylpropionyl-methionine N-[2(S)-(L-pyroglutamyl)amino-3(S)-methylpentyl]-N-(1-naphthylmethyl)glycyl-O-methylserine methyl ester N-[2(S)-(L-pyroglutamyl)amino-3(S)-methylpentyl]-N-(1-naphthylmethyl)glycyl-O-methylserine N-(1-Naphthylmethyl)-N-[2(S)-(N'-(L-pyroglutamyl)-N'-methylamino)-3(S)-methylpentyl]-glycyl-methionine methyl ester N-(1-Naphthylmethyl)-N-[2(S)-(N'-(L-pyroglutamyl)-N'-methylamino)-3(S)-methylpentyl]-glycyl-methionine N-[1-(Pyroglutamylamino)cyclopent-1-ylmethyl]-N-(1-naphthylmethyl)-glycyl-methionine methyl ester N-[1-(Pyroglutamylamino)-cyclopent-1-ylmethyl]-N-(1-naphthylmethyl)-glycyl-methionine N-[2(S)-(Pyridin-2-on-6-ylcarbonyl)amino-3(S)-methylpentyl]-N-(1-naphthylmethyl)glycyl-methionine methyl ester N-[2(S)-(Pyridin-2-on-6-ylcarbonyl)amino-3(S)-methylpentyl]-N-(1-naphthylmethyl)glycyl-methionine N-[2(S)-(L-pyroglutamyl)amino-3(S)-methylpentyl]-N-(3-chlorobenzyl)glycyl-methionine methyl ester N-[2(S)-(L-pyroglutamyl)amino-3(S)-methylpentyl]-N-(3-chlorobenzyl)glycyl-methionine N-[2(S)-(L-pyroglutamyl)amino-3(S)-methylpentyl]-N-(1-naphthylmethyl)glycyl-O-methylhomoserine methyl ester N-[2(S)-(L-pyroglutamyl)amino-3(S)-methylpentyl]-N-(1-naphthylmethyl)glycyl-O-methylhomoserine N-[2(S)-(L-pyroglutamyl)amino-3(S)-methylpentyl]-N-(2,3-dimethylbenzyl)glycyl-methionine methyl ester N-[2(S)-(L-pyroglutamyl)amino-3(S)-methylpentyl]-N-(2,3-dimethylbenzyl)glycyl-methionine N-[2(S)-(L-pyroglutamyl)amino-3(S)-methylpentyl]-N-(1-naphthylmethyl)glycyl-(2-thienyl)alanine methyl ester N-[2(S)-(L-pyroglutamyl)amino-3(S)-methylpentyl]-N-(1-naphthylmethyl)glycyl-(2-thienyl)alanine N-[2(S)-(pyrrolidin-2-on-1-yl)-3-methylbutanoyl]-isoleucyl-methionine;

N-[2(S)-(piperidin-2-on-1-yl)-3-methylbutanoyl]-isoleucyl-methionine; or the pharmaceutically acceptable salts thereof.

The composition of the instant invention may alternatively comprise a farnesyl pyrophosphate-competitive farnesyl-protein transferase inhibitor. Thus the following compounds, well known in the art, are useful as farnesyl pyrophosphate-competitive inhibitors in the instant invention: bb) U.S. Pat. No. 5,260,465, incorporated herein by reference,

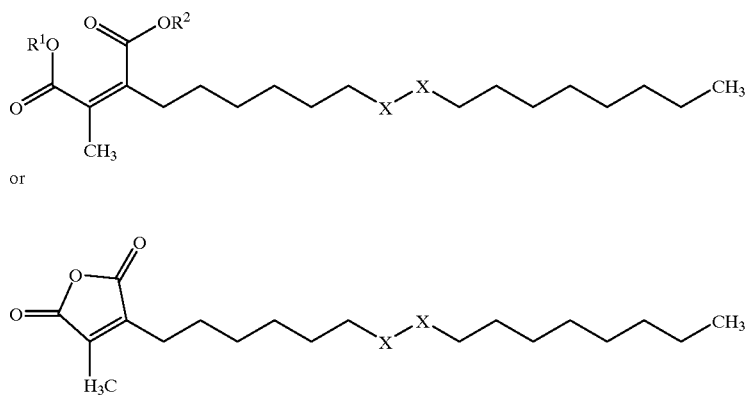

wherein:

X—X is:
- CH=CH (cis);
- CH=CH (trans); or
- CH$_2$CH$_2$;

$R^1$ and $R^2$ are each independently selected from:
a) H;
b) C$_{1-5}$ alkyl;
c) C$_{1-5}$ alkyl substituted with a member of the group consisting of:
 i) phenyl;
 ii) phenyl substituted with methyl, methoxy, halogen (Cl, Br, F, I) or hydroxy;

or a pharmaceutically acceptable salt of a compound of formula (I) in which at least one of $R^1$ and $R^2$ is hydrogen;

cc) U.S. Pat. No. 5,420,157, incorporated herein by reference, wherein:

$R^1$ and $R^2$ are each independently selected from:
a) H;
b) C$_{1-5}$ alkyl;
c) C$_{1-5}$ alkyl substituted with a member of the group consisting of:
 i) phenyl;
 ii) phenyl substituted with methyl, methoxy, halogen (Cl, Br, F, I) or hydroxy;

or a pharmaceutically acceptable salt of a compound of formula (I) in which at least one of $R^1$ and $R^2$ is hydrogen;

dd) U.S. Pat. Nos. 5,245,061 and 5,350,867, incorporated herein by reference,

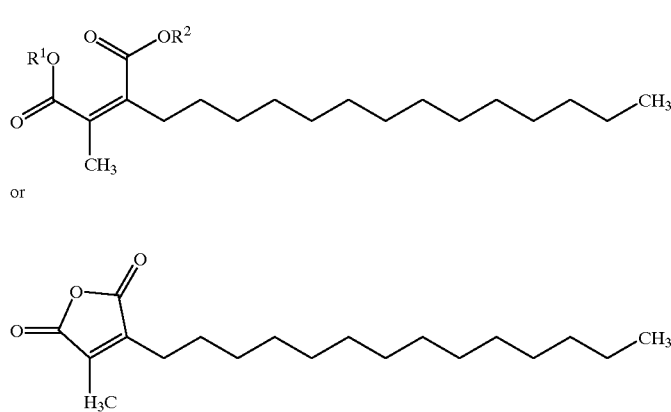

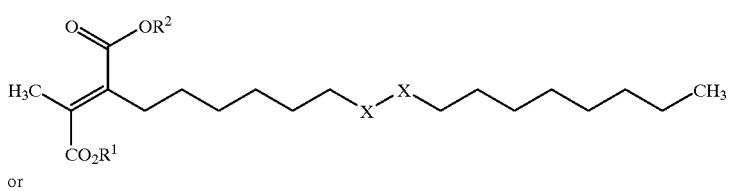

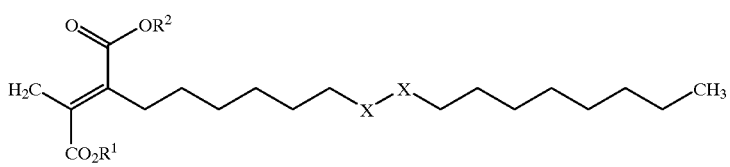

wherein:

X—X is:
CH=CH (cis);
CH=CH (trans); or
$CH_2CH_2$;

$R^1$ and $R^2$ are each independently selected from:
a) H;
b) $C_{1-5}$ alkyl;
c) $C_{1-5}$ alkyl substituted with a member of the group consisting of:
   i) phenyl;
   ii) phenyl substituted with methyl, methoxy, halogen (Cl, Br, F, I) or hydroxy;

or a pharmaceutically acceptable salt of a compound of formula (I) in which at least one of $R^1$ and $R^2$ is hydrogen;

ee) US. Ser. No. 08/459,885, now U.S. Pat. No. 5,661,128 issued Aug. 26, 1997 (Case 19265, filed Jun. 2, 1995); incorporated herein by reference;

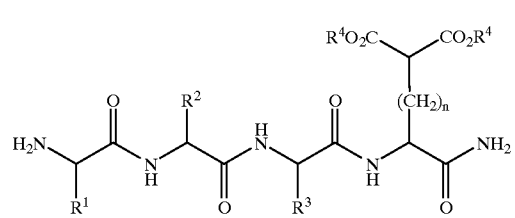

I or the pharmaceutically acceptable salts, hydrates, esters or amides thereof, wherein:

n is: 1 to 4, $R^1$ and $R^3$ independently are $C_{0-4}$ alkyl, substituted with substituents selected from the group consisting of:
a) aryl, which is defined as phenyl or naphthyl, unsubstituted or substituted with one, two, three or four substituents selected from the group consisting of:
   i) F,
   ii) Cl,
   iii) Br,
   iv) nitro,
   v) cyano,
   vi) $C_{1-8}$ alkoxy,
   vii) $C_{1-8}$ alkylthio,
   viii) $C_{1-8}$ alkylsulfonyl,
   ix) sulfamoyl, or
   x) $C_{1-8}$ alkyl; or
b) heteroaryl, which is defined as indolyl, imidazolyl or pyridyl, unsubstituted or substituted with one, two, three or four substituents selected from the group consisting of:
   i) F,
   ii) Cl,
   iii) Br,
   iv) nitro,
   v) cyano,
   vi) $C_{1-8}$ alkoxy,
   vii) $C_{1-8}$ alkylthio,
   viii) $C_{1-8}$ alkylsulfonyl,
   ix) sulfamoyl, or
   x) $C_{1-8}$ alkyl;

$R^2$ is: $C_{0-6}$ alkyl, which is unsubstituted or substituted with a substituent selected from the group consisting of:
a) unsubstituted or substituted aryl, as defined in $R^1$(a),
b) unsubstituted or substituted heteroaryl, as defined in $R^1$(b),
c) $C_{3-8}$ cycloalkyl,
d) $C_{1-8}$ alkylthio,
e) $C_{1-8}$ alkylsulfonyl,
f) $C_{1-8}$ alkoxy, or
g) aryl $C_{1-8}$ alkyl sulfonyl; and $R^4$ is: H;

ff) U.S. Pat. Nos. 5,298,655 and 5,362,906; incorporated herein by reference;

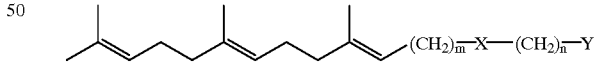

wherein:

X is $CH_2$, CH(OH), C=O, CHCOR, $CH(NH_2)$, CH(NHCOR), O, $S(O)_p$,

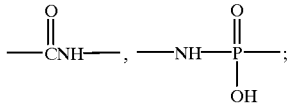

p is 0, 1 or 2;

Y is $PO_3RR^1$ or $CO_2R$;

R is H, lower alkyl, or $CH_2CH_2N^+Me_3A^-$;

$R^1$ is H, lower alkyl, or $CH_2CH_2N^+Me_3A^-$;

A is a pharmaceutically acceptable anion;
m is 0, 1, 2, or 3; and
n is 0, 1, 2, or 3;
or the pharmaceutically acceptable salts thereof.

Specific examples of farnesyl pyrophosphate-competitive inhibitors include:
3-Hydroxy-7,11,15-trimethylhexadeca-6,10,14-trienoic acid,
[2-Oxo-6,10,14-trimethylpentadeca-5,9,13-trienyl] phosphonic acid
[2-Hydoxy-6,10,14-trimethylpentadeca-5,9,13-trienyl] phosphonic acid
[1-Acetyl-4,8,12-trimethylpentadeca-3,7,11-trienyl] phosphonic acid
[2-[(E,E)-3,7,11-Trimethyl-2,6,10-dodecatrienylamino]-2-oxo-ethyl]phosphonic acid
[(E,E)-4,8,12-Trimethyl-3,7,11-tridecatrienyl]thiomethyl-phosphonic acid
3-[(E,E)-3,7,11-Trimethyl-2,6,10-dodecatrienylamino]-3-oxo-propionic acid
2-[(E,E)-3,7,11-Trimethyl-2,6,10-dodecatrienylamino]-2-oxo-ethyl]phosphonic acid monomethyl ester
[2-[(E,E)-3,7,11-Trimethyl-2,6,10-dodecatrienylamino]-1-oxo-methyl]phosphonic acid
[1-Hydroxy-(E,E)-3,7,11-trimethyl-2,6,10-dodecatrienyl]-phosphonic acid
[1-Hydroxy-(E,E)-5,9,13-trimethyl-4,8,12-tetradecatrienyl]-phosphonic acid
[1-Hydroxy-(E,E)-4,8,12-trimethyl-3,7,11-tridecatrienyl]-phosphonic acid
[2-Acetamido-(E,E)-4,8,12-trimethyl-3,7,11-tridecatrienyl]-phosphonic acid and
[2-Hydroxy-(E,E)-4,8,12-trimethyl-3,7,11-tridecatrienyl]-phosphonic acid
or a pharmaceutically acceptable salt.

The composition of the instant invention may alternatively a farnesyl pyrophosphate-competitive inhibitor obtained by fermentation of cultures of novel organisms. In particular, the compounds disclosed in the following patent may be useful as a farnesyl pyrophosphate-competitive inhibitor component of the instant composition: U.S. Ser. No. 08/254,228. That patent is incorporated herein by reference.

In addition, compounds described in the following patents and publications may also be utilized as a farnesyl pyrophosphate-competitive inhibitor component of the instant composition: European Pat. Publ. 0 537 008; European Pat. Publ. 0 540 782; PCT Pat. Publs. WO 94/1935; WO 95/12572 ; and WO 95/08546. Those patents and publications are incorporated herein by reference.

The protein substrate-competitive inhibitors and farnesyl pyrophosphate-competitive inhibitors of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereo-configuration As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6\ alkyl)_2$, $NO_2$, CN, $(C_1-C_6\ alkyl)O$—, —OH, $(C_1-C_6\ alkyl)S(O)_m$—, $(C_1-C_6\ alkyl)C(O)NH$—, $H_2N$—C(NH)—, $(C_1-C_6\ alkyl)C(O)$—, $(C_1-C_6\ alkyl)OC(O)$—, $N_3$, $(C_1-C_6\ alkyl)OC(O)NH$— and $C_1-C_{20}$ alkyl.

The following structure:

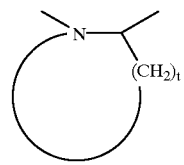

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

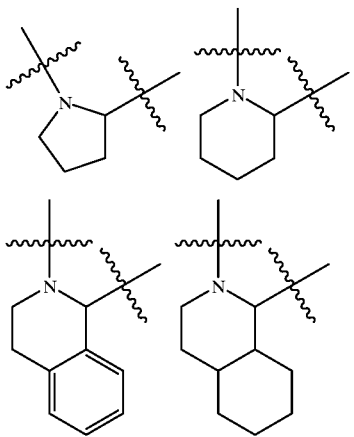

It is also understood that substitution on the cyclic amine moiety by $R^{2a}$, $R^{2b}$, $R^{7a}$ and $R^{7b}$ may be on different carbon atoms or on the same carbon atom.

When $R^{2a}$ and $R^{2b}$, and $R^3$ and $R^4$ are combined to form —(CH$_2$)$_s$—, cyclic moieties are formed. Examples of such cyclic moieties include, but are not limited to:

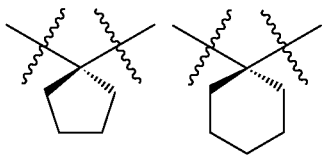

When $R^{5a}$ and $R^{5b}$ are combined to form —(CH$_2$)$_s$—, cyclic moieties as described hereinabove for $R^3$ and $R^4$ are formed. In addition, such cyclic moieties may optionally include a heteroatom(s). Examples of such heteroatom-containing cyclic moieties include, but are not limited to:

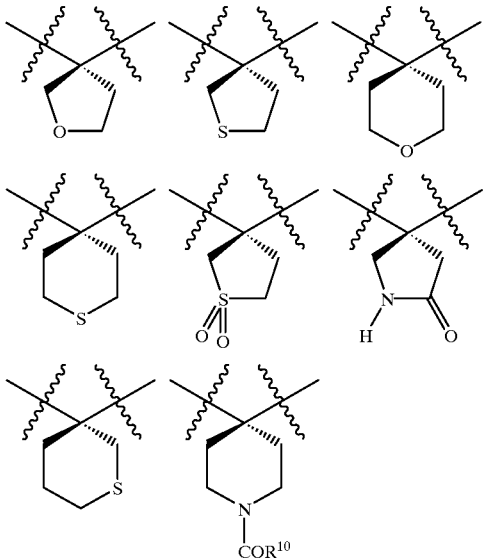

As used herein, the phrase "nitrogen containing $C_4$–$C_9$ mono or bicyclic ring system wherein the non-nitrogen containing ring may be a $C_6$ aromatic ring, a $C_5$–$C_7$ saturated ring or a heterocycle" which defines moiety "Q" of the instant invention includes but is not limited to the following ring systems:

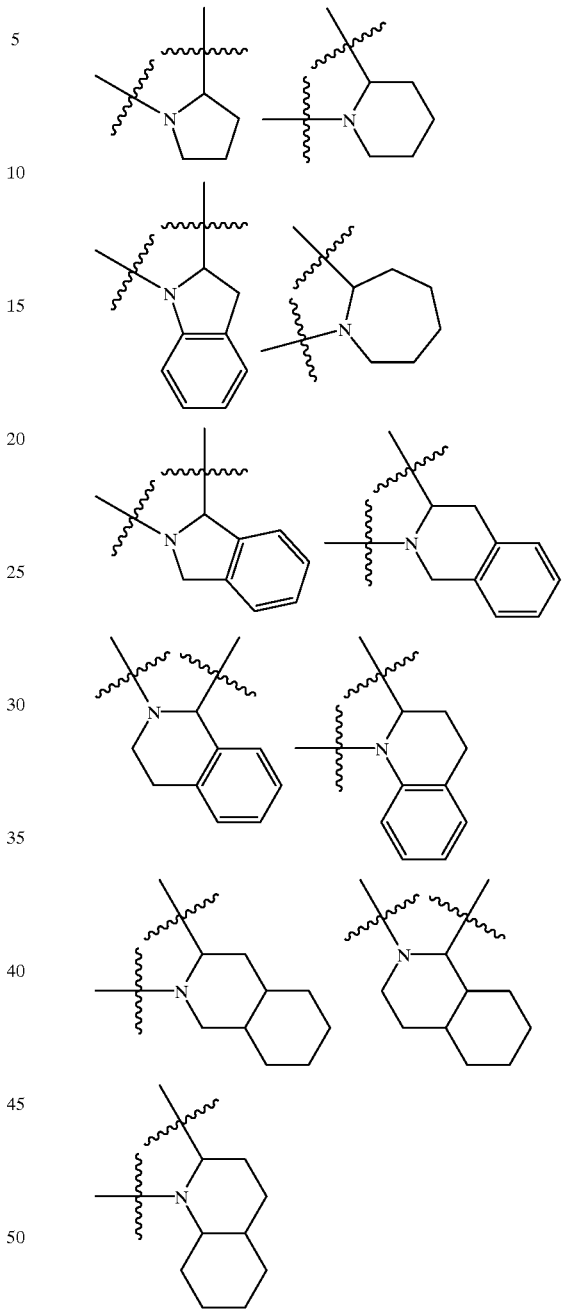

It is intended that the definition of any substituent or variable (e.g., $R^{10}$, Z, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the protein substrate-competitive inhibitors and farnesyl pyrophosphate-competitive inhibitors of the instant invention can be selected by one of ordinary skill in the art to provide compounds that are chemically stable and that can be readily synthesized by techniques known in the art as well as those methods set forth below.

The pharmaceutically acceptable salts of the protein substrate-competitive inhibitors and farnesyl pyrophosphate-competitive inhibitors of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the protein substrate-competitive inhibitors and farnesyl pyrophosphate-competitive inhibitors of this invention can be synthesized from the corresponding inhibitor of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Some of the protein substrate-competitive inhibitors and farnesyl pyrophosphate-competitive inhibitors of the invention can be synthesized from their constituent amino acids by conventional peptide synthesis techniques, and the additional methods described below. Standard methods of peptide synthesis are disclosed, for example, in the following works: Schroeder et al., "The Peptides", Vol. 1, Academic Press 1965, or Bodanszky et al., "Peptide Synthesis", Interscience Publishers, 1966, or McOmie (ed.) "Protective Groups in Organic Chemistry38 , Plenum Press, 1973, or Barany et al., "The Peptides: Analysis, Synthesis, Biology" 2,Chapter 1, Academic Press, 1980, or Stewart et al., "Solid Phase Peptide Synthesis", Second Edition, Pierce Chemical Company, 1984. Also useful in exemplifying syntheses of specific unnatural amino acid residues are European Pat. Appl. No. 0 350 163 A2(particularly page 51–52) and J. E. Baldwin et al. Tetrahedron, 50:5049–5066 (1994). With regards to the synthesis of instant compounds containing a (β-acetylamino)alanine residue at the C-terminus, use of the commercially available $N_\alpha$-Z-L-2,3-diaminopropionic acid (Fluka) as a starting material is preferred. The teachings of these works are hereby incorporated by reference.

Abbreviations used in the description of the chemistry and in the Examples that follow are:
$Ac_2O$ Acetic anhydride;
Boc t-Butoxycarbonyl;
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimide-hydrochloride;
HOBT 1-Hydroxybenzotriazole hydrate;
$Et_3N$ Triethylamine;
EtOAc Ethyl acetate;
FAB Fast atom bombardment;
HOOBT 3-Hydroxy-1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide;
Py Pyridine;
TFA Trifluoroacetic acid;
THF Tetrahydrofuran.

The protein substrate-competitive inhibitors of this invention designated "v" hereinabove are prepared by employing the reactions shown in the following Reaction Schemes A–R, in addition to other standard manipulations such as ester hydrolysis, cleavage of protecting groups, etc., as may be known in the literature or exemplified in the experimental procedures. Such Reaction Schemes are also useful in preparing other protein substrate-competitive inhibitors and farnesyl pyrophosphate-competitive inhbitors. For example, Reaction Schemes A–E are especially useful in preparing the inhibitors designated "a)" through "k)", "m)", "n)", "q)" through "u)" and "ee)" hereinabove. Some key bond-forming and peptide modifying reactions are:

Reaction A Amide bond formation and protecting group cleavage using standard solution or solid phase methodologies.

Reaction B Preparation of a reduced peptide subunit by 1reductive alkylation of an amine by an aldehyde using sodium cyanoborohydride or other reducing agents.

Reaction C Alkylation of a reduced peptide subunit with an alkyl or aralkyl halide or, alternatively, reductive alkylation of a reduced peptide subunit with an aldehyde using sodium cyanoborohydride or other reducing agents.

Reaction D Peptide bond formation and protecting group cleavage using standard solution or solid phase methodologies.

Reaction E Preparation of a reduced subunit by borane reduction of the amide moiety.

Reaction Schemes A–E illustrate bond-forming and peptide modifying reactions incorporating acyclic peptide units. It is well understood that such reactions are equally useful when the —NHC($R^4$)— moiety of the reagents and compounds illustrated is replaced with the following moiety:

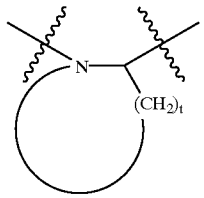

These reactions may be employed in a linear sequence to provide the compounds of the invention or they may be used to synthesize fragments which are subsequently joined by the alkylation reactions described in the Reaction Schemes.

REACTION SCHEME A

Reaction A. Coupling of residues to form an amide bond

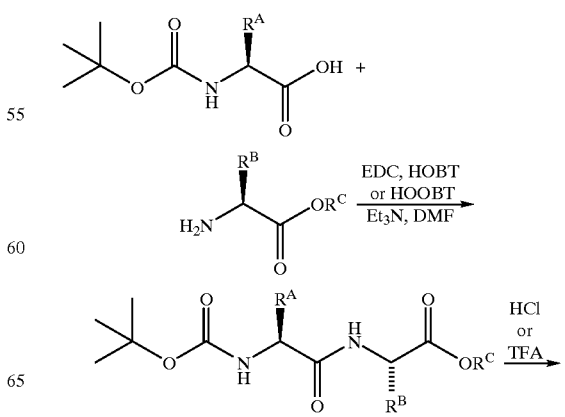

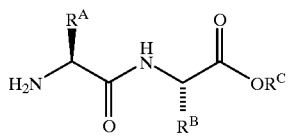

REACTION SCHEME B

Reaction B. Preparation of reduced peptide subunits by reductive alkylation

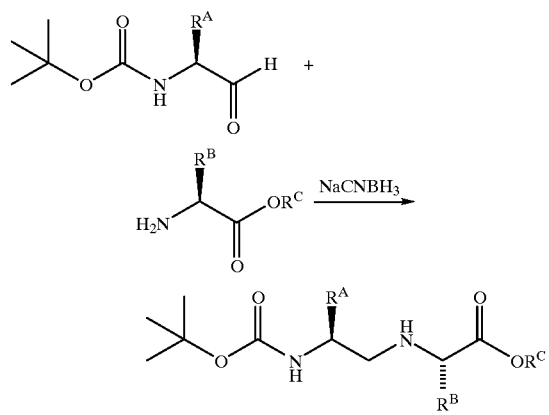

REACTION SCHEME C

Reaction C. Alkylation/reductive alkylation of reduced peptide subunits

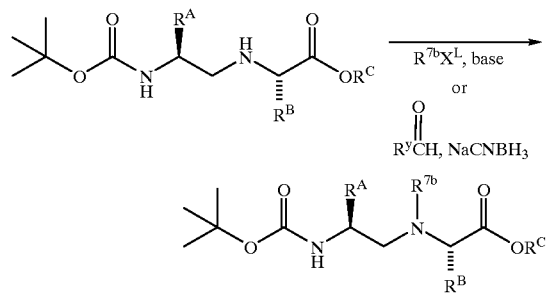

REACTION SCHEME D

Reaction D. Coupling of residues to form an amide bond

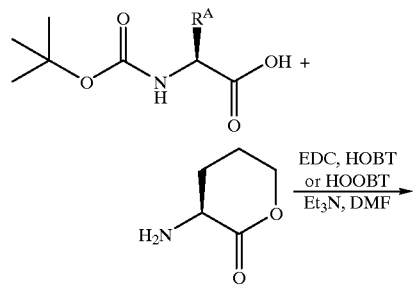

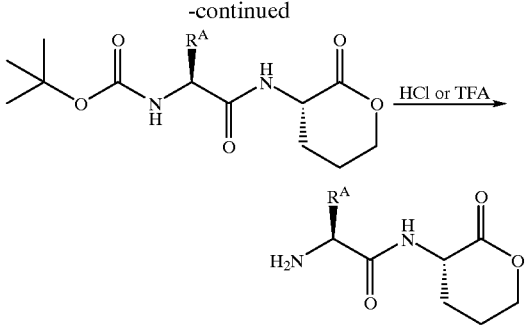

REACTION SCHEME E

Reaction E. Preparation of reduced dipeptides from peptides

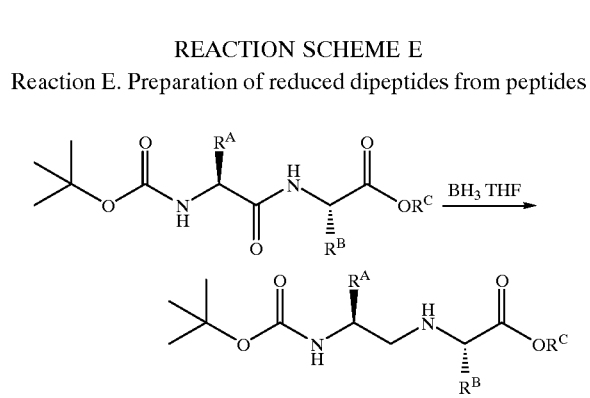

where $R^A$ and $R^B$ are $R^3$, $R^4$, $R^{5a}$ or $R^{5b}$ as previously defined; $R^C$ is $R^6$ as previously defined or a carboxylic acid protecting group; $X^L$ is a leaving group, e.g., $Br^-$, $I^-$ or $MsO^-$; and $R^y$ is defined such that $R^{7b}$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. For simplicity, substituents $R^{2a}$ and $R^{2b}$ on the cyclic amine moiety are not shown. It is, however, understood that the reactions illustrated are also applicable to appropriately substituted cyclic amine compounds. The key reactions are: stereoselective reduction of the Boc-amino-enone to the corresponding syn amino-alcohol (Scheme F, Step B, Part 1), and stereospecific boron triflouride or zinc chloride activated organomagnesio, organo-lithio, or organo-zinc copper(1) cyanide $S_N 2'$ displacement reaction (Scheme F, Step G). Through the use of optically pure N-Boc amino acids as starting material and these two key reactions, the stereo-chemistry of the final products is well defined. In Step H of Scheme F, the amino terminus sidechain, designated $R^x$ is incorporated using coupling reaction A and $R^x$COOH; the alkylation reaction C using $R^x$CHO and a reducing agent; or alkylation reaction C using $R^x CH_2 X^L$. Such reactions as described in Step H are described in more detail in Reaction Schemes J–X hereinbelow.

The alkane analogs are prepared in a similar manner by including an additional catalytic hydrogenation step as outlined in Reaction Scheme G.

REACTION SCHEME F
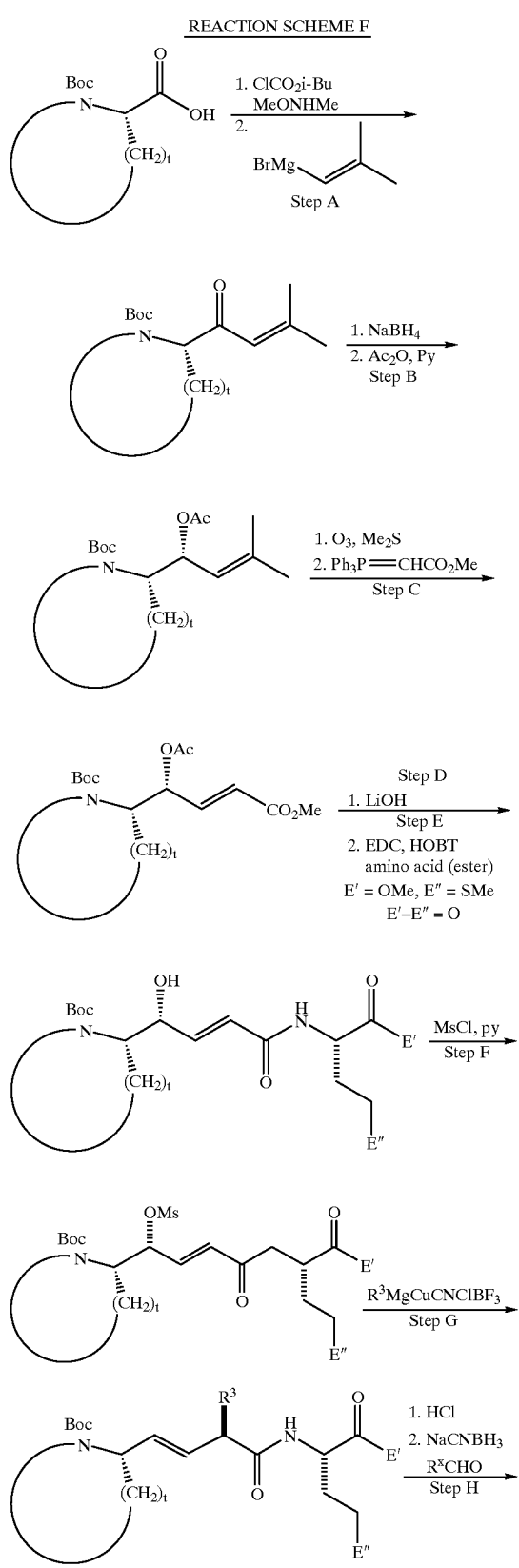
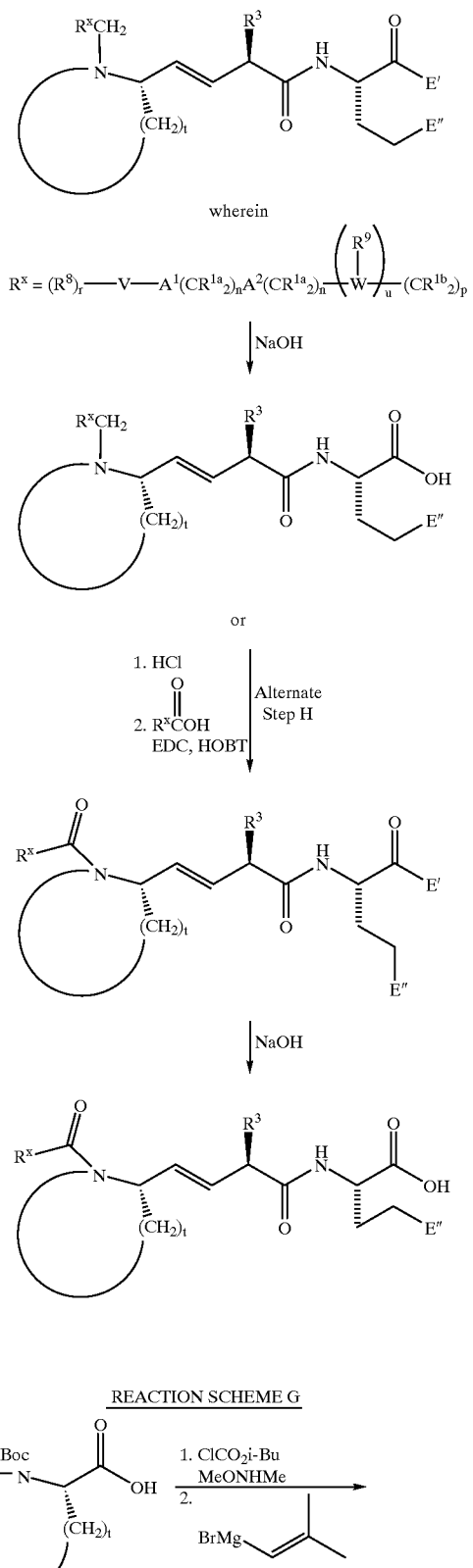
wherein
$R^x = (R^8)_r—V—A^1(CR^{1a}{}_2)_n A^2(CR^{1a}{}_2)_n \left(W\binom{R^9}{}\right)_u (CR^{1b}{}_2)_p$
REACTION SCHEME G

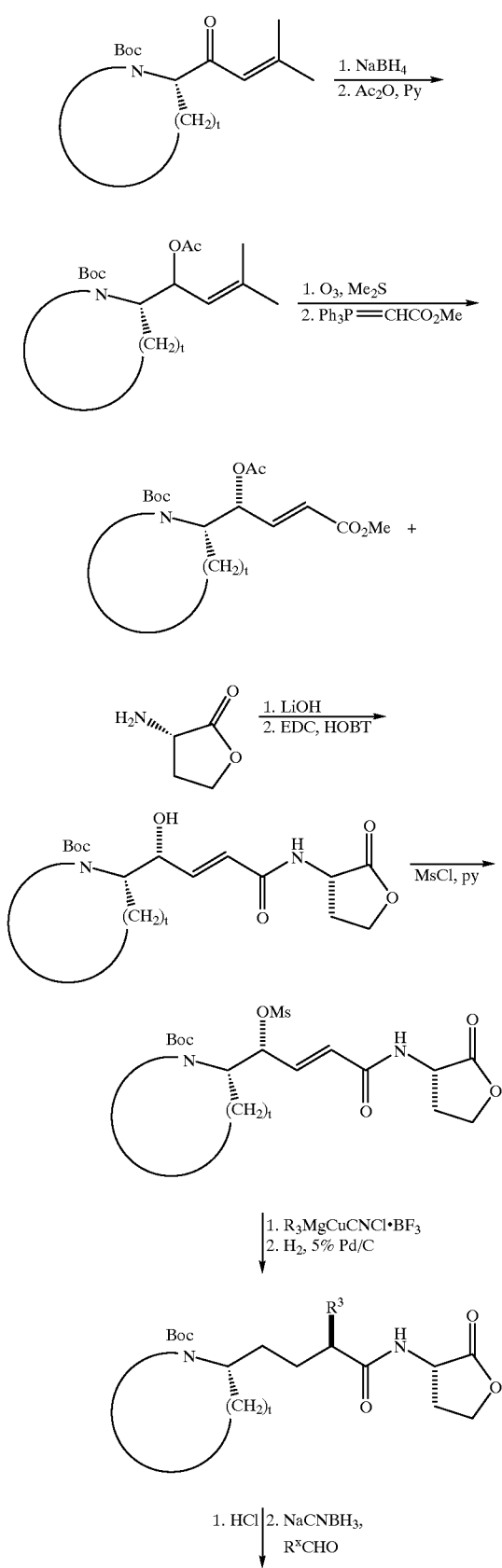
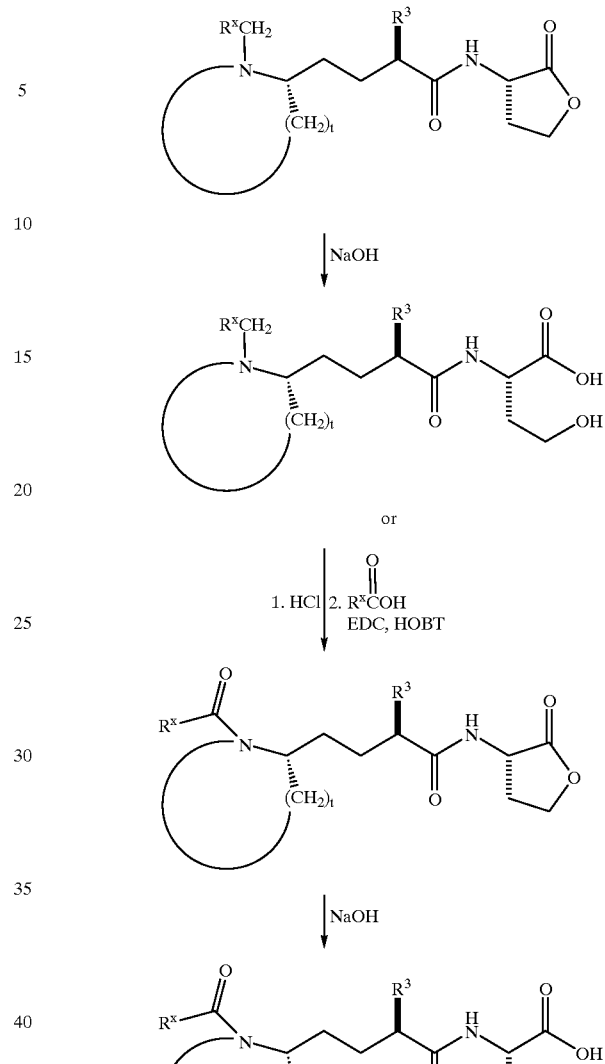

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. Alkylation of 3 with $R^3X^L$, where $X^L$ is a leaving group such as $Br^-$, $I^-$ or $Cl^-$ in THF/DME (1,2-dimethoxyethane) in the presence of a suitable base, preferably NaHMDS [sodium bis(trimethylsilyl)amide], affords 4, which is retreated with NaHMDS followed by either protonation or the addition of an alkyl halide $R^4X$ to give 5a or 5b, respectively, as a enantiomeric mixture. Alternatively, 5a can be prepared from 3 via an aldol condensation approach. Namely, deprotonation of 3 with NaHMDS followed by the addition of a carbonyl compound $R^yR^zCO$ gives the adduct 6. Dehydration of 6 can be effected by mesylation and subsequent elimination catalyzed by DBU (1,8-diazabicyclo[5.4.0]undec-7-ene) or the direct treatment of 6 with phosphorus oxychloride in pyridine to give olefin 7. Then, catalytic hydrogenation of 7 yields 5a (wherein —CHR$^y$R$^z$ constitutes R$^3$). Direct hydrolysis of 5 with lithium hydrogen peroxide in aqueous THF, or aqueous HCl, produces acid 8a. Compound 8a is then derivatized with BOC-ON or BOC anhydride to give 8b. The peptide coupling of acid 8b with either an alpha-aminolactone (e.g., homoserine lactone, etc.) or the ester of an amino acid is carried out under the conditions exemplified in the previously described references to yield derivative 2. Treatment of 2 with gaseous hydrogen chloride gives 10, which undergoes further elaboration as described in Reaction Schemes J—hereinbelow.

An alternative method for the preparation of the prolyl oxa isostere (compounds 23 and 24) is shown in Scheme H-1. Referring to Scheme H-1, the aminoalcohol 1 is protected with trifluoroacetic anhydride and the blocked compound 15 treated with diphenyl disulfide in the presence of tributylphosphine to provide the thioether 16. Chlorination of compound 16 provides compound 17 which can be reacted with the appropriate carboxylic acid alcohol in the presence of silver perchlorate and tin (II) chloride, to afford the mixed acetal 18. Removal of the phenylmercapto moiety with Raney nickel provides compound 19. Compound 19 is doubly deprotected, then selectively BOC protected to provide the acid 20, which undergoes the steps previously described for incorporating terminal amino acid. Still another alternative method for the preparation of the prolyl oxa isostere (compounds 23 and 24) is described in the literature [Ruth E. TenBrink, J. Org. Chem., 52, 418–422 (1987)].

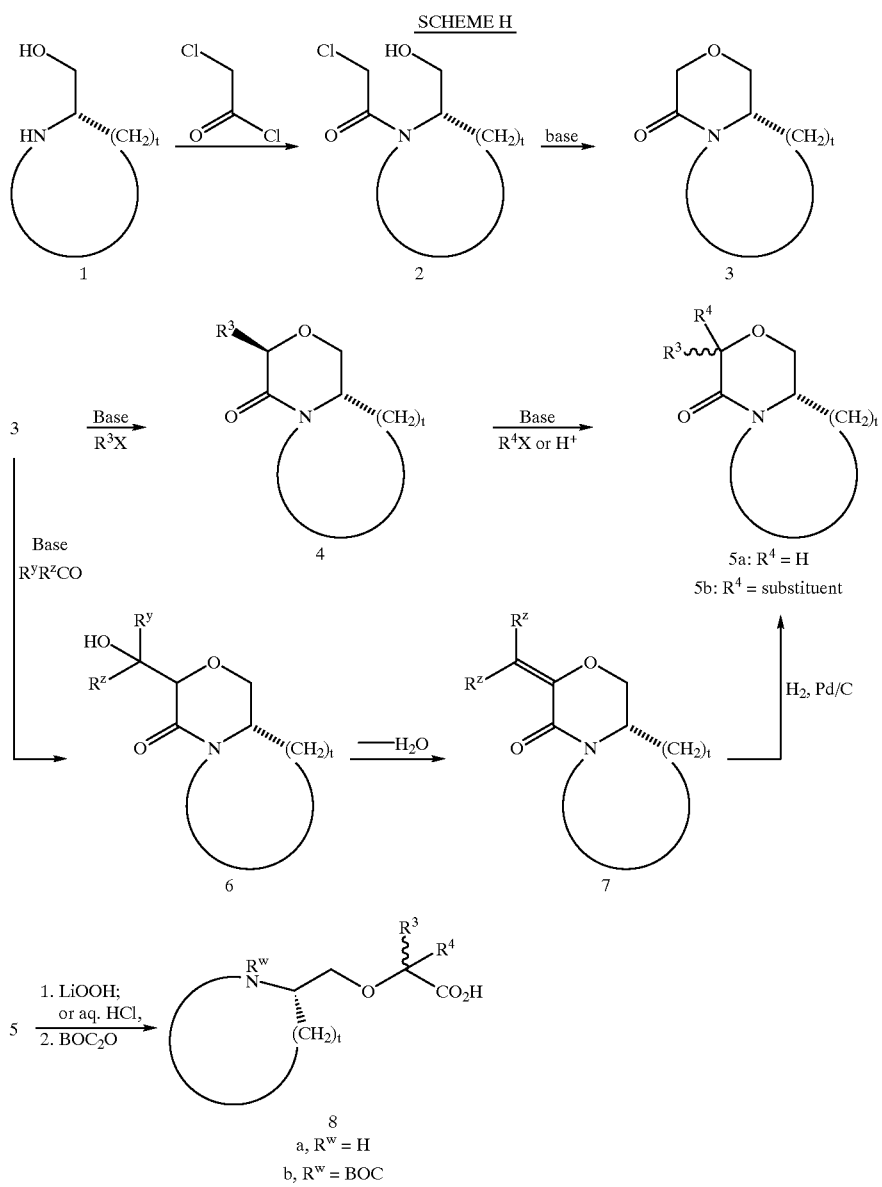

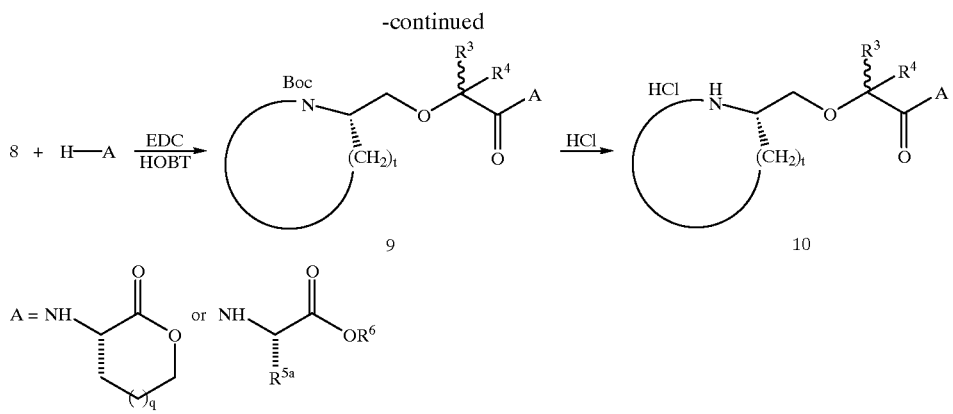
SCHEME H-1
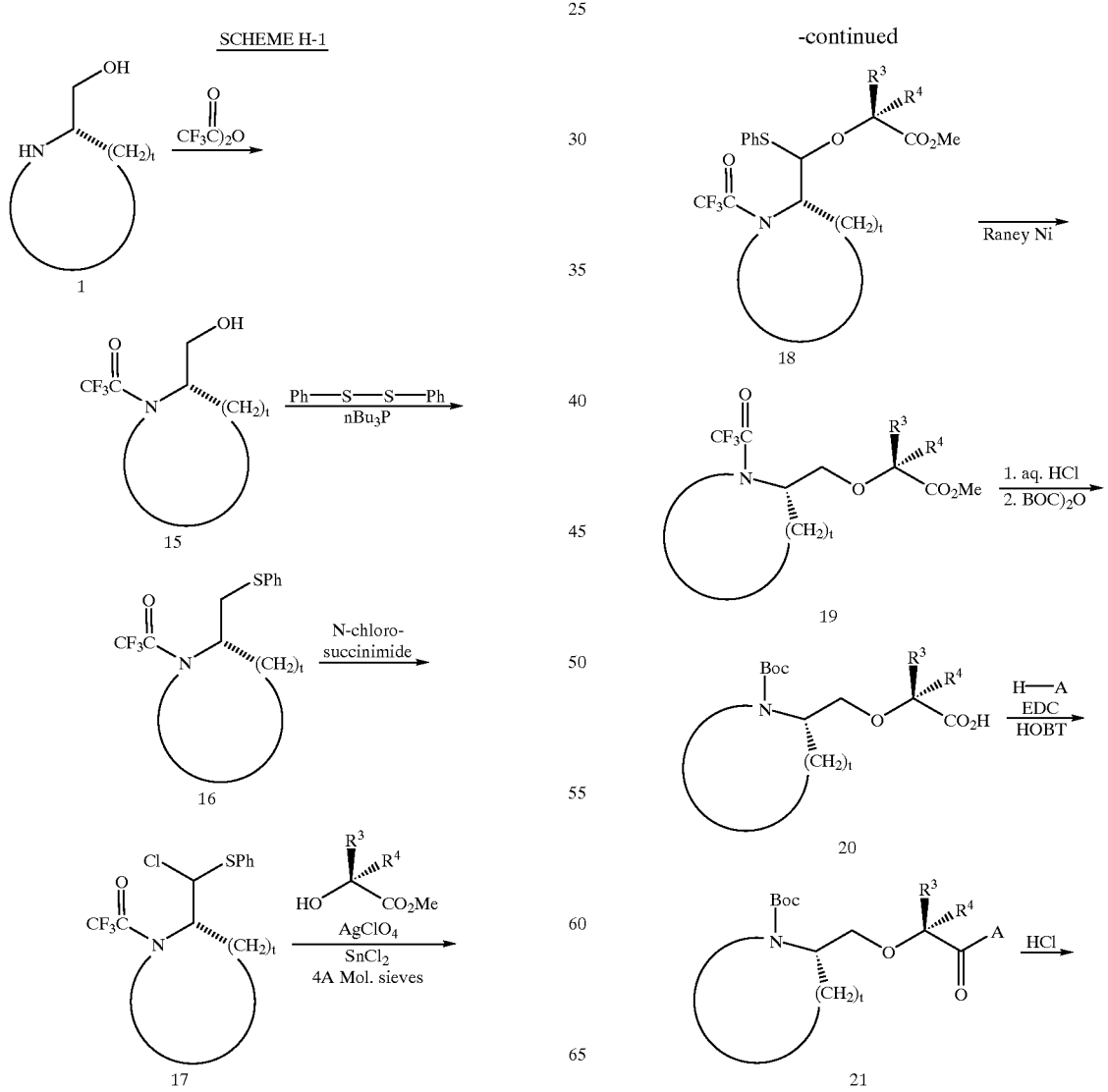

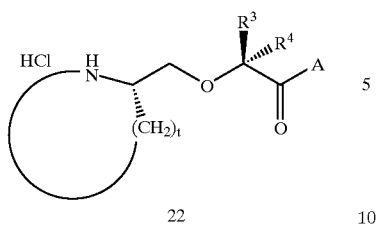

The thia, oxothia and dioxothia isostere compounds of this invention are prepared in accordance to the route depicted in Scheme I. Aminoalcohol 1 is derivatized with BOC$_2$O to give 25. Mesylation of 25 followed by reaction with methyl alpha-mercaptoacetate in the presence of cesium carbonate gives sulfide 26. Removal of the BOC group in 26 with TFA followed by neutralization with di-isopropylethylamine leads to lactam 27. Sequential alkylation of 27 with the alkyl halides R$^3$X and R$^4$X in THF/DME using NaHDMS as the deprotonation reagent produces 28. Hydrolysis of 28 in hydrochloride to yield 29a, which is derivatized with Boc anhydride to yield 29b. The coupling of 29b with an alpha-aminolactone (e.g., homoserine lactone, etc.) or the ester of an amino acid is carried out under conventional conditions as exemplified in the previously described references to afford 30. Sulfide 30 is readily oxidized to sulfone 31 by the use of MCPBA (m-chloroperoxybenzoic acid). The N-BOC group of either 30 or 31 is readily removed by treatment with gaseous hydrogen chloride.

SCHEME I

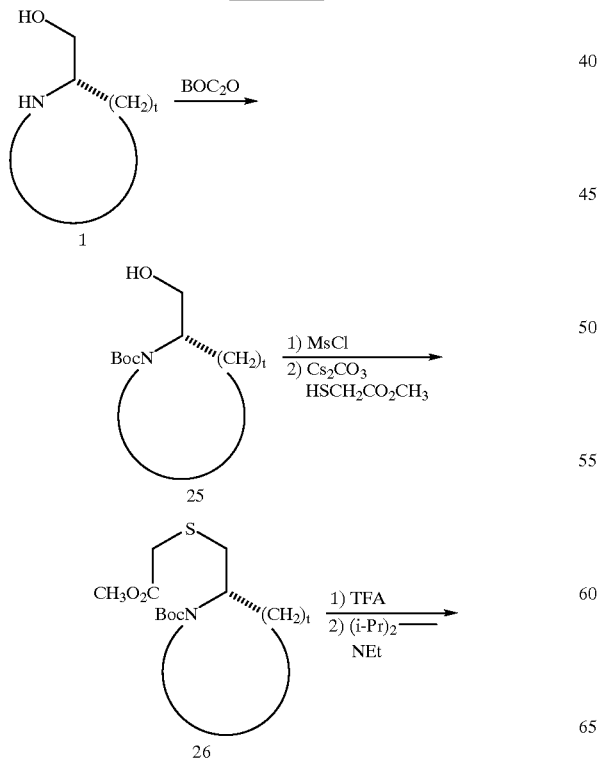

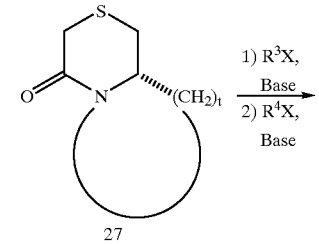

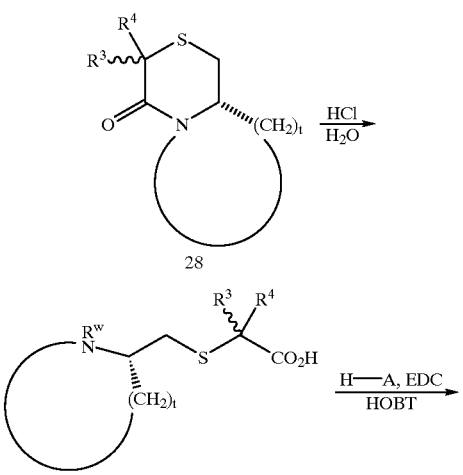

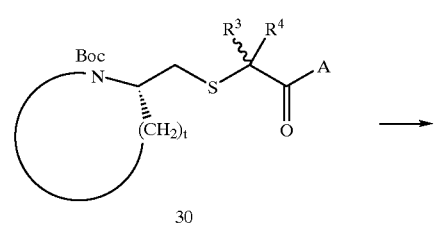

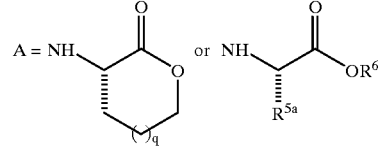

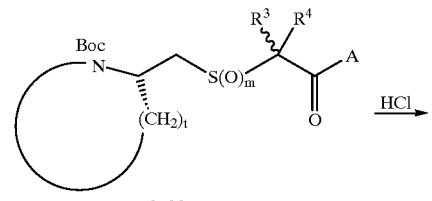

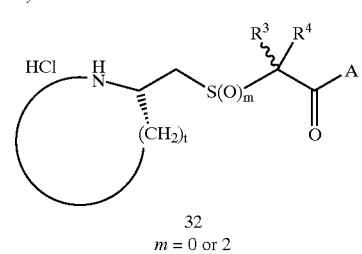

Reaction Schemes J–R illustrate reactions wherein the non-sulfhydryl-containing moiety at the N-terminus of the compounds of the instant invention is attached to the fully elaborated cyclic amino peptide unit, prepared as described in Reaction Schemes A–I. It is understood that the reactions illustrated may also be performed on a simple cyclic amino acid, which may then be further elaborated utilizing reactions described in Reaction Schemes A–I to provide the instant compounds.

The intermediates whose synthesis are illustrated in Reaction Schemes A–I can be reductively alkylated with a variety of aldehydes, such as V, as shown in Reaction Scheme J. The aldehydes can be prepared by standard procedures, such as that described by O. P. Goel, U. Krolls, M. Stier and S. Kesten in *Organic Syntheses,* 1988, 67, 69–75, from the appropriate amino acid (Reaction Scheme F). The reductive alkylation can be accomplished at pH 5–7 with a variety of reducing agents, such as sodium triacetoxyborohydride or sodium cyanoborohydride in a solvent such as dichloroethane, methanol or dimethylformamide. The product VI can be deprotected with trifluoroacetic acid in methylene chloride to give the final compounds VII. The final product VII is isolated in the salt form, for example, as a trifluoroacetate, hydrochloride or acetate salt, among others. The product diamine VII can further be selectively protected to obtain VIII, which can subsequently be reductively alkylated with a second aldehyde to obtain IX. Removal of the protecting group, and conversion to cyclized products such as the dihydroimidazole XI can be accomplished by literature procedures.

Alternatively, the protected cyclic aminopeptidyl intermediate can be reductively alkylated with other aldehydes such as 1-trityl-4-carboxaldehyde or 1-trityl-4-imidazolylacetaldehyde, to give products such as XII (Reaction Scheme K). The trityl protecting group can be removed from XII to give XIII, or alternatively, XII can first be treated with an alkyl halide then subsequently deprotected to give the alkylated imidazole XIV. Alternatively, the dipeptidyl analog intermediate can be acylated or sulfonylated by standard techniques.

The imidazole acetic acid XV can be converted to the protected acetate XVII by standard procedures, and XVII can be first reacted with an alkyl halide, then treated with refluxing methanol to provide the regiospecifically alkylated imidazole acetic acid ester XVIII. Hydrolysis and reaction with the protected dipeptidyl analog intermediate in the presence of condensing reagents such as 1-(3-dimethylaminopropyl)-3-ethylcarbodiimide (EDC) leads to acylated products such as XIX.

If the protected dipeptidyl analog intermediate is reductively alkylated with an aldehyde which also has a protected hydroxyl group, such as XX in Reaction Scheme N. the protecting groups can be subsequently removed to unmask the hydroxyl group (Reaction Schemes N, P). The alcohol can be oxidized under standard conditions to e.g. an aldehyde, which can then be reacted with a variety of organometallic reagents such as Grignard reagents, to obtain secondary alcohols such as XXIV. In addition, the fully deprotected amino alcohol XXV can be reductively alkylated (under conditions described previously) with a variety of aldehydes to obtain secondary amines, such as XXVI (Reaction Scheme P), or tertiary amines.

The Boc protected amino alcohol XXII can also be utilized to synthesize 2-aziridinylmethylpiperazines such as XXVII (Reaction Scheme Q). Treating XXII with 1,1'-sulfonyldiimidazole and sodium hydride in a solvent such as dimethylformamide led to the formation of aziridine XXVII. The aziridine may be reacted in the presence of a nucleophile, such as a thiol, in the presence of base to yield the ring-opened product XXVIII.

In addition, the protected dipeptidyl analog intermediate can be reacted with aldehydes derived from amino acids such as O-alkylated tyrosines, according to standard procedures, to obtain compounds such as XXXIV, as shown in Reaction Scheme R. When R' is an aryl group, XXXIV can first be hydrogenated to unmask the phenol, and the amine group deprotected with acid to produce XXXV. Alternatively, the amine protecting group in XXXIV can be removed, and O-alkylated phenolic amines such as XXXVI produced.

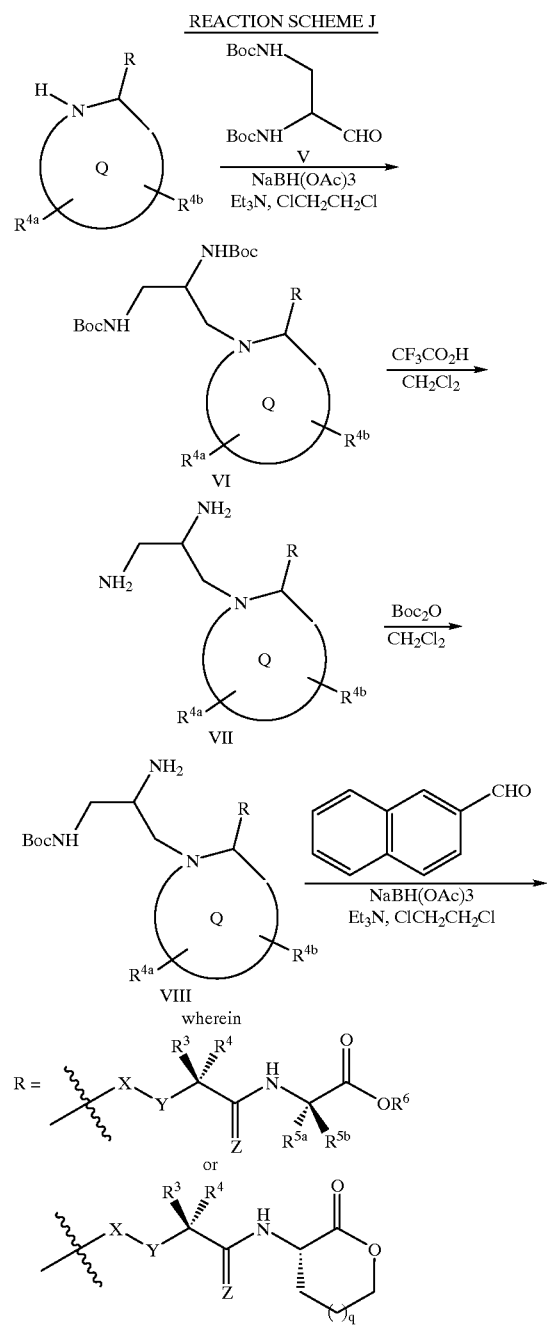

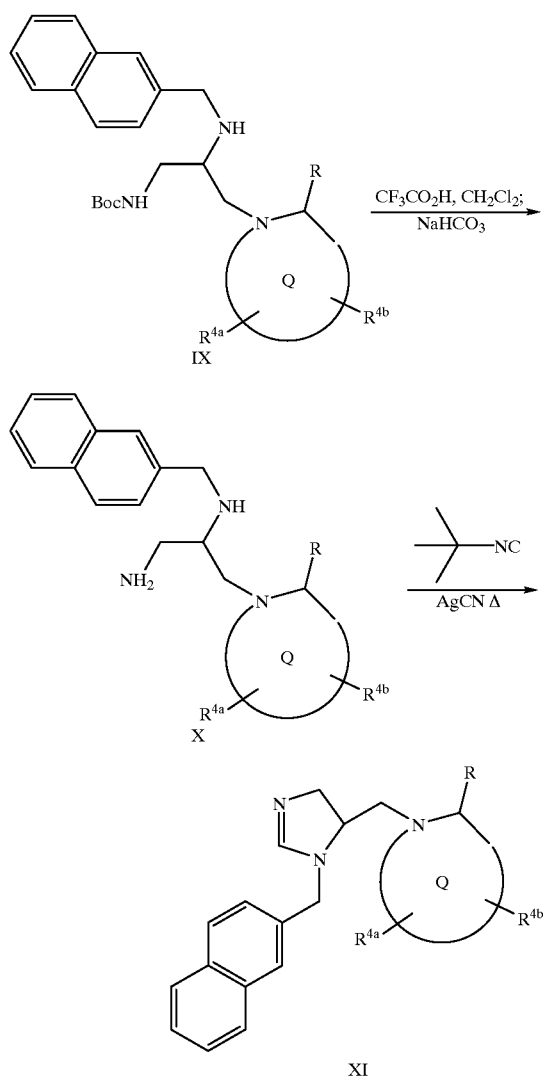
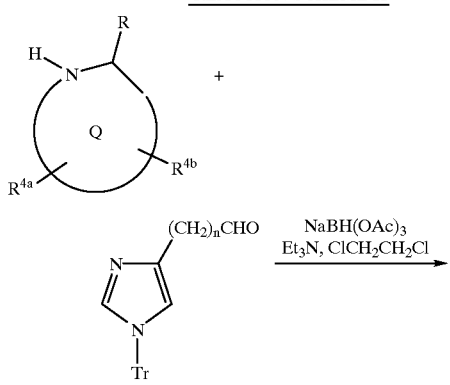
REACTION SCHEME K
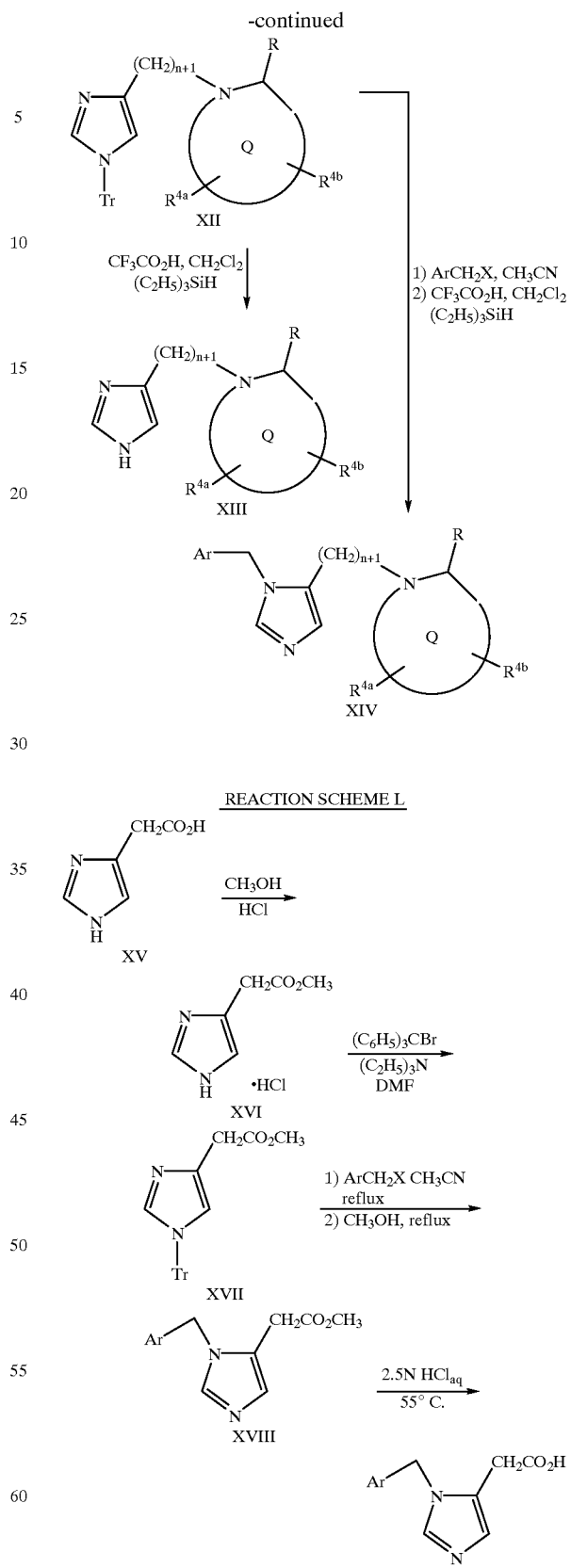
REACTION SCHEME L

REACTION SCHEME M
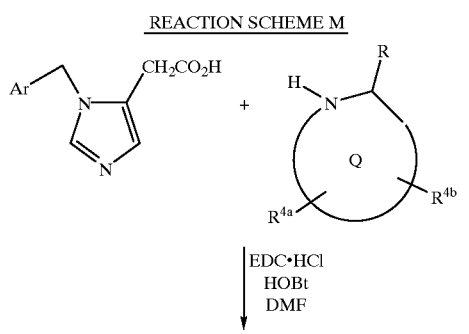
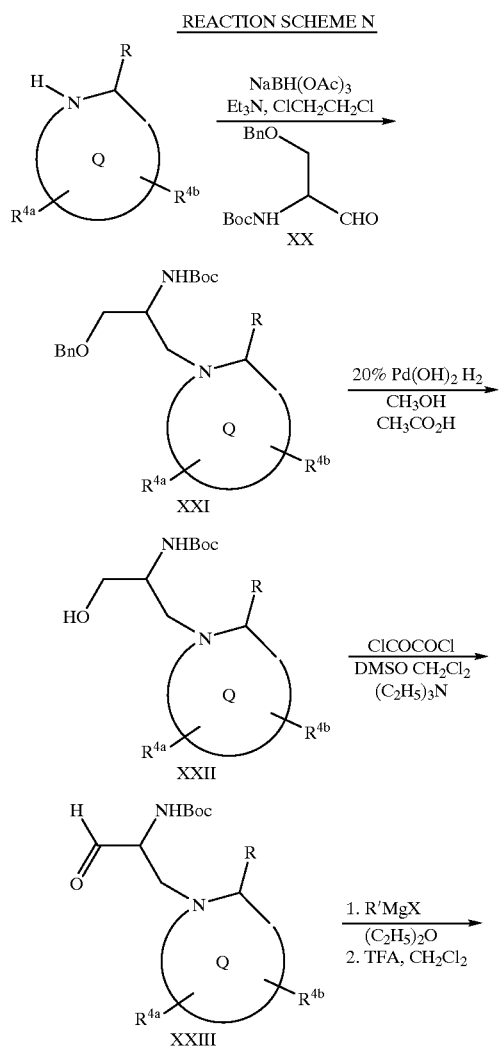
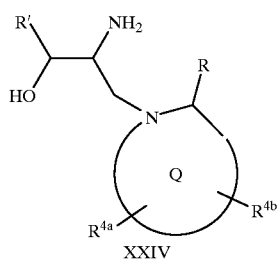
REACTION SCHEME P
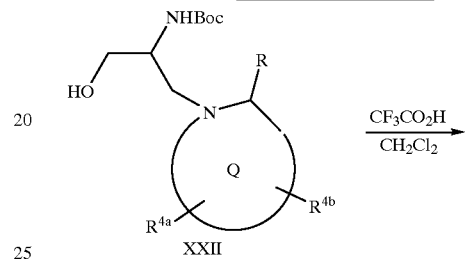
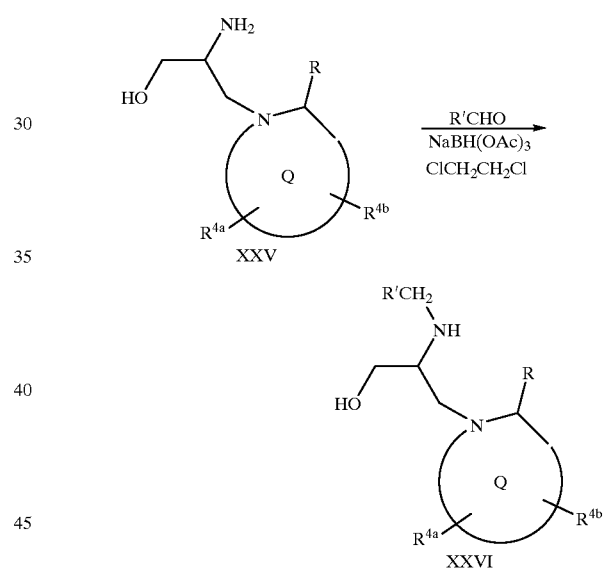
REACTION SCHEME Q
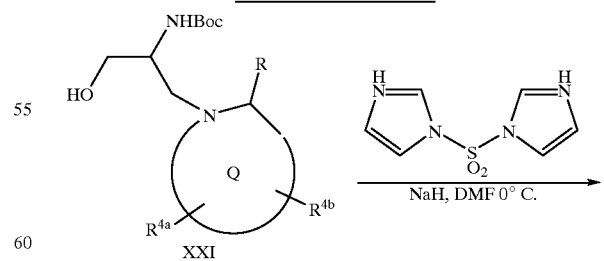

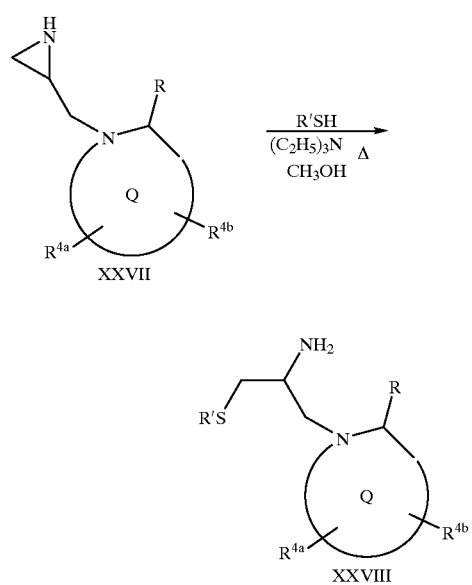

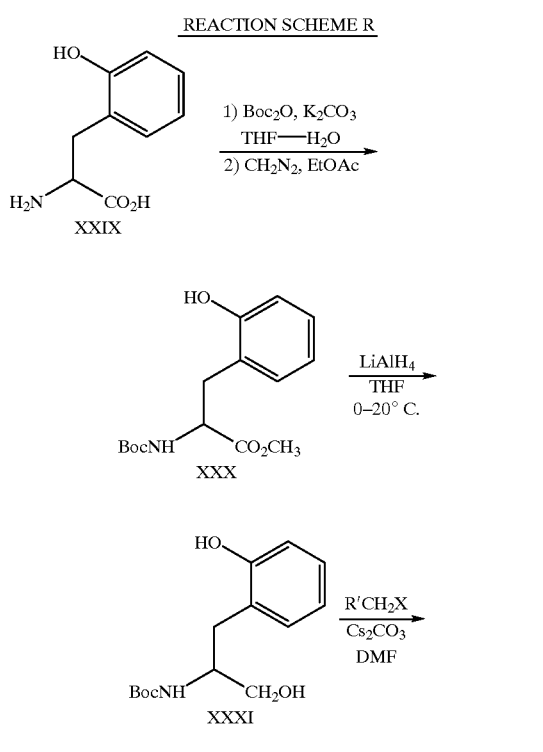

REACTION SCHEME R

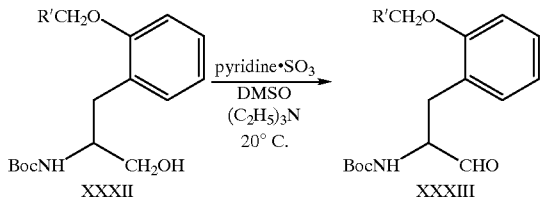

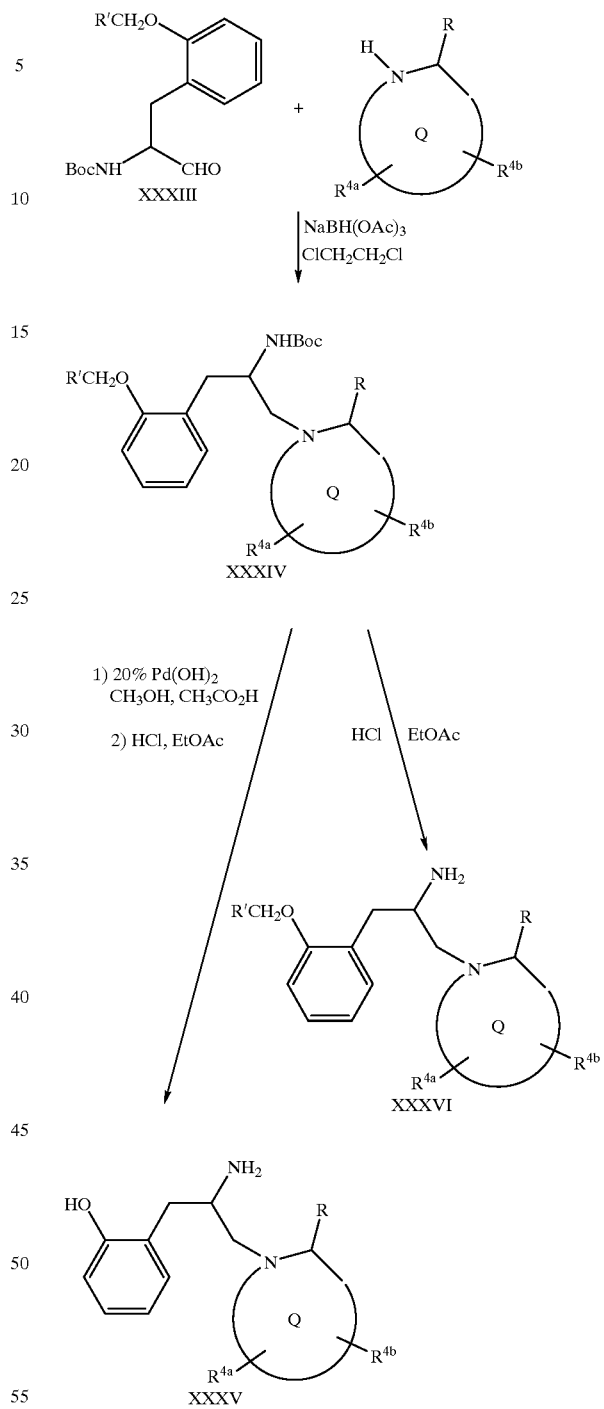

Reactions used to generate the inhibitors of this invention which are designated "y" are shown in the Reaction Schemes 1–16, in addition to other standard manipulations such as ester hydrolysis, cleavage of protecting groups, etc., as may be known in the literature or exemplified in the experimental procedures. Substituents $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Reaction Schemes. Reaction Schemes 1–16 are also useful in preparing inhibitors of this invention that are designated Synopsis of reaction Schemes 1–16:

The requisite intermediates are in some cases commercially available, or can be prepared according to literature procedures, for the most part. In Scheme 1, for example, the synthesis of 2-alkyl substituted piperazines is outlined, and is essentially that described by J. S. Kiely and S. R. Priebe in *Organic Preparations and Proceedings Int.*, 1990, 22, 761–768. Boc-protected amino acids I, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylaminopropyl) carbodiimide hydrochloride) in a solvent such as methylene chloride, chloroform, dichloroethane, or in dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in refluxing ether gives the piperazine IV, which is protected as the Boc derivative V. The N-benzyl group can be cleaved under standard conditions of hydrogenation, e.g., 10% palladium on carbon at 60 psi hydrogen on a Parr apparatus for 24–48 h. The product VI can be treated with an acid chloride, or a carboxylic acid under standard dehydrating conditions to furnish the carboxamides VII; a final acid deprotection as previously described gives the intermediate VIII (Scheme 2). The intermediate VIII can be reductively alkylated with a variety of aldehydes, such as IX. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected to give the final compounds XI with trifluoroacetic acid in methylene chloride. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

Alternatively, the protected piperazine intermediate VII can be reductively alkylated with other aldehydes such as 1-trityl-4-carboxaldehyde or 1-trityl-4-imidazolylacetaldehyde, to give products such as XVI (Scheme IV). The trityl protecting group can be removed from XVI to give XVII, or alternatively, XVI can first be treated with an alkyl halide then subsequently deprotected to give the alkylated imidazole XVIII. Alternatively, the intermediate VIII can be acylated or sulfonylated by standard techniques. The imidazole acetic acid XIX can be converted to the acetate XXI by standard procedures, and XXI can be first reacted with an alkyl halide, then treated with refluxing methanol to provide the regiospecifically alkylated imidazole acetic acid ester XXII. Hydrolysis and reaction with piperazine VIII in the presence of condensing reagents such as 1-(3-dimethylaminopropyl)-3-ethylcarbodiimide (EDC) leads to acylated products such as XXIV.

If the piperazine VIII is reductively alkylated with an aldehyde which also has a protected hydroxyl group, such as XXV in Scheme 6, the protecting groups can be subsequently removed to unmask the hydroxyl group (Schemes 6, 7). The alcohol can be oxidized under standard conditions to e.g. an aldehyde, which can then be reacted with a variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 7), or tertiary amines.

The Boc protected amino alcohol XXVII can also be utilized to synthesize 2-aziridinylmethylpiperazines such as XXXII (Scheme 8). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, the piperazine VIII can be reacted with aldehydes derived from amino acids such as O-alkylated tyrosines, according to standard procedures, to obtain compounds such as XXXIX. When R' is an aryl group, XXXIX can first be hydrogenated to unmask the phenol, and the amine group deprotected with acid to produce XL. Alternatively, the amine protecting group in XXXIX can be removed, and O-alkylated phenolic amines such as XLI produced.

Depending on the identity of the amino acid I, various side chains can be incorporated into the piperazine. For example when I is the Boc-protected β-benzyl ester of aspartic acid, the intermediate diketopiperazine XLII where n=1 and R=benzyl is obtained, as shown in Scheme 10. Subsequent lithium aluminum hydride reduction reduces the ester to the alcohol XLIII, which can then be reacted with a variety of alkylating agents such as an alkyl iodide, under basic conditions, for example, sodium hydride in dimethylformamide or tetrahydrofuran. The resulting ether XLIV can then be carried on to final products as described in Schemes 3–9.

N-Aryl piperazines can be prepared as described in Scheme 11. An aryl amine XLV is reacted with bis-chloroethyl amine hydrochloride (XLVI) in refluxing n-butanol to furnish compounds XLVII. The resulting piperazines XLVII can then be carried on to final products as described in Schemes 3–9.

Piperazin-5-ones can be prepared as shown in Scheme 12. Reductive amination of Boc-protected amino aldehydes XLIX (prepared from I as described previously) gives rise to compound L. This is then reacted with bromoacetyl bromide under Schotten-Baumann conditions; ring closure is effected with a base such as sodium hydride in a polar aprotic solvent such as dimethylformamide to give LI. The carbamate protecting group is removed under acidic conditions such as trifluoroacetic acid in methylene chloride, or hydrogen chloride gas in methanol or ethyl acetate, and the resulting piperazine can then be carried on to final products as described in Schemes 3–9.

The isomeric piperazin-3-ones can be prepared as described in Scheme 13. The imine formed from arylcarboxamides LII and 2-aminoglycinal diethyl acetal (LIII) can be reduced under a variety of conditions, including sodium triacetoxyborohydride in dichloroethane, to give the amine LIV. Amino acids I can be coupled to amines LIV under standard conditions, and the resulting amide LV when treated with aqueous acid in tetrahydrofuran can cyclize to the unsaturated LVI. Catalytic hydrogenation under standard conditions gives the requisite intermediate LVII, which is elaborated to final products as described in Schemes 3–9.

Access to alternatively substituted piperazines is described in Scheme 14. Following deprotection with trifluoroacetic acid, the N-benzyl piperazine V can be acylated with an aryl carboxylic acid. The resulting N-benzyl aryl carboxamide LIX can be hydrogenated in the presence of a catalyst to give the piperazine carboxamide LX which can then be carried on to final products as described in Schemes 3–9.

Reaction Scheme 15 provides an illustrative example the synthesis of compounds of the instant invention wherein the substituents $R^2$ and $R^3$ are combined to form $-(CH_2)_u-$. For example, 1-aminocyclohexane-1-carboxylic acid LXI can be converted to the spiropiperazine LXVI essentially according to the procedures outlined in Schemes 1 and 2. The piperazine intermediate LXIX can be deprotected as before, and carried on to final products as described in Schemes 3–9. It is understood that reagents utilized to provide the substituent Y which is 2-(naphthyl) and the imidazolylalkyl substituent may be readily replaced by other reagents well known in the art and readily available to provide other N-substituents on the piperazine.

The aldehyde XLIX from Scheme 12 can also be reductively alkylated with an aniline as shown in Scheme 16. The product LXXI can be converted to a piperazinone by acylation with chloroacetyl chloride to give LXXII, followed by base-induced cyclization to LXXIII. Deprotection, followed by reductive alkylation with a protected imidazole carboxaldehyde leads to LXXV, which can be alkylation with an arylmethylhalide to give the imidazolium salt LXXVI. Final removal of protecting groups by either solvolysis with a lower alkyl alcohol, such as methanol, or treatment with triethylsilane in methylene chloride in the presence of trifluoroacetic acid gives the final product LXXVII.

SCHEME 1

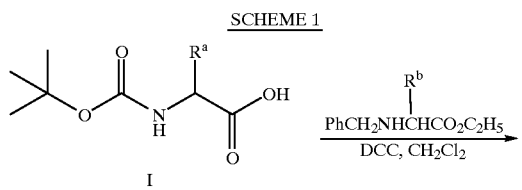

I

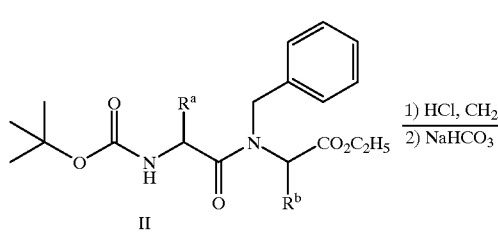

II

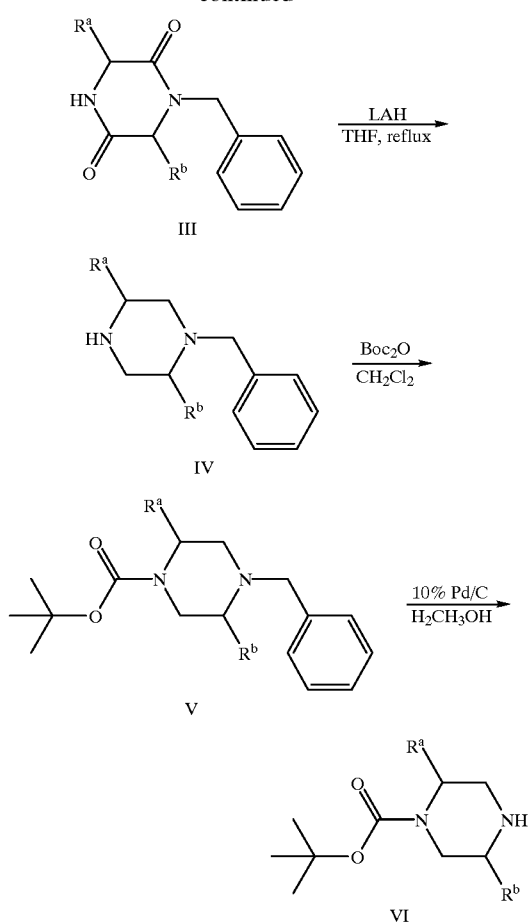

SCHEME 2

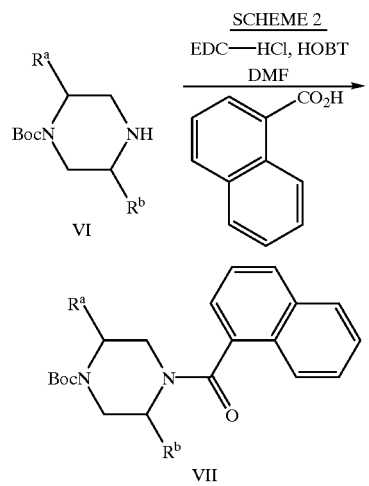

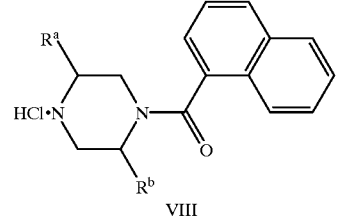

SCHEME 3
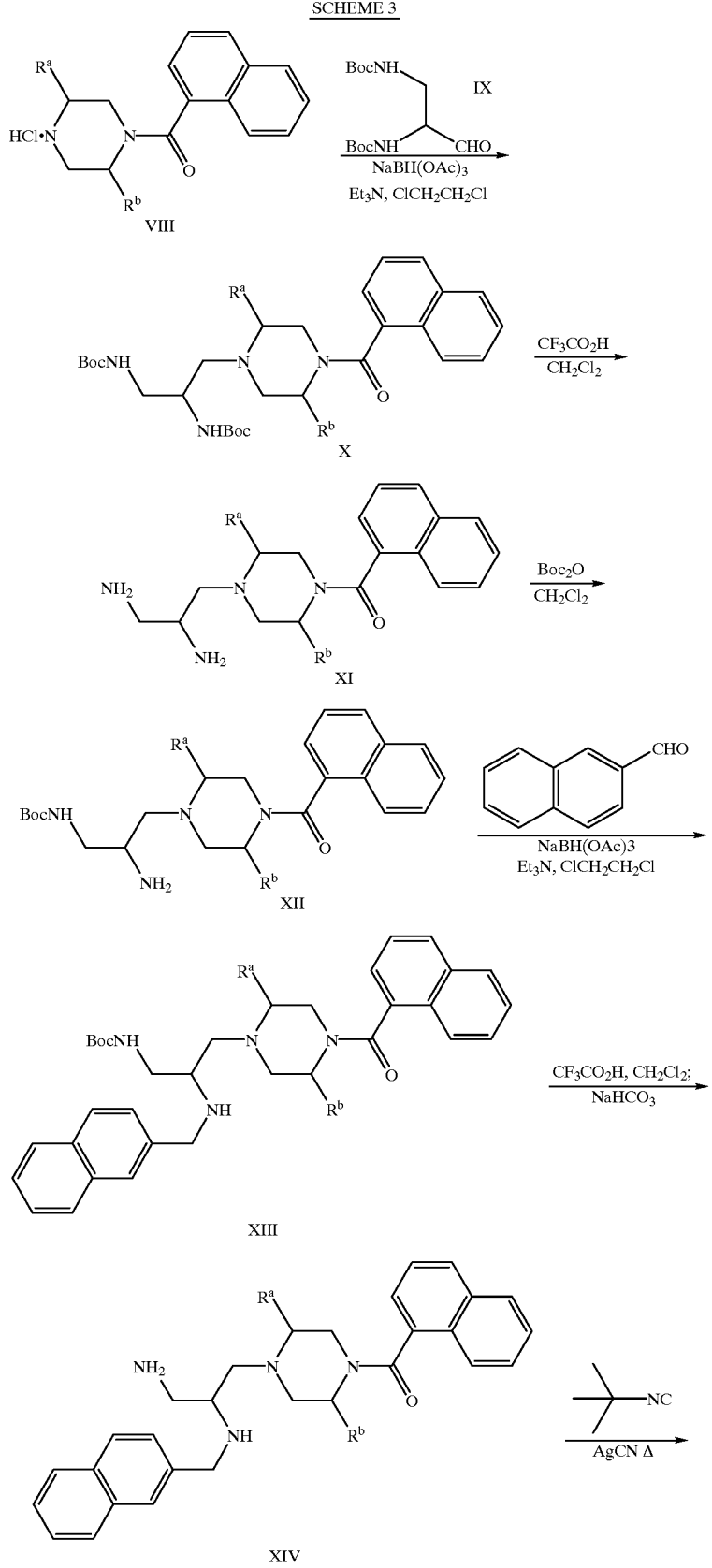

-continued
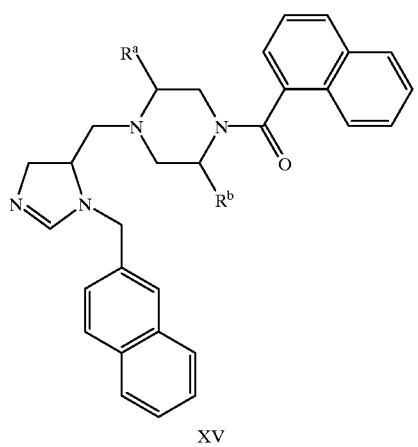
XV
SCHEME 4
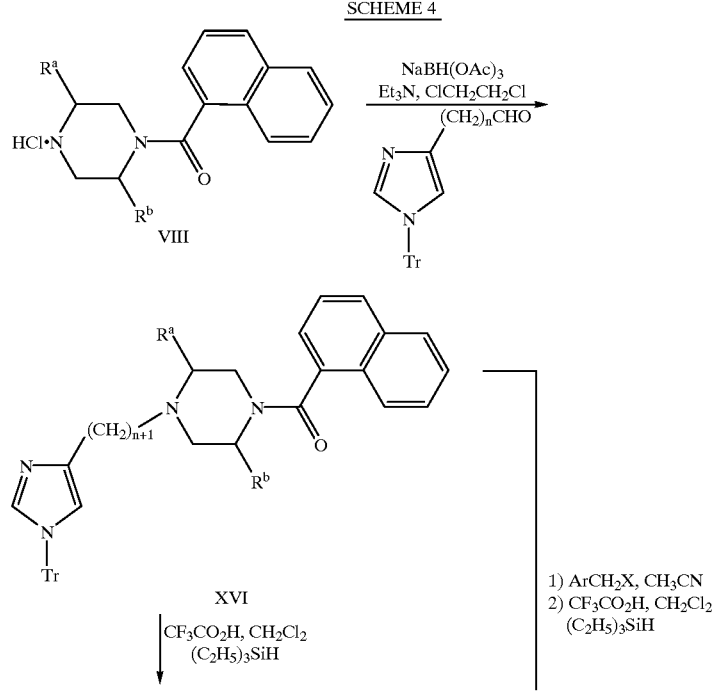

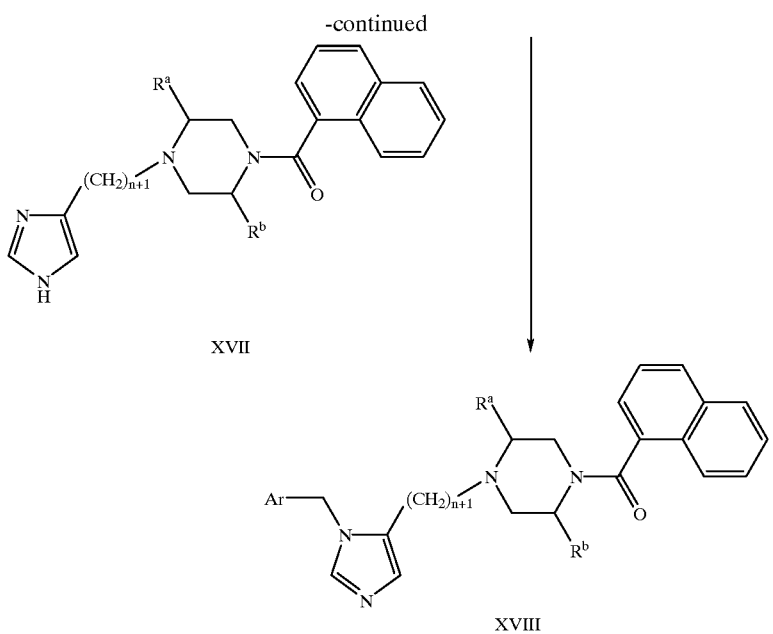
XVII
XVIII
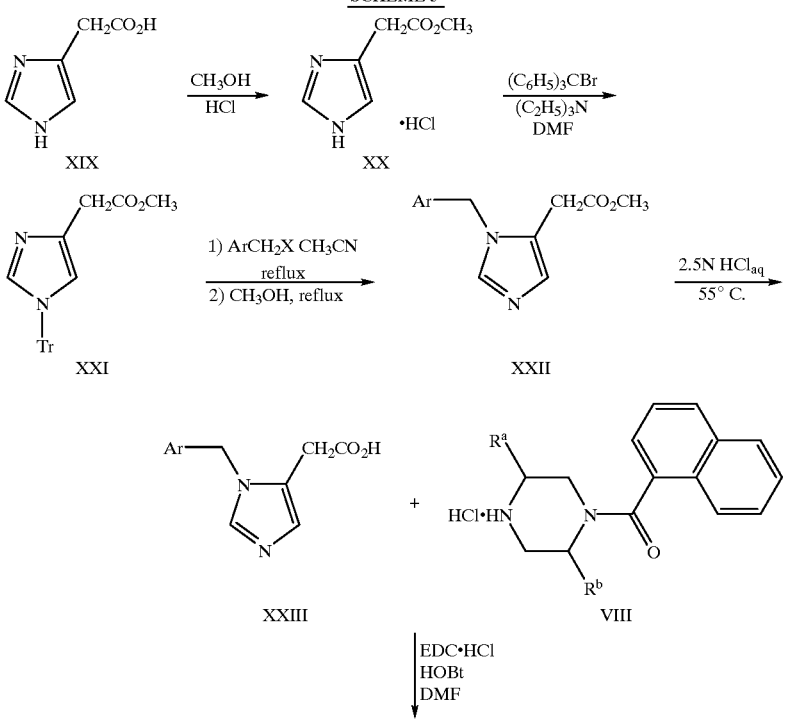
SCHEME 5

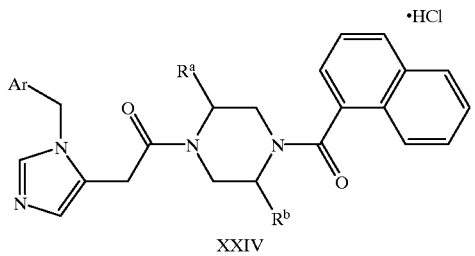
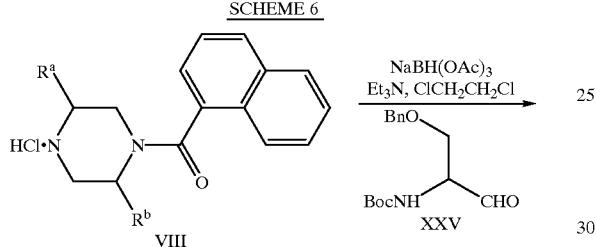
SCHEME 6
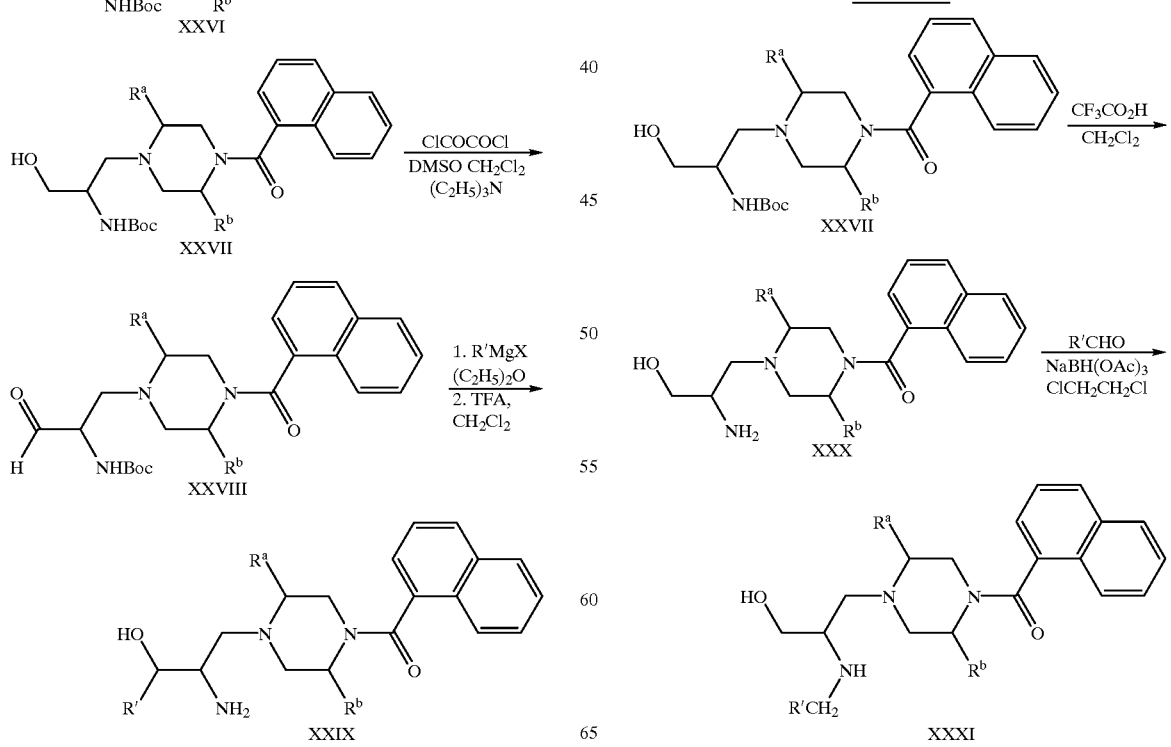
SCHEME 7

SCHEME 8
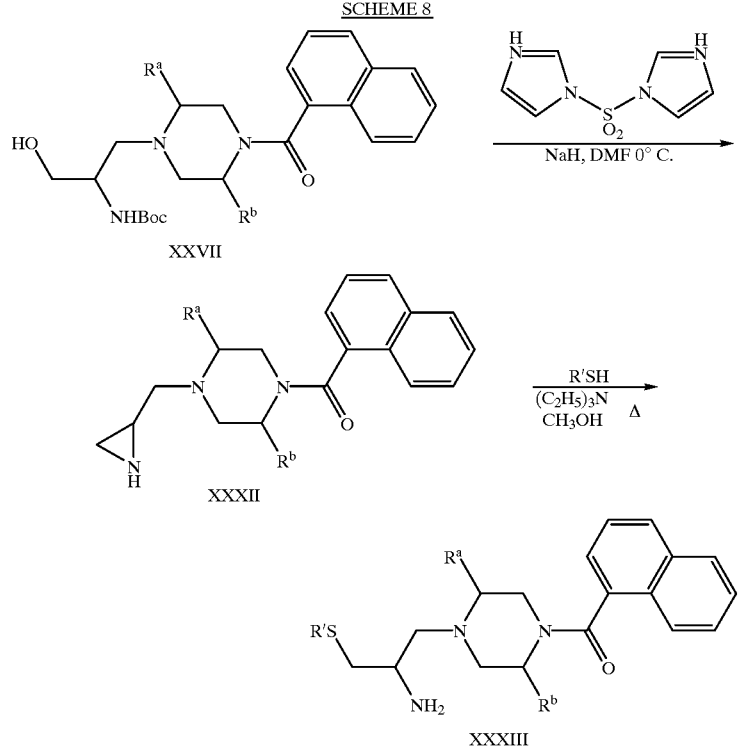
SCHEME 9
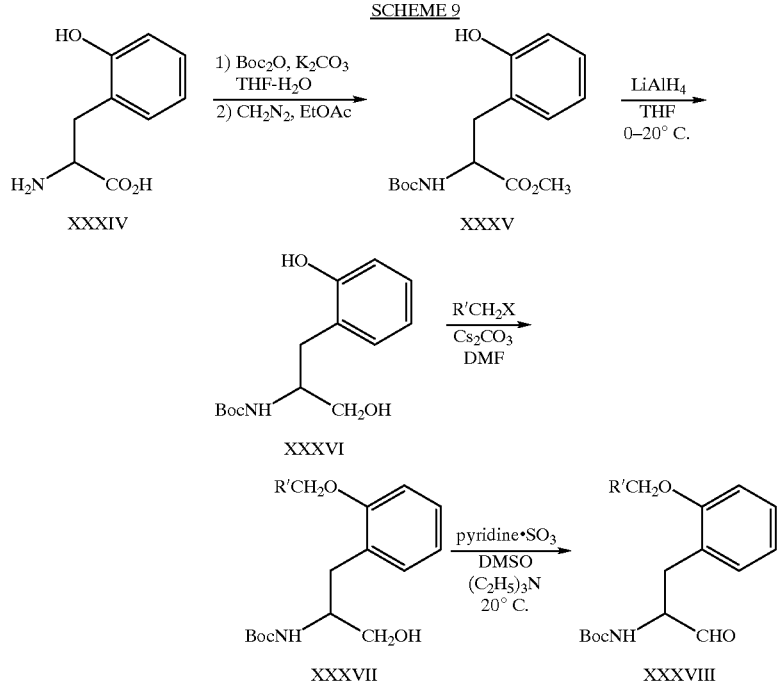

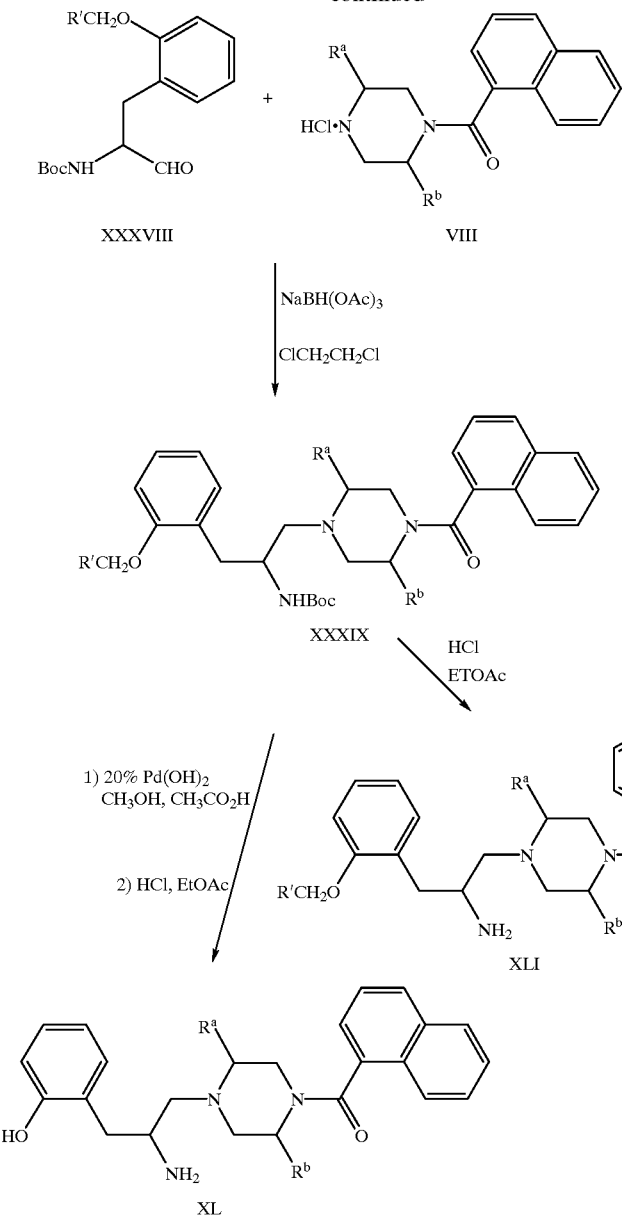
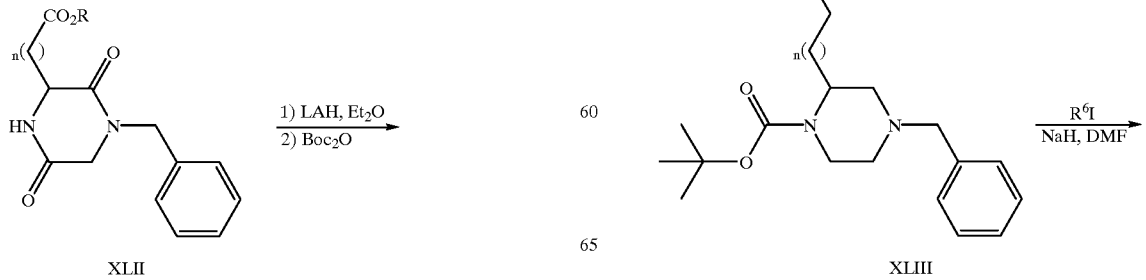
SCHEME 10

-continued
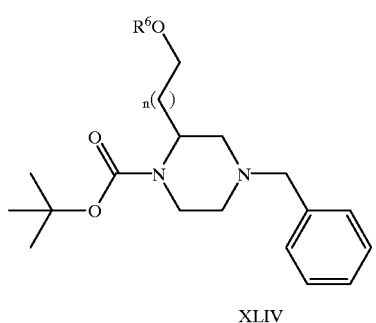
XLIV
-continued
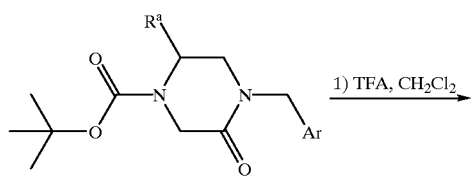
LI
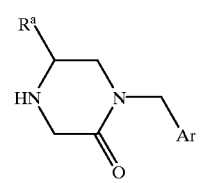
SCHEME 11
ArNH₂ + 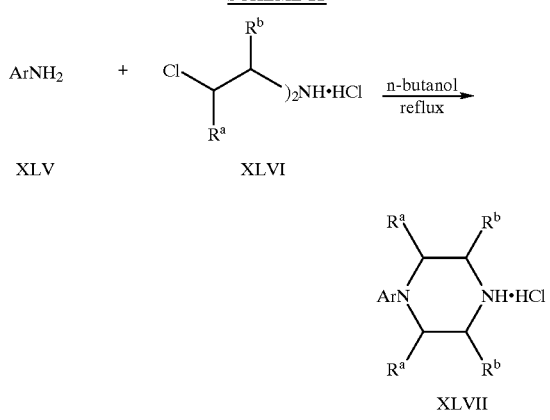
XLV   XLVI
XLVII
SCHEME 13
ArCHO + NH₂CH₂CH(OC₂H₅)₂ →(NaBH(OAc)₃)
LII   LIII
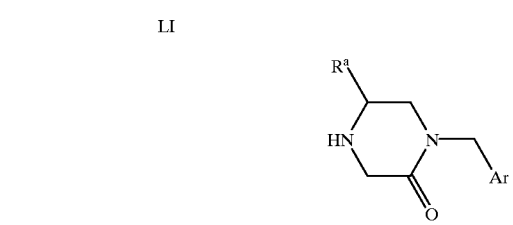
SCHEME 12
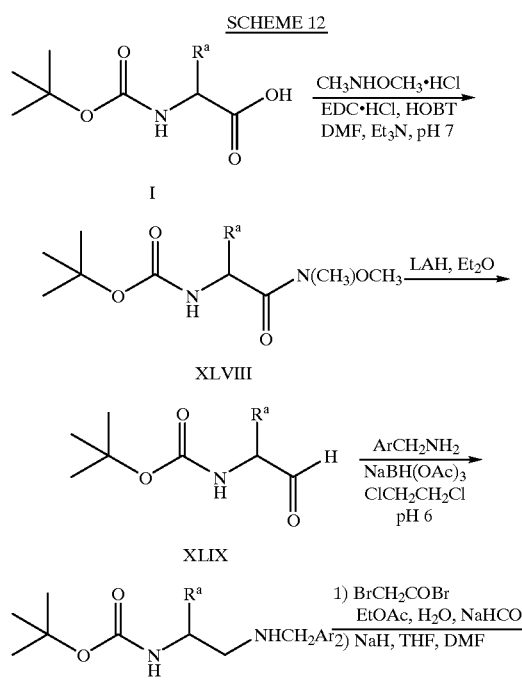
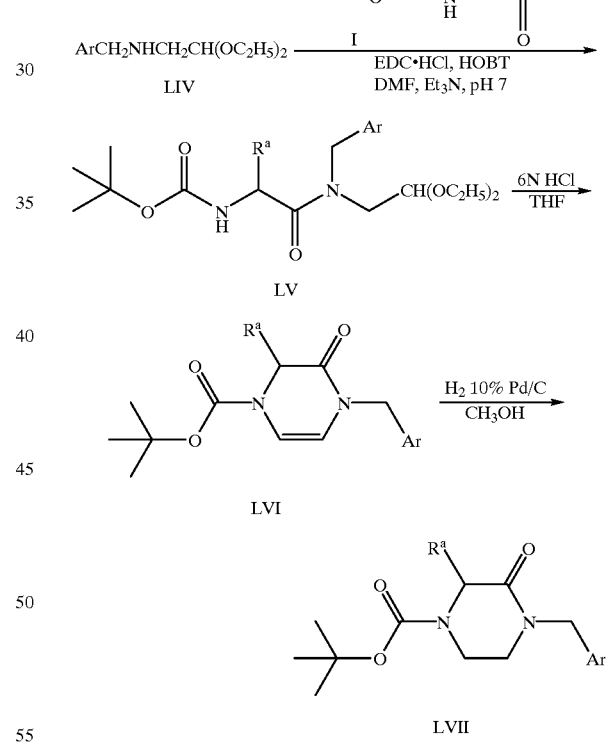
SCHEME 14
V  1) CF₃CO₂H, CH₂Cl₂
   2) NaHCO₃

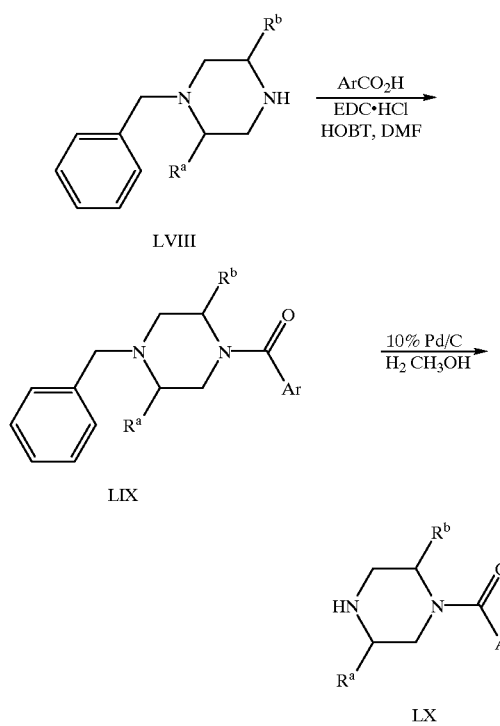
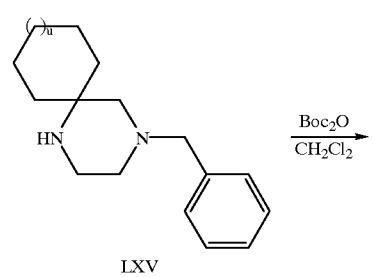
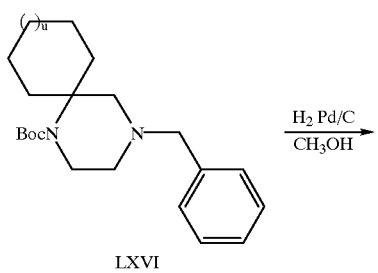
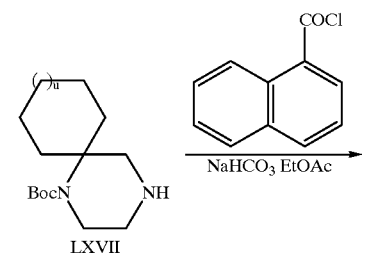
SCHEME 15
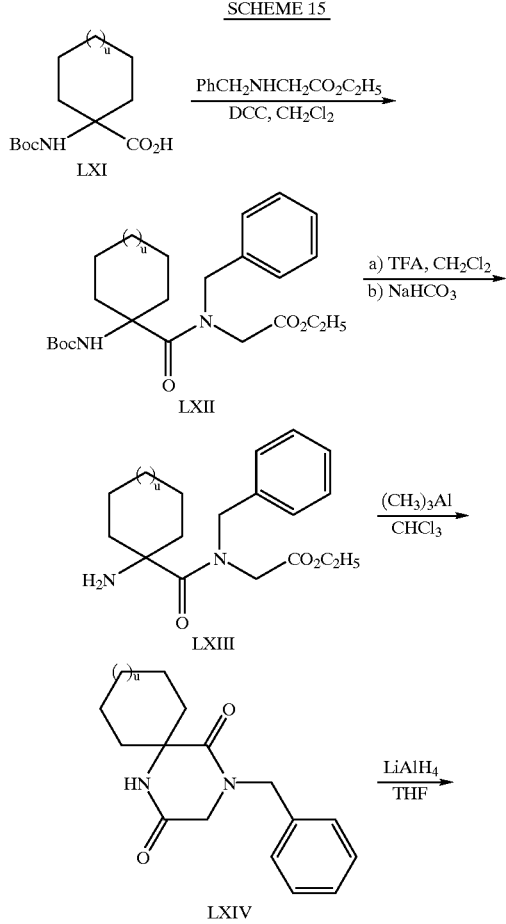
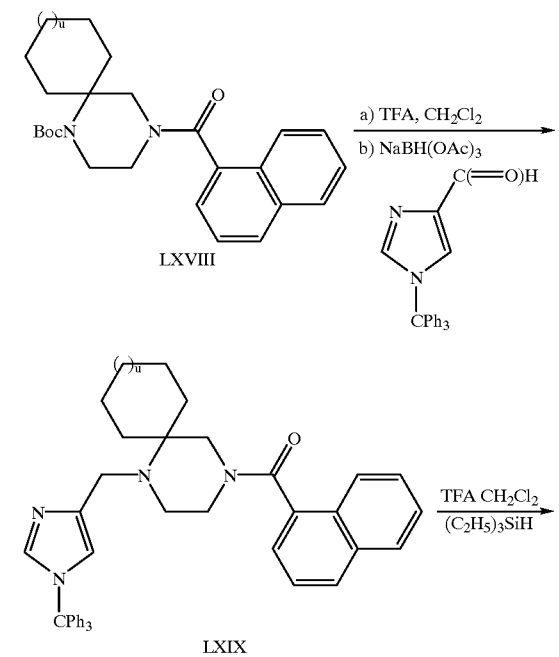

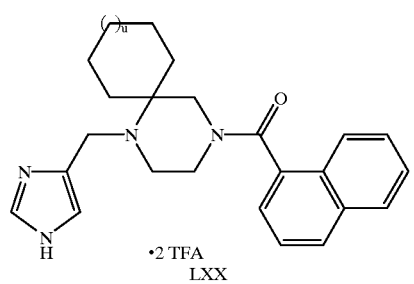

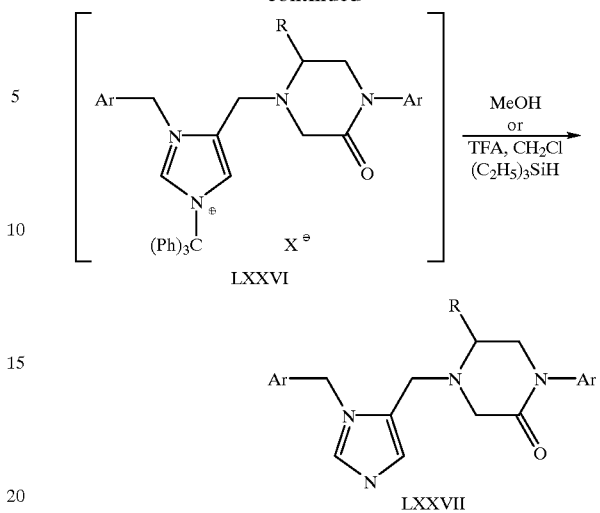

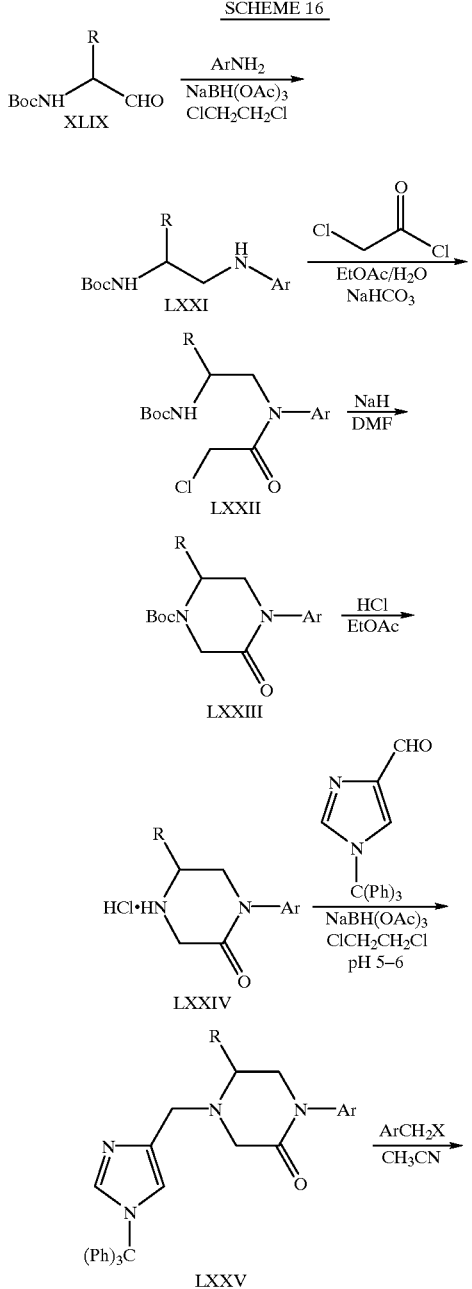

The compositions of this invention inhibit Ras farnesyl transferase which catalyzes the first step in the post-translational processing of Ras and the biosynthesis of functional Ras protein. These compositions are useful as pharmaceutical agents for mammals, especially for humans. These compositions may be administered to patients for use in the treatment of benign proliferative disorder neurofibromatosis and symptoms associated with neurofibromatosis such as benign neurofibromas, optic gliomas, pseudoarthoses and learning disabilities. The compositions may also be administered to young mammals who are genetically disposed to NF1 prior to the manifestation of the disease, thereby preventing the disease or lessening its effects.

In practicing the methods of this invention, which comprise administering a composition comprising a farnesyl-protein transferase inhibitor, such administration can be orally or parenterally, including the intravenous, intramuscular, intraperitoneal, subcutaneous, rectal and topical routes of administration. It is preferred that such administration be orally. It is more preferred that such administration be orally and simultaneously.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice.

For oral use of an anti-benign proliferative disorder neurofibromatosis composition according to this invention, the selected composition may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a composition according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of composition is administered to a mammal undergoing treatment for benign proliferative disorder neurofibromatosis. Administration occurs in an amount of a composition that comprises between about 0.1 mg/kg of body weight to about 40 mg/kg of body weight per day, preferably of between 0.5 mg/kg of body weight to about 20 mg/kg of body weight per day of a farnesyl-protein transferase inhibitor.

EXAMPLES

Examples provided are intended to assist in a further understanding of the invention. Particular materials employed, species and conditions are intended to be further illustrative of the invention and not limitative of the reasonable scope thereof.

Example 1
In vitro inhibition of ras farnesyl transferase

Assays of farnesyl-protein transferase. Partially purified bovine FPTase and Ras peptides (Ras-CVLS, Ras-CVIM and RAS-CAIL) is prepared as described by Schaber et al., J. Biol. Chem. 265:14701–14704 (1990), Pompliano, et al., Biochemistry 31:3800 (1992) and Gibbs et al., PNAS U.S.A. 86:6630–6634 (1989), respectively. Bovine FPTase is assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions are initiated with FPTase and stopped with 1 ml of 1.0 M HCL in ethanol. Precipitates are collected onto filter-mats using a TomTec Mach II cell harvestor, washed with 100% ethanol, dried and counted in an LKB β-plate counter. The assay is linear with respect to both substrates, FPTase levels and time; less than 10% of the [$^3$H]-FPP is utilized during the reaction period. Individual purified protein substrate-competitive inhibitor and/or farnesyl pyrophosphate-competitive inhibitor and compositions of the invention that comprise at least one of a protein substrate-competitive inhibitor and a farnesyl pyrophosphate-competitive inhibitor are dissolved in 100% dimethyl sulfoxide (DMSO) and are diluted 20-fold into the assay. Percentage inhibition is measured by the amount of incorporation of radioactivity in the presence of the test compound when compared to the amount of incorporation in the absence of the test compound.

Human FPTase is prepared as described by Omer et al., Biochemistry 32:5167–5176 (1993). Human FPTase activity is assayed as described above with the exception that 0.1% (w/v) polyethylene glycol 20,000, 10 μM $ZnCl_2$ and 100 nM Ras-CVIM are added to the reaction mixture. Reactions are performed for 30 min., stopped with 100 μl of 30% (v/v) trichloroacetic acid (TCA) in ethanol and processed as described above for the bovine enzyme.

Comparison is made between the inhibitory activity of a composition of the instant invention and the inhibitory activities of individual compounds that make up the composition in the assay.

Example 2
In vivo ras farnesylation assay

The cell line used in this assay is a v-ras line derived from either Rat1 or NIH3T3 cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000× g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Comparison is made between the inhibitory activity of a composition of the instant invention and the inhibitory activities of individual compounds that make up the composition in the assay.

Figure 1:
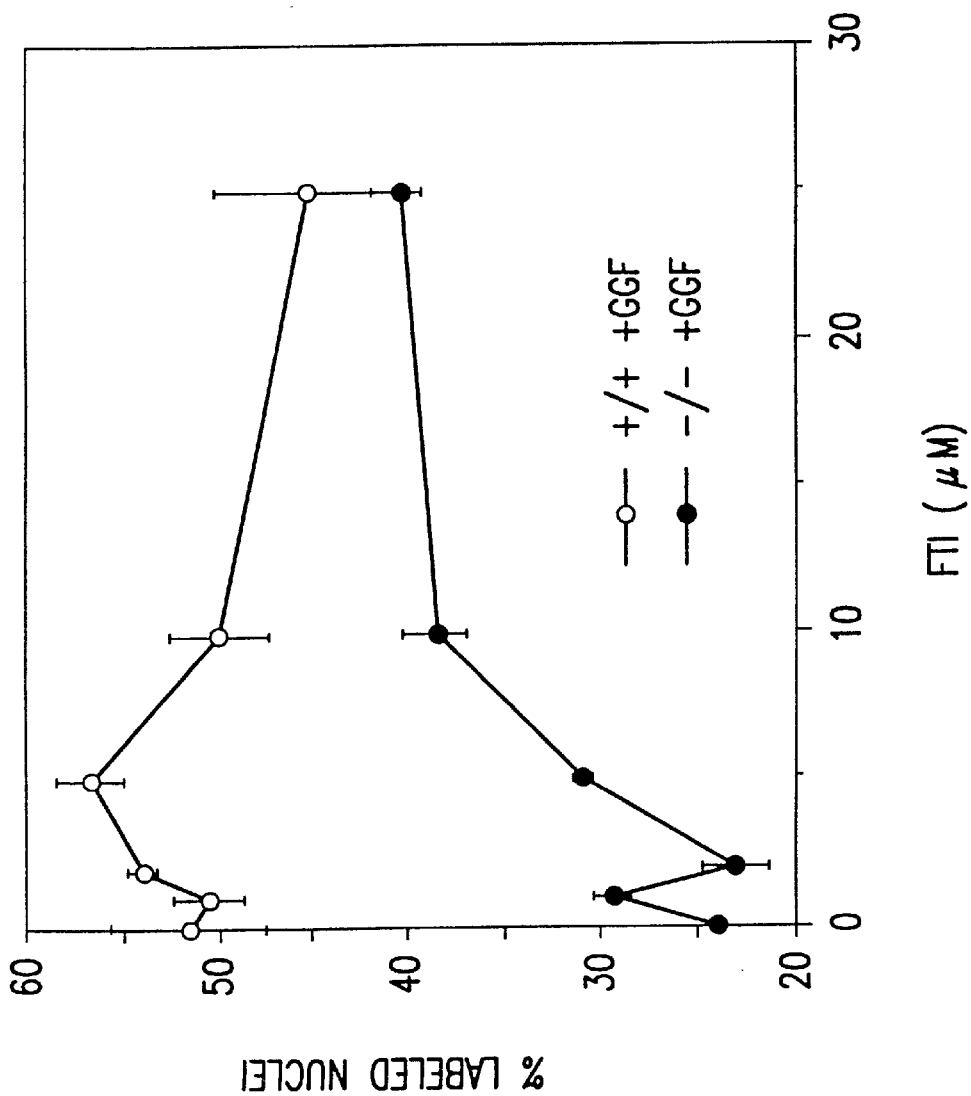
FIG. 1 Effect of a Farnesyl-protein Transferase Inhibitor on NF1 Schwann Cells:
Cell proliferation of NF1 wild type mouse Schwann cells (+/+) and mutant type cells (−/−) which were preincubated with various concentrations Compound A. After preincubation the cells were exposed to medium containing glial growth factor.

Example 3
Effect of Compound A on NFJ Schwann cells:

Wild type and homozygous mutant mouse Schwann cells were isolated from E12.5NF1 mouse embryos and plated at 25,000 cells per well on a poly-L-lysine coated 8 well glass Lab-Tek slide in DMEMmedia containing 10% FBS. Various concentrations of Compound A were added to the culture medium and the cultures preincubated for two days. After the preincubation the culture medium was changed to a serum-free medium supplemented with glial growth factor. The following day, [$^3$H]-thymidine (4 μCi/ml) was added to the culture and after 16–18 hours of labeling period, cells were fixed and processed for autoradiography and immunostaining for nerve growth factor receptor (NGFR). Schwann cell DNA synthesis was determined by counting the percentage of labeled nuclei of NGFR positive cells. The results are shown in FIG. 1.

Figure 2:
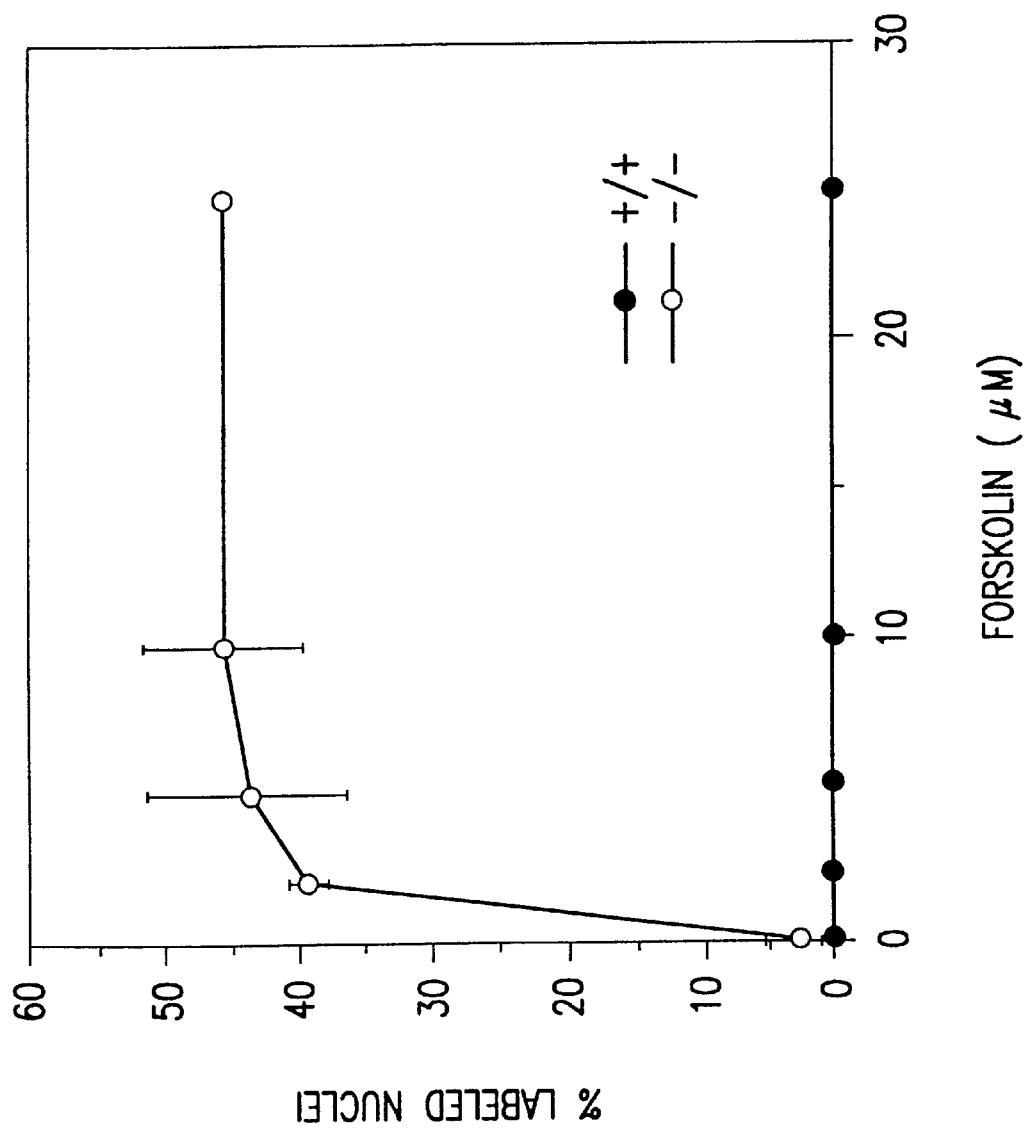
FIG. 2 Proliferation of NF1Null Schwann Cells in the Presence of Forskolin.

Example 4
Effect of Forskolin on NF1Schwann cells:

Wild type and homozygous mutant mouse Schwann cells were isolated from E12.5NF1 mouse embryos and plated at 25,000 cells per well on a poly-L-lysine coated 8 well glass Lab-Tek slide in DMEMmedia containing 10% FBS. After the preincubation the culture medium was changed to a serum-free medium supplemented with various concentrations of forskolin. The following day, [³H]-thymidine (4 µCi/ml) was added to the culture and after 16–18 hours of labeling period, cells were fixed and processed for autoradiography and immunostaining for NGFR. Schwann cell DNA synthesis was determined by counting the percentage of labeled nuclei of NGFR positive cells. The results are shown in FIG. 2.

Example 5

Effect of Compound A on Forskolin mediated NFJ Schwann cell growth:

Homozygous mutant mouse Schwann cells were isolated from E12.5NF1 mouse embryos and plated at 25,000 cells per well on a poly-L-lysine coated 8 well glass Lab-Tek slide in DMEM media containing 10% FBS. Various concentrations of Compound A were added to the culture medium and the cultures preincubated for two days. After the preincubation the culture medium was changed to a serum-free medium supplemented with 2 µM of forskolin. The following day, [³H]-thymidine (4 µCi/ml) was added to the culture and after 16–18 hours of labeling period, cells were fixed and processed for autoradiography and immunostaining for NGFR. Schwann cell DNA synthesis was determined by counting the percentage of labeled nuclei of NGFR positive cells. The results are shown in FIG. 3.

What is claimed is:

1. A method for treating benign proliferative disorder neurofibromatosis in a mammal in need thereof which comprises administering to said mammal a pharmaceutically effective amount of a compound that inhibits farnesyl-protein transferase, which is selected from the compounds of formulae I, II, III and IV:

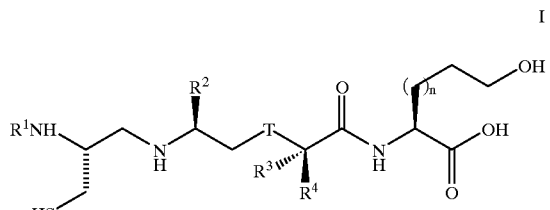
I

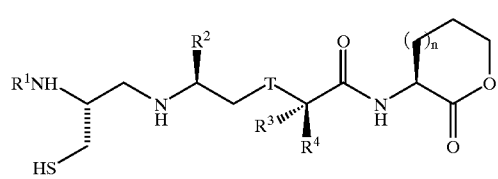
II

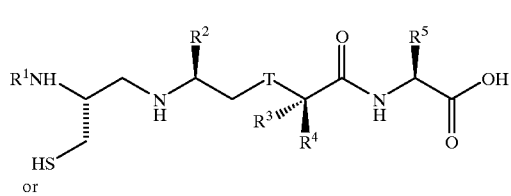
III or

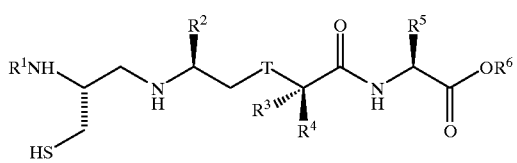
IV wherein, $R^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

$R^2$, $R^3$ and $R^5$ are
  the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

$R^4$ is hydrogen or an alkyl group, wherein the alkyl group comprises straight chain or branched chain hydrocarbons of 1 to 6 carbon atoms;

$R^6$ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;

T is O or $S(O)_m$;

m is 0, 1 or 2; and n is 0, 1 or 2;

or a pharmaceutically acceptable salt thereof.

2. A method for preventing benign proliferative disorder neurofibromatosis in a mammal in need thereof which comprises administering to said mammal a pharmaceutically effective amount of a compound that inhibits farnesyl-protein transferase, which is selected from the compounds of formulae I, II, III and IV:

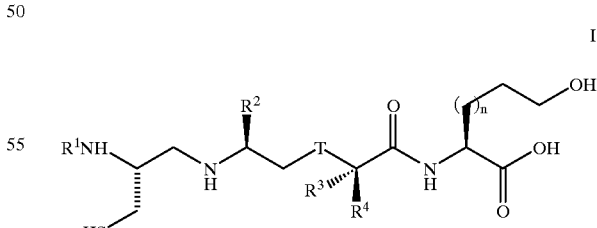
I

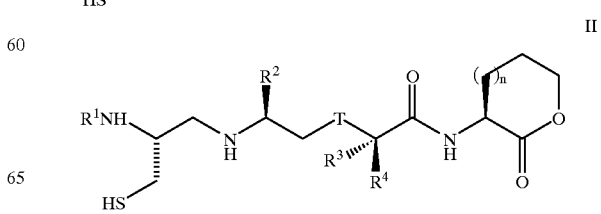
II

III

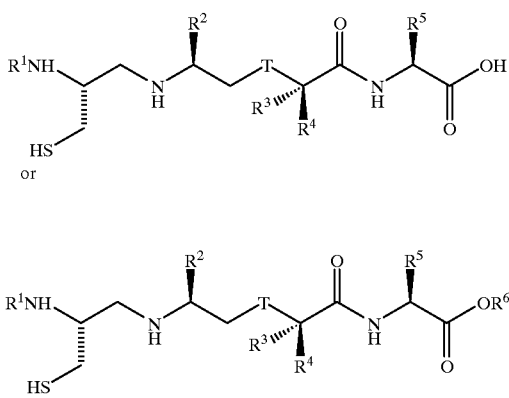

or

IV wherein,

R¹ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

R², R³ and R⁵ are the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

R⁴ is hydrogen or an alkyl group, wherein the alkyl group comprises straight chain or branched chain hydrocarbons of 1 to 6 carbon atoms;

R⁶ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;

T is O or $S(O)_m$;

m is 0, 1 or 2; and n is 0, 1 or 2;

or a pharmaceutically acceptable salt thereof.

3. A method for treating benign proliferative disorder neurofibromatosis in a mammal in need thereof which comprises administering to said mammal a pharmaceutically effective amount of a compound that inhibits farnesyl-protein transferase, which is selected from the compounds of formulae A, B and C:

A

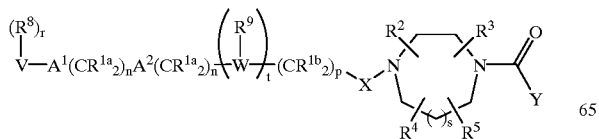

B

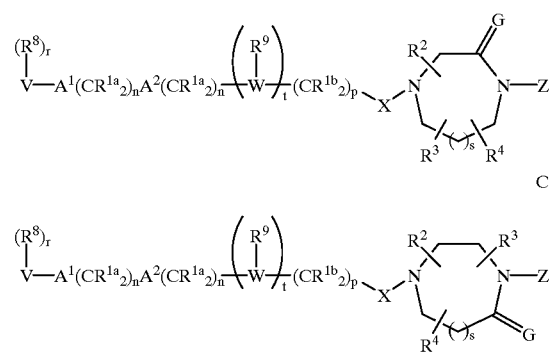

C wherein:

$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

R² and R³ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

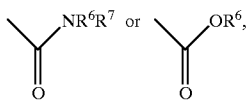

wherein the substituted group is substituted with one or more of:
1) aryl or heterocycle, unsubstituted or substituted with:
a) $C_{1-4}$ alkyl,
b) $(CH_2)_pOR^6$,
c) $(CH_2)_pNR^6R^7$,
d) halogen,
2) $C_{3-6}$ cycloalkyl,
3) $OR^6$,
4) $SR^6$, $S(O)R^6$, $SO_2R^6$,
5)
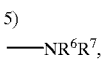
6)
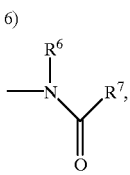

-continued

7)
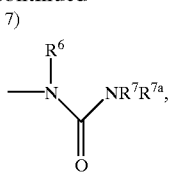

8)
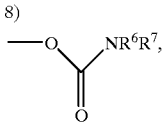

9)
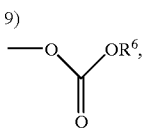

10)
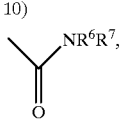

11)
—SO$_2$—NR$^6$R$^7$,

12)
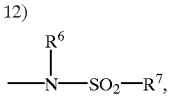

13)
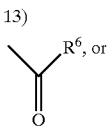, or

14)
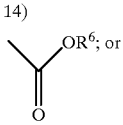; or

R$^2$ and R$^3$ are attached to the same C atom and are combined to form —(CH$_2$)$_u$— wherein one of the carbon atoms is optionally replaced by a moiety selected from: O, S(O)$_m$, —NC(O)—, and —N(COR$^{10}$)—, R$^4$ is selected from H and CH$_3$;

and any two of R$^2$, R$^3$ and R$^4$ are optionally attached to the same carbon atom;

R$^6$, R$^7$ and R$^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
a) C$_{1-4}$ alkoxy,
b) aryl or heterocycle,
c) halogen,
d) HO,
e)
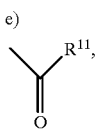
f) —SO$_2$R$^{11}$, or
g) N(R$^{10}$)$_2$; or R$^6$ and R$^7$ may be joined in a ring;

R$^7$ and R$^{7a}$ may be joined in a ring;

R$^8$ is independently selected from:
a) hydrogen,
b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

R$^9$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

G is H$_2$ or O;

V is selected from:
a) hydrogen,
b) heterocycle,
c) aryl,
d) C$_1$–C$_{20}$ alkyl wherein from 0 to 4 carbon atoms are replaced with a a heteroatom selected from O, S, and N, and
e) C$_2$–C$_{20}$ alkenyl, provided that V is not hydrogen if A$^1$ is S(O)$_m$ and V is not hydrogen if A$^1$ is a bond, n is 0 and A$^2$ is S(O)$_m$;

W is a heterocycle;

X is —CH$_2$—, —C(=O)—, or S(=O)$_m$—;

Y is aryl, heterocycle, unsubstituted or substituted with one or more of:
1) C$_{1-4}$ alkyl, unsubstituted or substituted with:
a) C$_{1-4}$ alkoxy,
b) NR$^6$R$^7$,
c) C$_{3-6}$ cycloalkyl,
d) aryl or heterocycle,
e) HO,
f) —S(O)$_m$R$^6$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^6$,
10) —C(O)NR$^6$R$^7$, or
11) C$_3$–C$_6$ cycloalkyl;

Z is aryl, heteroaryl, arylmethyl, heteroarylmethyl, arylsulfonyl, heteroarylsulfonyl, unsubstituted or substituted with one or more of the following:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) $-S(O)_m R^6$, or
   g) $-C(O)NR^6R^7$,
2) aryl or heterocycle,
3) halogen,
4) $OR^6$,
5) $NR^6R^7$,
6) CN,
7) $NO_2$,
8) $CF_3$;
9) $-S(O)_m R^6$,
10) $-C(O)NR^6R^7$, or
11) $C_3-C_6$ cycloalkyl;
m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1; and
u is 4 or 5;
or a pharmaceutically acceptable salt thereof.

4. A method for preventing benign proliferative disorder neurofibromatosis in a mammal in need thereof which comprises administering to said mammal a pharmaceutically effective amount of a compound that inhibits farnesyl-protein transferase, which is selected from the compounds of formulae A, B and C:

A $$(R^8)_r\text{-}V\text{-}A^1(CR^{1a}_2)_n A^2(CR^{1a}_2)_n\text{-}(W)_t\text{-}(CR^{1b}_2)_p\text{-}X\text{-}N(R^2)(R^3)\cdots N\text{-}C(O)\text{-}Y \text{ with } R^9, R^4, R^5$$

B $$(R^8)_r\text{-}V\text{-}A^1(CR^{1a}_2)_n A^2(CR^{1a}_2)_n\text{-}(W)_t\text{-}(CR^{1b}_2)_p\text{-}X\text{-}N(R^2)\text{-}C(=O)\text{-}N(Z)\cdots \text{ with } R^9, R^3, R^4$$

C $$(R^8)_r\text{-}V\text{-}A^1(CR^{1a}_2)_n A^2(CR^{1a}_2)_n\text{-}(W)_t\text{-}(CR^{1b}_2)_p\text{-}X\text{-}N(R^2)(R^3)\cdots N\text{-}Z\text{ with }C(=G), R^9, R^4$$

wherein:
$R^{1a}$ and $R^{1b}$ are independently selected from:
   a) hydrogen,
   b) aryl, heterocycle, $C_3$–$C_{10}$ cycloalkyl, $C_2$–$C_6$ alkenyl, $C_2$–$C_6$ alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N_3$, $-N(R^{10})_2$, or $R^{11}OC(O)NR^{10}-$,
   c) $C_1$–$C_6$ alkyl unsubstituted or substituted by aryl, heterocyclic, $C_3$–$C_{10}$ cycloalkyl, $C_2$–$C_6$ alkenyl, $C_2$–$C_6$ alkynyl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $N_3$, $-N(R^{10})_2$, or $R^{11}OC(O)NR^{10}-$;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle, $$\overset{NR^6R^7}{\underset{O}{\diagdown\!\!\diagup}} \text{ or } \overset{OR^6}{\underset{O}{\diagdown\!\!\diagup}},$$

wherein the substituted group is substituted with one or more of:
1) aryl or heterocycle, unsubstituted or substituted with:
   a) $C_{1-4}$ alkyl,
   b) $(CH_2)_p OR^6$,
   c) $(CH_2)_p NR^6R^7$,
   d) halogen,
2) $C_{3-6}$ cycloalkyl,
3) $OR^6$,
4) $SR^6$, $S(O)R^6$, $SO_2R^6$,

5) $-NR^6R^7$,

6) $-N(R^6)-C(O)R^7$,

7) $-N(R^6)-C(O)NR^7R^{7a}$,

8) $-O-C(O)NR^6R^7$,

9) $-O-C(O)OR^6$,

10) $-C(O)NR^6R^7$,

11) $-SO_2-NR^6R^7$,

12) $-N(R^6)-SO_2-R^7$,

-continued

13)

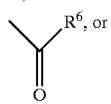

14)

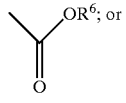

$R^2$ and $R^3$ are attached to the same C atom and are combined to form —(CH$_2$)$_u$— wherein one of the carbon atoms is optionally replaced by a moiety selected from: O, S(O)$_m$, —NC(O)—, and —N(COR$^{10}$)—;

$R^4$ is selected from H and CH$_3$;

and any two of $R^2$, $R^3$ and $R^4$ are optionally attached to the same carbon atom;

$R^6$, $R^7$ and $R^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
  a) C$_{1-4}$ alkoxy,
  b) aryl or heterocycle,
  c) halogen,
  d) HO,
  e)

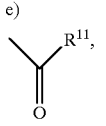

f) —SO$_2$R$^{11}$, or
  g) N(R$^{10}$)$_2$; or $R^6$ and $R^7$ may be joined in a ring;
$R^7$ and $R^{7a}$ may be joined in a ring;
$R^8$ is independently selected from:
  a) hydrogen,
  b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

$R^9$ is selected from:
  a) hydrogen,
  b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

$R^{10}$ is independently selected from hydrogen, C$_1$–C$_6$ alkyl, benzyl and aryl;

$R^{11}$ is independently selected from C$_1$–C$_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

G is H$_2$ or O;

V is selected from:
  a) hydrogen,
  b) heterocycle,
  c) aryl,
  d) C$_1$–C$_{20}$ alkyl wherein from 0 to 4 carbon atoms are replaced with a a heteroatom selected from O, S, and N, and
  e) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is a heterocycle;

X is —CH$_2$—, —C(=O)—, or —S(=O)$_m$—;

Y is aryl, heterocycle, unsubstituted or substituted with one or more of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^6$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$;
  9) —S(O)$_m$R$^6$,
  10) —C(O)NR$^6$R$^7$, or
  11) C$_3$–C$_6$ cycloalkyl;

Z is aryl, heteroaryl, arylmethyl, heteroarylmethyl, arylsulfonyl, heteroarylsulfonyl, unsubstituted or substituted with one or more of the following:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^6$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$;
  9) —S(O)$_m$R$^6$,
  10) —C(O)NR$^6$R$^7$, or
  11) C$_3$–C$_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1; and
u is 4 or 5;

or a pharmaceutically acceptable salt thereof.

5. A method for treating benign proliterative disorder neurofibromatosis in a mammal in need thereof which comprises administering to said mammal a pharmaceutically effective amoount of a compound that inhibits farnesyl-protein transferase.

6. The method according to claim 5 wherein the compound that inhibits farnesyl-protein transferase is Compound A:

7. A method for preventing benign proliferative disorder neurofibromatosis in a mammal in need thereof which comprises administering to said mammal a pharmaceutically effective amount of a compound that inhibits farnesyl-protein transferase.

8. The method according to claim 7 wherein the compound that inhibits farnesyl-protein transferase is Compound A:

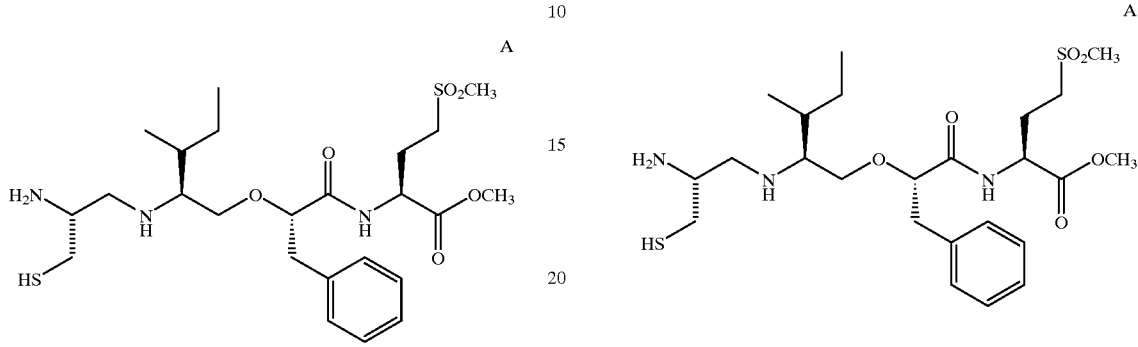

a pharmaceutically acceptable salt therefore.

or a pharmaceutically acceptable salt thereof.

* * * * *